US008920724B2

(12) United States Patent
Nagai et al.

(10) Patent No.: US 8,920,724 B2
(45) Date of Patent: Dec. 30, 2014

(54) SPECIMEN PROCESSING APPARATUS

(75) Inventors: Takaaki Nagai, Kobe (JP); Tokihiro Kosaka, Kakogawa (JP); Yuichi Hamada, Kobe (JP)

(73) Assignee: Sysmex Corporation, Kobe (JP)

( * ) Notice: Subject to any disclaimer, the term of this patent is extended or adjusted under 35 U.S.C. 154(b) by 681 days.

(21) Appl. No.: 12/590,012

(22) Filed: Oct. 30, 2009

(65) Prior Publication Data
US 2010/0111384 A1 May 6, 2010

(30) Foreign Application Priority Data

Oct. 31, 2008 (JP) ................................. 2008-282055
Jun. 30, 2009 (JP) ................................. 2009-155819

(51) Int. Cl.
C12Q 1/68 (2006.01)
G01N 21/00 (2006.01)
G01N 15/06 (2006.01)
B01L 3/00 (2006.01)
G01N 35/02 (2006.01)
G01N 35/10 (2006.01)
G01N 35/00 (2006.01)

(52) U.S. Cl.
CPC .......... *G01N 35/1011* (2013.01); *G01N 35/026* (2013.01); *G01N 35/1079* (2013.01); *G01N 2035/1025* (2013.01); *G01N 2035/00742* (2013.01); *G01N 2035/1013* (2013.01)
USPC ................ 422/68.1; 422/50; 422/62; 422/63; 422/65; 422/501

(58) Field of Classification Search
CPC ............ G01N 2035/00742; G01N 2035/1013; G01N 2035/1025; G01N 33/4905; G01N 35/026; G01N 35/1011; G01N 35/1079
USPC ....................................................... 422/50, 65
See application file for complete search history.

(56) References Cited

U.S. PATENT DOCUMENTS

| 5,985,215 A | 11/1999 | Sakazume et al. |
| 7,132,082 B2 * | 11/2006 | Aviles et al. .................. 422/562 |
| 2007/0134131 A1 * | 6/2007 | Watson et al. .................. 422/65 |

FOREIGN PATENT DOCUMENTS

JP 2001-264340 9/2001

* cited by examiner

*Primary Examiner* — Dean Kwak
(74) *Attorney, Agent, or Firm* — Brinks Gilson & Lione

(57) ABSTRACT

The present invention is to present a specimen processing apparatus, comprising: an imaging device for imaging a cap of a covered specimen container containing a specimen; an aspirating device including a specimen aspirating tube, moving the specimen aspirating tube so as to pass the specimen aspirating tube through the cap of the covered specimen container and aspirating the specimen contained in the covered specimen container via the specimen aspirating tube; an aspiration controller for controlling a movement of the specimen aspirating tube into the covered specimen container based on an image obtained by the imaging device; and a specimen processing device for processing the specimen aspirated by the aspirating device.

17 Claims, 43 Drawing Sheets

FIG.12

| CONTAINER TYPE ID | DESCENT AMOUNT |
|---|---|
| CAP001 | 100 |
| CAP002 | 95 |
| CAP003 | 105 |
| ⋮ | ⋮ |

TBL1

FIG.15

| CONTAINER TYPE ID | CONTAINER LENGTH | CAP LENGTH | CAP DIAMETER | SMALL DIAMETER SECTION LENGTH | SMALL DIAMETER SECTION DIAMETER | R,G,B |
|---|---|---|---|---|---|---|
| CAP001 | 70 | 9 | 15 | — | — | 115,50,155 |
| CAP002 | 85 | 23 | 13 | 15 | 8 | 255,20,60 |
| CAP003 | 75 | 12 | 15 | — | — | 10,140,250 |
| . . . | . . . | . . . | . . . | . . . | . . . | . . . |

TBL3

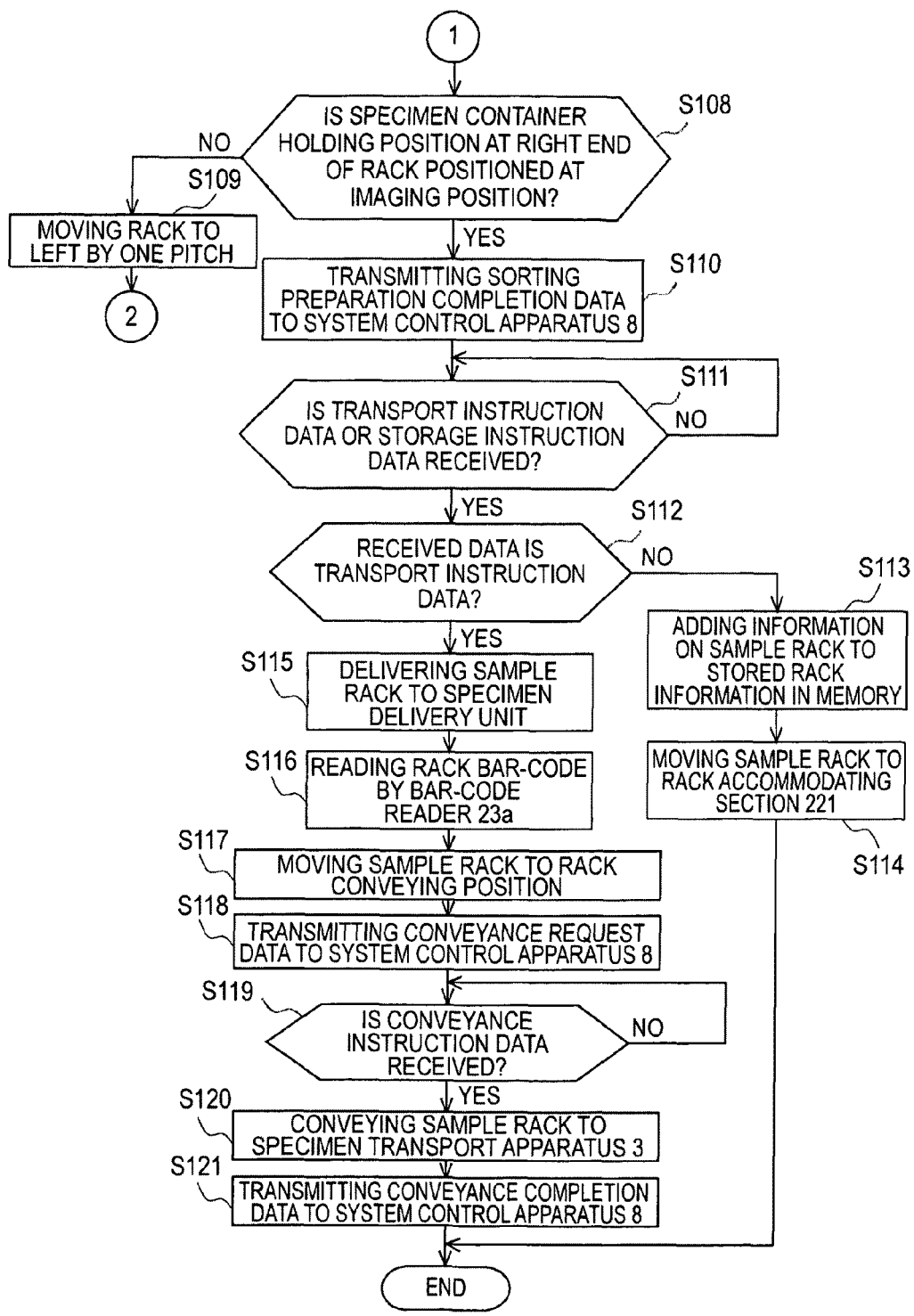

FIG.22

[SYSTEM CONTROL APPARATUS]

START

↓

RECEIVING RACK ID AND SPECIMEN IDS — S201

↓

S202 — IS SPECIMEN ID READING FAILURE DATA INCLUDED IN RECEIVED DATA?

— YES → ASSOCIATING SPECIMEN BAR-CODE READING ERROR INFORMATION WITH RACK ID AND HOLDING POSITION AND STORING SPECIMEN BAR-CODE READING ERROR INFORMATION — S203

— NO ↓

REQUESTING MEASURING ORDER CORRESPONDING TO ONE SPECIMEN ID — S204

↓

RECEIVING MEASURING ORDER? — S205

— RECEPTION FAILURE → ASSOCIATING MEASURING ORDER OBTAINING ERROR INFORMATION WITH RACK ID, SPECIMEN ID AND HOLDING POSITION AND STORING MEASURING ORDER OBTAINING ERROR INFORMATION — S207

— SUCCESSFUL RECEPTION → ASSOCIATING MEASURING ORDER WITH RACK ID AND STORING MEASURING ORDER — S206

↓

IS INQUIRY OF MEASURING ORDER OF ALL OF SPECIMEN IDS COMPLETED? — S208

— NO → (loop back)
— YES → END

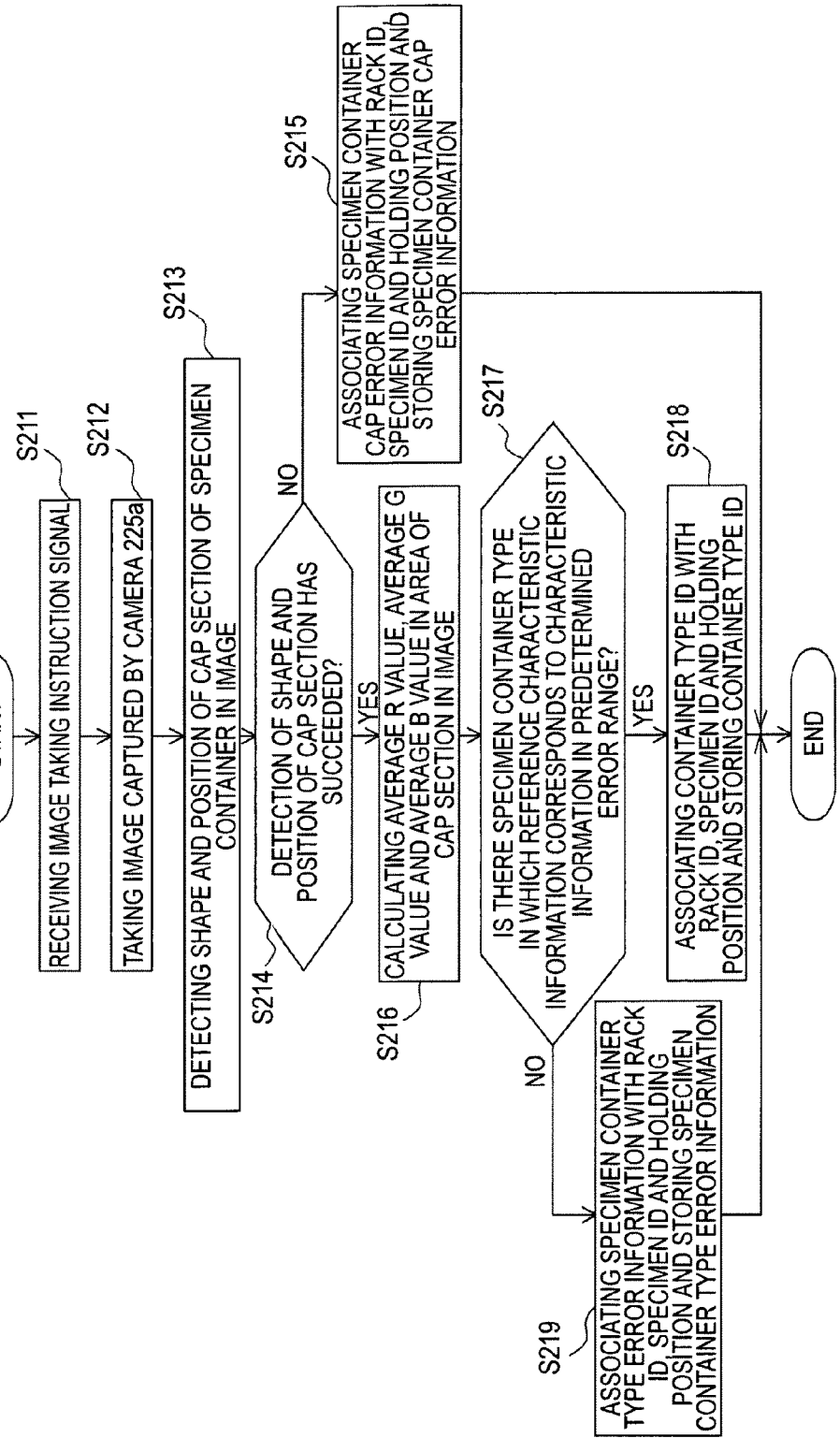

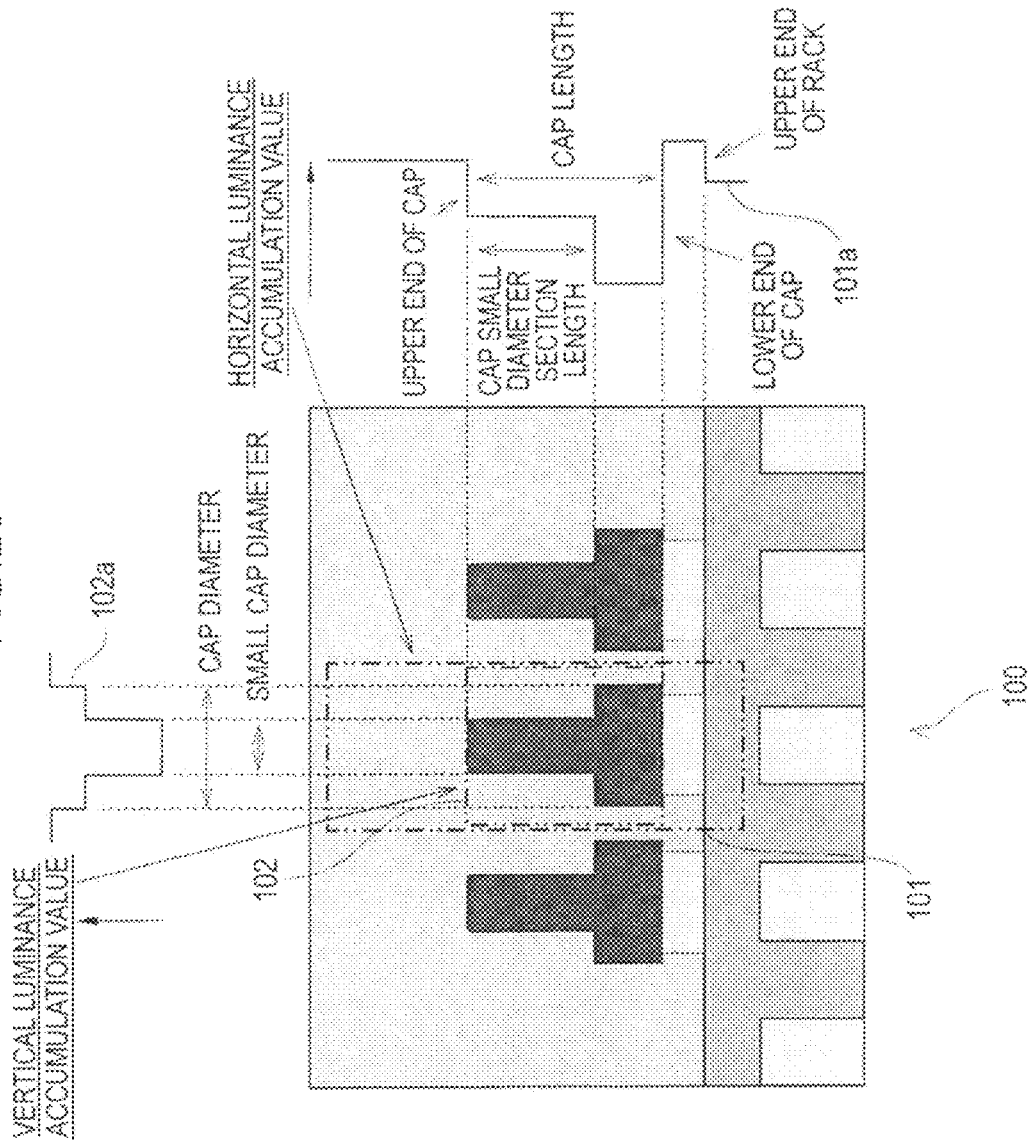

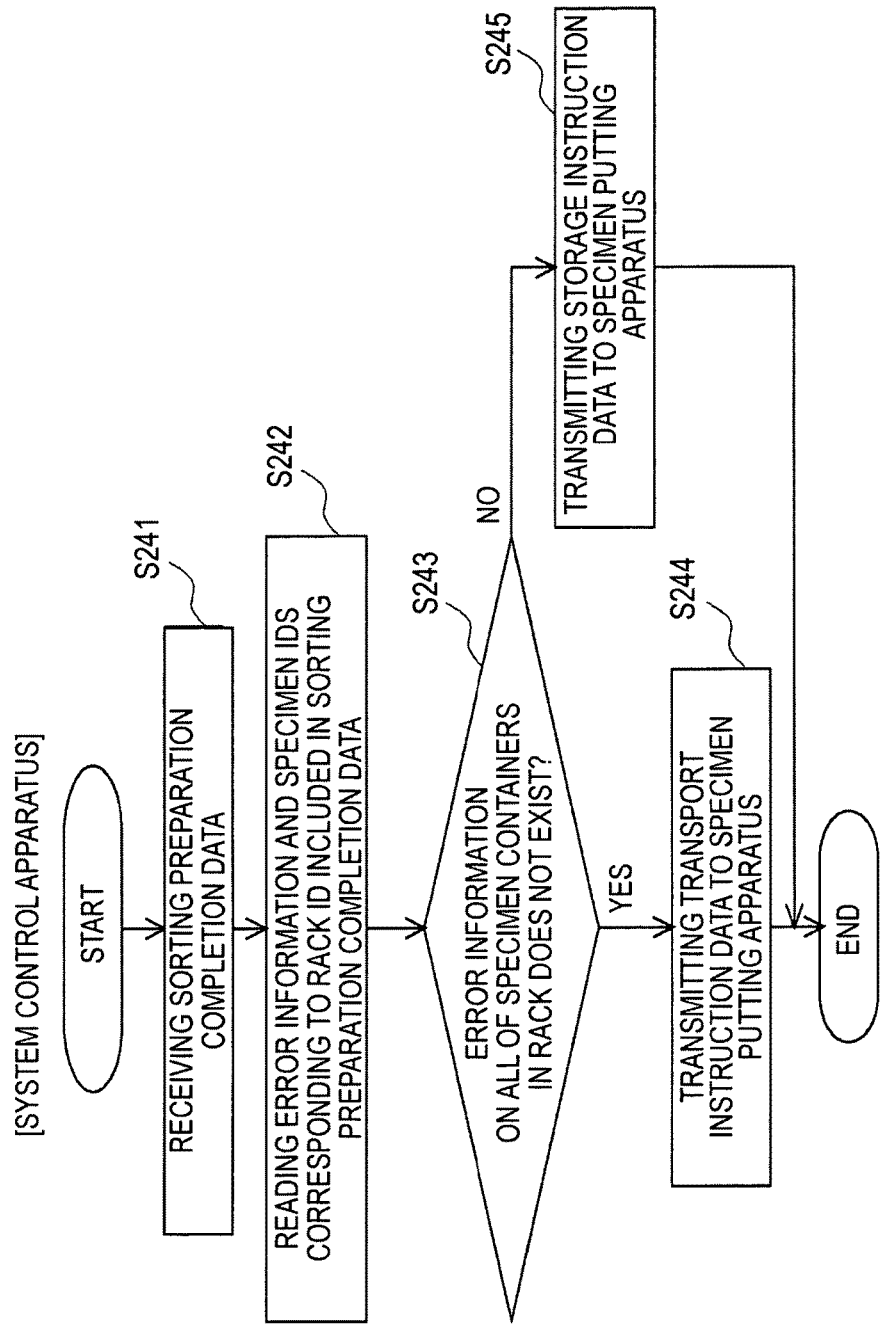

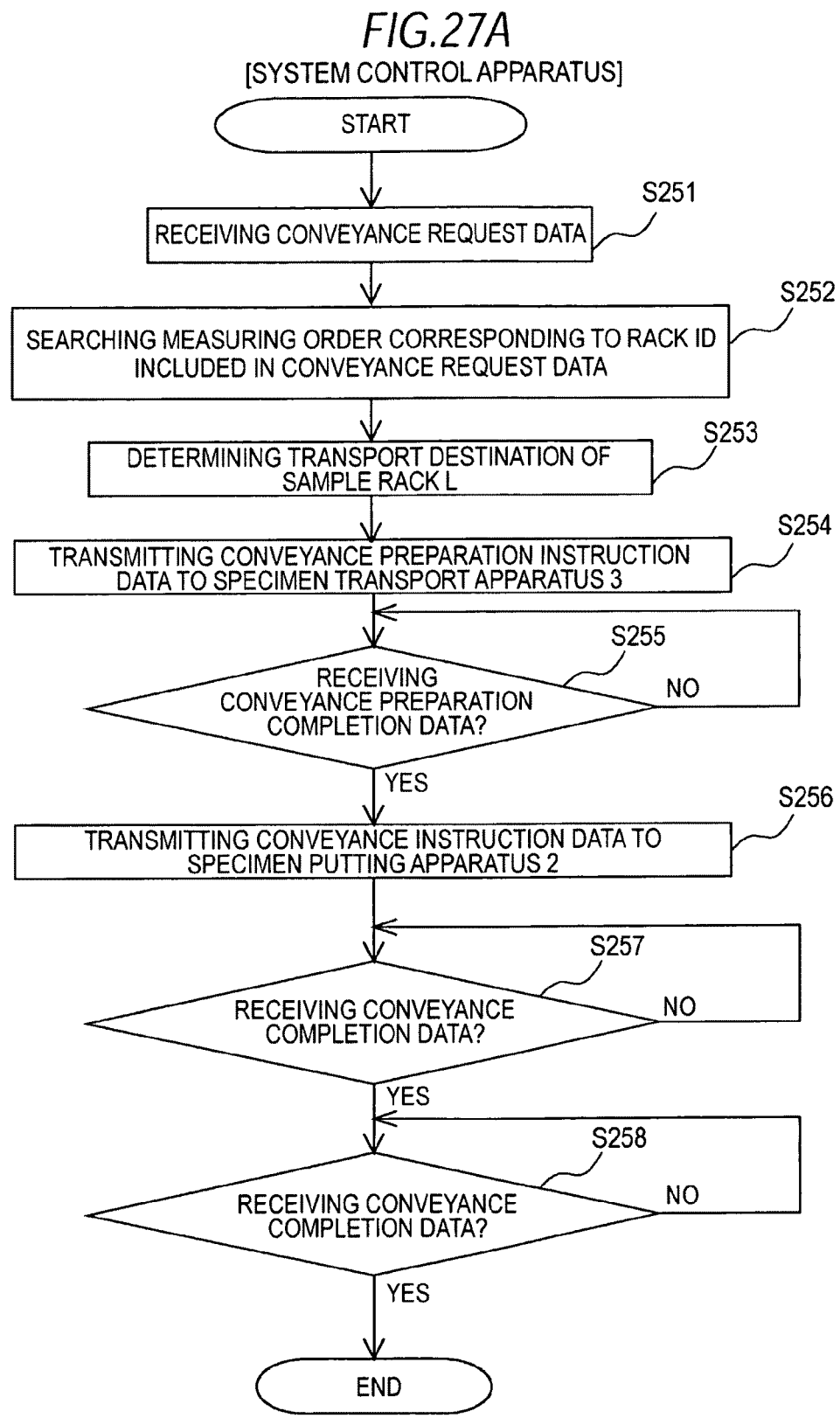

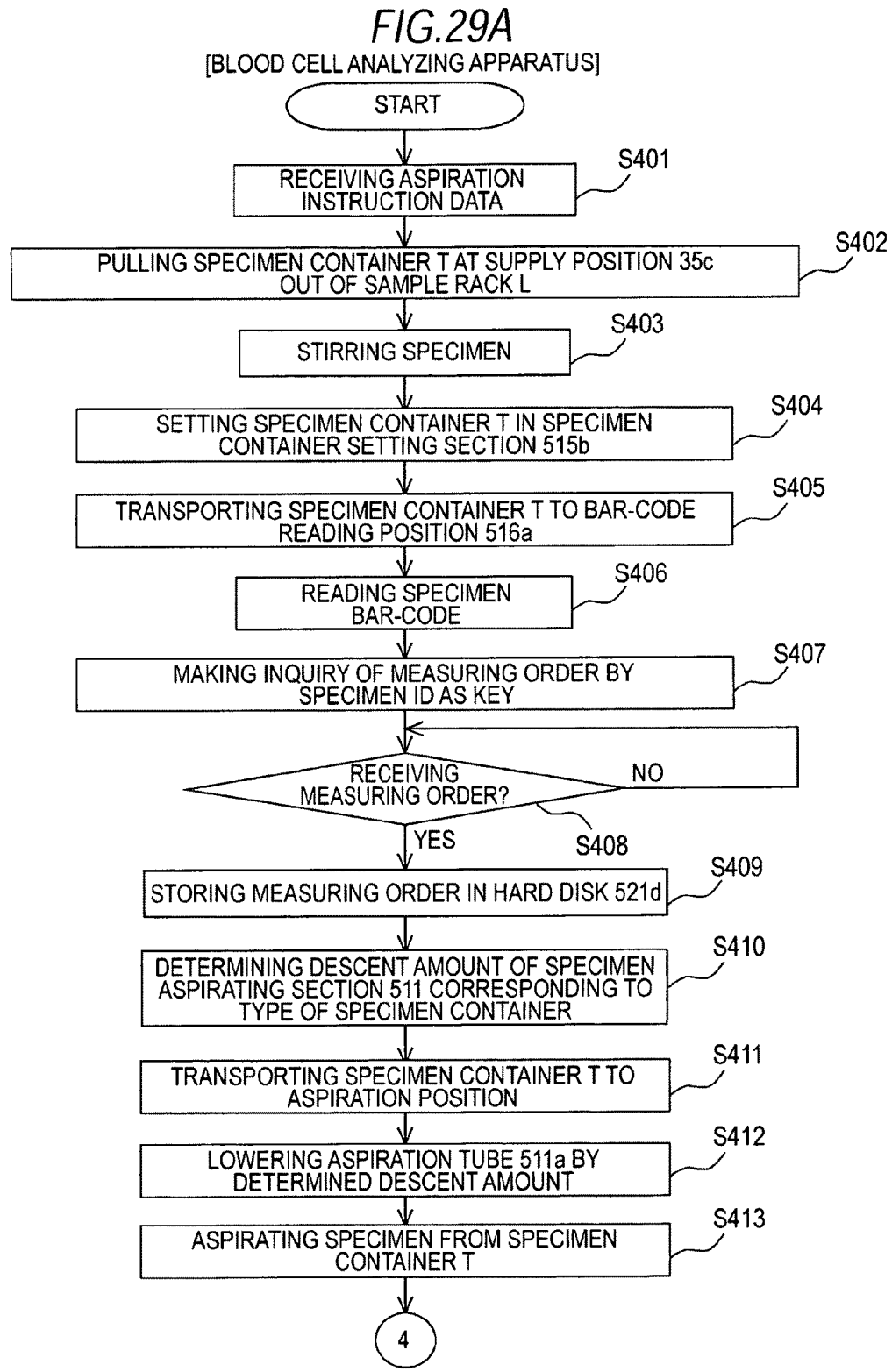

SPECIMEN PROCESSING APPARATUS

RELATED APPLICATIONS

This application claims priority under 35 U.S.C. §119 to Japanese Patent Application No. 2008-282055 filed on Oct. 31, 2008 and Japanese Patent Application No. 2009-155819 filed on Jun. 30, 2009, the entire content of which is hereby incorporated by reference.

FIELD OF THE INVENTION

The present invention relates to a specimen processing apparatus capable of processing a specimen which is aspirated by an aspirating device from an airtight container.

BACKGROUND

Conventionally, for example, Japanese Patent Publication No. 2001-264340 discloses a specimen processing apparatus for passing an aspiration tube through a cap for sealing a specimen container so as to aspirate a specimen from the specimen container and process the aspirated specimen. There are plural specimen containers with different dimensions and shapes which can be used in the specimen processing apparatus. For example, there are specimen containers of different cap thicknesses, specimen containers with different distances from an opening at the upper end thereof to an inner bottom surface, and the like. Accordingly, it is demanded to be able to perform a proper specimen aspirating operation according to specimen containers even when such different specimen containers are used together.

Japanese Patent Publication No. 2001-264340 discloses a specimen analyzing apparatus for jabbing an aspiration tube into an airtight container so as to aspirate blood and analyze the aspirated blood. In the specimen analyzing apparatus, a bar-code including specimen discriminating information and container type information is adhered to a side face of the airtight container, and a movement distance of the aspiration tube in accordance with the type of the specimen container is determined on the basis of the container type information read by a bar-code reader.

However, in general, the type of the information recorded in the bar-code is determined in accordance with institutions such as inspection centers or hospitals where the specimen analyzing apparatuses are installed, and it is necessary to change a code scheme of the bar-code in the institutions in order to introduce the specimen analyzing apparatus described in the above Japanese Patent Publication No. 2001-264340. Such a change in the code scheme of the bar-code significantly affects other systems. For example, it is necessary to change other systems in the institutions so as to be suitable for the code scheme.

SUMMARY

A first aspect of the present invention is a specimen processing apparatus, comprising: an imaging device for imaging a cap of a covered specimen container containing a specimen; an aspirating device including a specimen aspirating tube, moving the specimen aspirating tube so as to pass the specimen aspirating tube through the cap of the covered specimen container and aspirating the specimen contained in the covered specimen container via the specimen aspirating tube; an aspiration controller for controlling a movement of the specimen aspirating tube into the covered specimen container based on an image obtained by the imaging device; and a specimen processing device for processing the specimen aspirated by the aspirating device.

A second aspect of the present invention is a specimen processing apparatus, comprising: an imaging device for imaging a cap of a covered specimen container containing a specimen; an aspirating device including a specimen aspirating tube, moving the specimen aspirating tube so as to pass the specimen aspirating tube through the cap of the covered specimen container and aspirating the specimen contained in the covered specimen container via the specimen aspirating tube; a first controller for processing an image obtained by the imaging device; a second controller for controlling a movement of the specimen aspirating tube into the covered specimen container based on a processing result by the first controller; and a specimen processing device for processing the specimen aspirated by the aspirating device.

BRIEF DESCRIPTION OF THE DRAWINGS

FIG. 12 is a schematic diagram showing the structure of a descent amount table;

FIG. 15 is a schematic diagram showing the structure of a specimen container table;

FIG. 16B is a flowchart (second half) showing the flow of the specimen sorting operation of the specimen putting apparatus;

FIG. 22 is a flowchart showing the flow of a measuring order obtaining operation of the system control apparatus;

FIG. 24 is a flowchart showing the flow of a specimen container type discriminating process of the system control apparatus according to the first embodiment;

FIG. 25 is a schematic diagram for illustrating a process of detecting the shape and the position of a cap section of a specimen container in an image according to the first embodiment;

FIG. 26 is a flowchart showing the procedure of a sorting instruction process of the system control apparatus;

FIG. 27A is a flowchart showing the procedure of a first transport instruction process of the system control apparatus;

FIG. 29A is a flowchart (first half) showing the procedure of a specimen analyzing operation of a blood cell analyzing apparatus according to the first embodiment;

DETAILED DESCRIPTION OF THE PREFERRED EMBODIMENTS

Hereinafter, preferred embodiments of the invention will be described with reference to the drawings.

First Embodiment

This embodiment relates to a specimen processing apparatus which controls the aspiration of a specimen in a measuring unit on the basis of an image of a specimen container.

[Configuration of Specimen Processing System]

Figure 1:
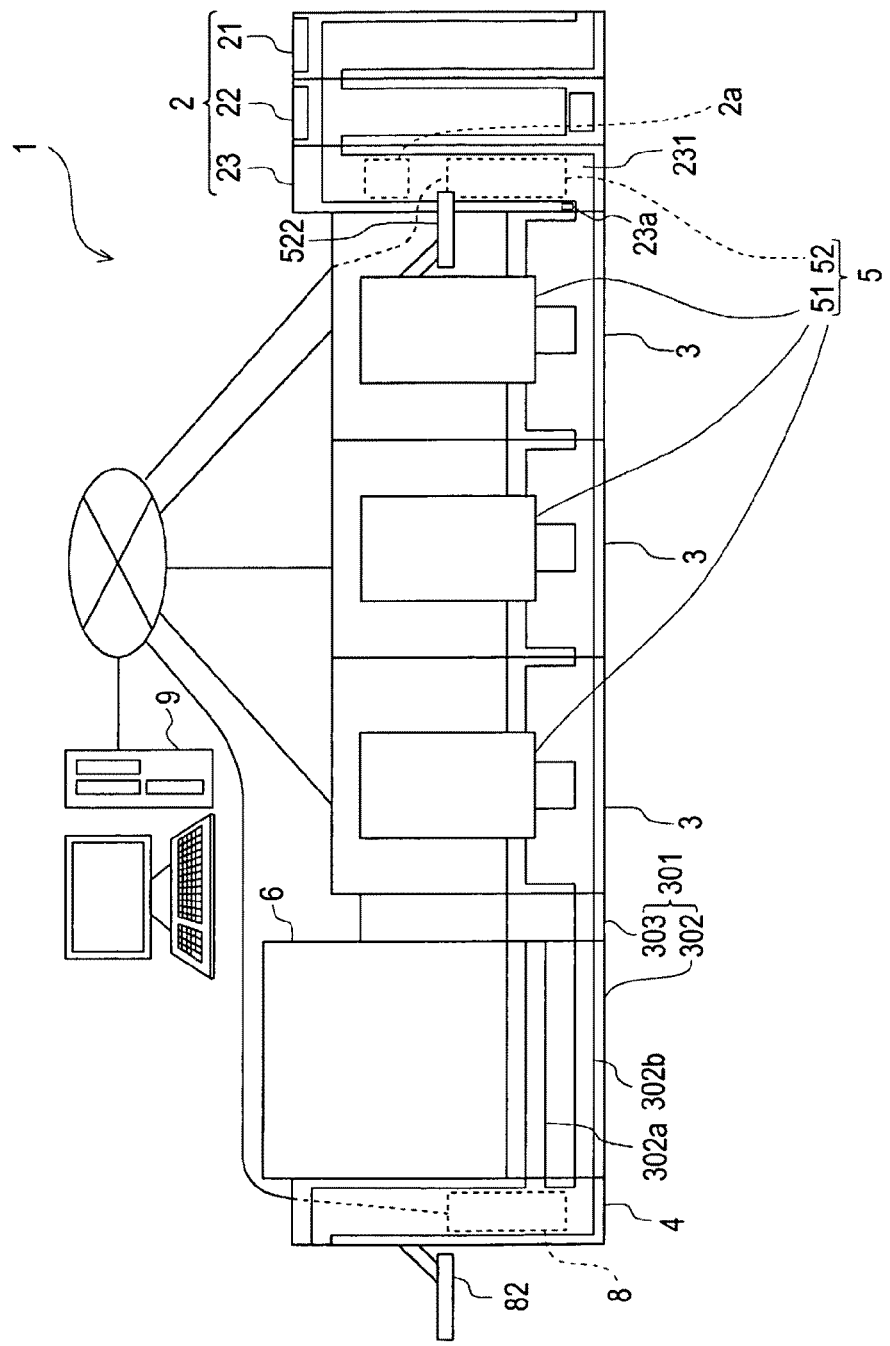
FIG. 1 is a schematic plan view showing the entire configuration of a specimen processing system according to a first embodiment.

FIG. 1 is a schematic plan view showing the entire configuration of a specimen processing system according to this embodiment. As shown in FIG. 1, a specimen processing system 1 includes a specimen putting apparatus 2, specimen transport apparatuses 3 and 301, a processed specimen accommodating apparatus 4, a blood cell analyzing apparatus 5, a smear preparing apparatus 6, and a system control apparatus 8. The specimen processing system 1 according to this embodiment is connected to a host computer 9 via a communication network so as to communicate therewith.

<Configuration of Specimen Putting Apparatus 2>

The specimen putting apparatus 2 includes a specimen putting unit 21, a specimen container accommodating unit 22 and a specimen delivery unit 23. The specimen putting apparatus 2 can place plural specimen containers accommodated in a sample rack. In addition, the specimen putting apparatus 2 includes a control section 2a composed of a CPU and a memory, and the control section 2a can control the operation mechanisms which are the specimen putting unit 21, the specimen container accommodating unit 22 and the specimen delivery unit 23. Moreover, the specimen putting apparatus 2 is connected to the system control apparatus 8 via a communication network so as to perform data communication with the system control apparatus 8.

Figure 2:
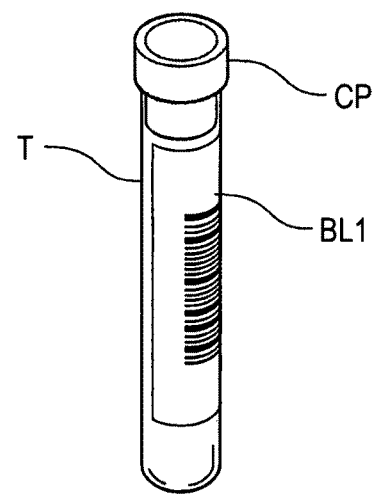
FIG. 2 is a perspective view showing the appearance of a specimen container.
Figure 3:
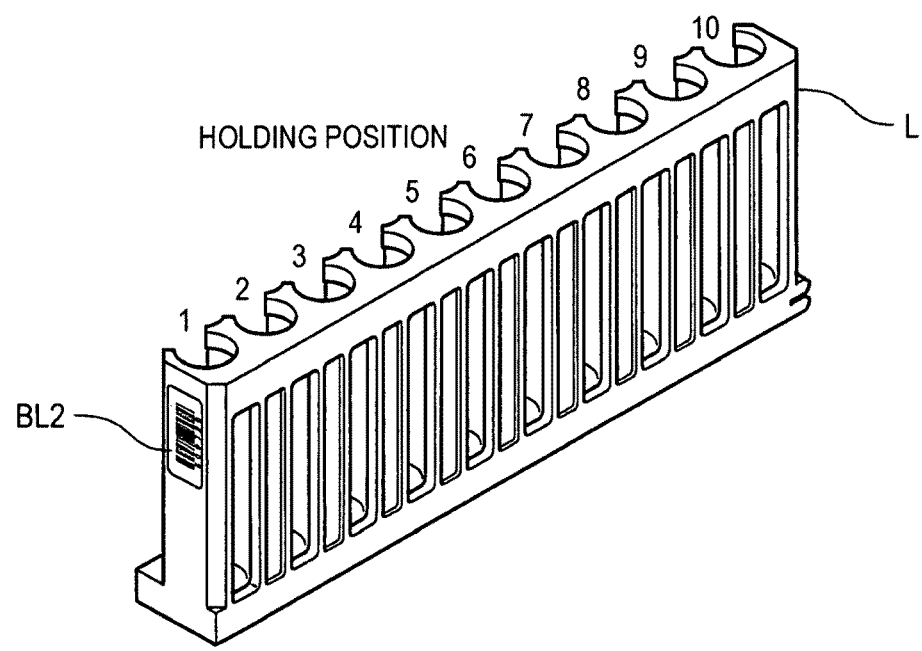
FIG. 3 is a perspective view showing the appearance of a sample rack.

FIG. 2 is a perspective view showing the appearance of a specimen container and FIG. 3 is a perspective view showing the appearance of a sample rack. As shown in FIG. 2, a tube-shaped specimen container T is open at an upper end thereof. The specimen container T contains a blood specimen collected from a patient and the opening at the upper end is sealed by a cap section CP. The specimen container T is made of translucent glass or synthetic resin, and the blood specimen therein can be visually confirmed. A bar-code label BL1 is adhered to a side face of the specimen container T and a bar-code indicating a specimen ID is printed on the bar-code label BL1. A sample rack L can hold ten specimen containers T arranged in order. In the sample rack L, the specimen containers T are held in a vertical state (erect state). A bar-code label BL2 is adhered to a side face of the sample rack L and a bar-code indicating a rack ID is printed on the bar-code label BL2.

Figure 4:
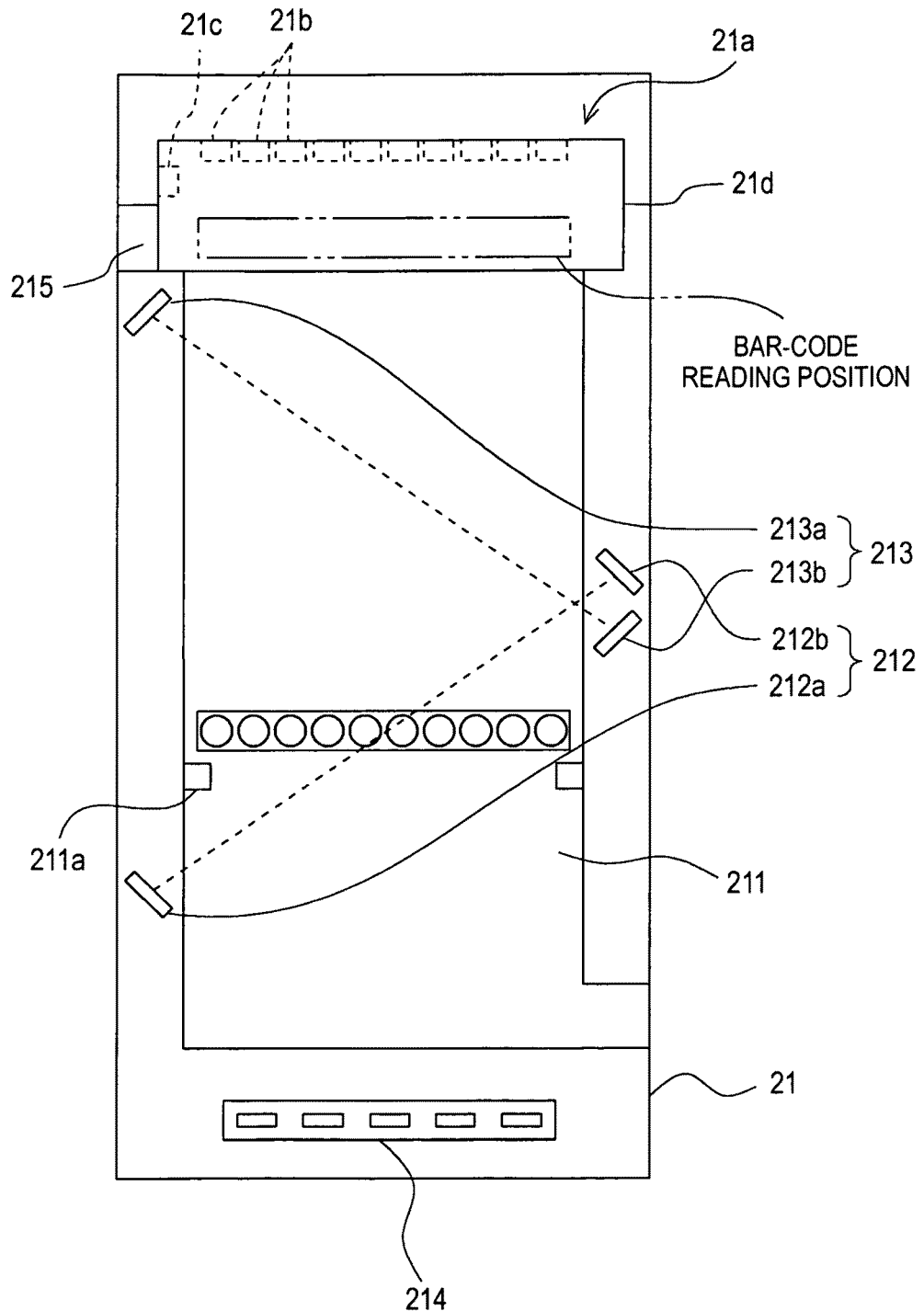
FIG. 4 is a plan view showing the configuration of a specimen putting unit.

FIG. 4 is a plan view showing the configuration of the specimen putting unit 21. As shown in FIG. 4, the specimen putting unit 21 has a concave rack placing section 211 for placing the sample rack L accommodating the specimen containers T. The rack placing section 211 has a rectangular shape and can simultaneously hold the plural sample racks L. The sample racks L are placed in the rack placing section 211 so that the specimen containers T line up in a transverse direction. The rack placing section 211 is provided with sensors 212 and 213 for detecting the sample rack L and an engaging section 211a for moving the sample rack L. The sensors 212 and 213 are optical sensors. The sensor 212 includes a light-emitting section 212a and a light-receiving section 212b, and the sensor 213 includes a light-emitting section 213a and a light-receiving section 213b. The light-emitting section 212a is positioned at the left-front side of the rack placing section 211 and the light-receiving section 212b is positioned at the right-center side of the rack placing section 211. In addition, the light-emitting section 213a is positioned at the left-rear side of the rack placing section 211 and the light-receiving section 213b is positioned at the right-center side of the rack placing section 211. The light-emitting section 212a is disposed so as to emit light diagonally in a backward right direction and the light-receiving section 212b is disposed so as to receive the light over the rack placing section 211. In addition, the light-emitting section 213a is disposed so as to emit light diagonally in a forward right direction and the light-receiving section 213b is disposed so as to receive the light over the rack placing section 211. Accordingly, by the sample rack L being placed in the rack placing section 211, the light emitted from the light-emitting section 212a or 213a is interrupted and thus there is a fall in the light-receiving level of the light-receiving section 212b or 213b. Therefore, the sample rack L is detected by the rack sensor 212 or 213. The sample rack L detected by the rack sensor 212 or 213 is engaged with the engaging section 211a and the engaging section 211a is moved in a front-back direction while being engaged with the sample rack L so as to move the sample rack L on the rack placing section 211.

The specimen putting unit 21 includes a bar-code reading section 21a at the inner side of the rack placing section 211. The bar-code reading section 21a includes a specimen bar-code reader 21b for simultaneously reading the specimen bar-codes of the plural specimen containers T accommodated in the sample rack L and a rack bar-code reader 21c for reading the rack bar-code of the sample rack L. Moreover, the bar-code reading section 21a includes a horizontal rotation mechanism 21d for simultaneous horizontal rotation of the plural specimen containers T directly above a bar-code reading position at the most inner side of the rack placing section 211. The sample rack L put into the rack placing section 211 is moved in a direction toward the inner side from the front side, that is, backward on the rack placing section 211, to reach the bar-code reading position. After that, while the specimen container T accommodated in the sample rack L is horizontally rotated by the horizontal rotation mechanism 21d, the specimen ID is read from the bar-code label BL1 by the specimen bar-code reader 21b. In addition, the rack ID is read from the bar-code label BL2 of the sample rack L by the rack bar-code reader 21c. The read rack ID and specimen ID are transmitted to the system control apparatus 8.

Further, the specimen putting unit 21 is disposed on the right side of the specimen container accommodating unit 22 (see FIG. 1 for reference). The sample rack L at the bar-code reading position, in which the rack bar-code and the specimen bar-code have been read, is conveyed to the specimen container accommodating unit 22 from a rack delivery port 215 provided on the left side of the bar-code reading position.

As shown in FIG. 4, the specimen putting unit 21 is provided with an operating panel 214. A user operates the operating panel 214 so as to issue an analysis start instruction or an analysis completion instruction to the specimen processing system 1.

Figure 5:
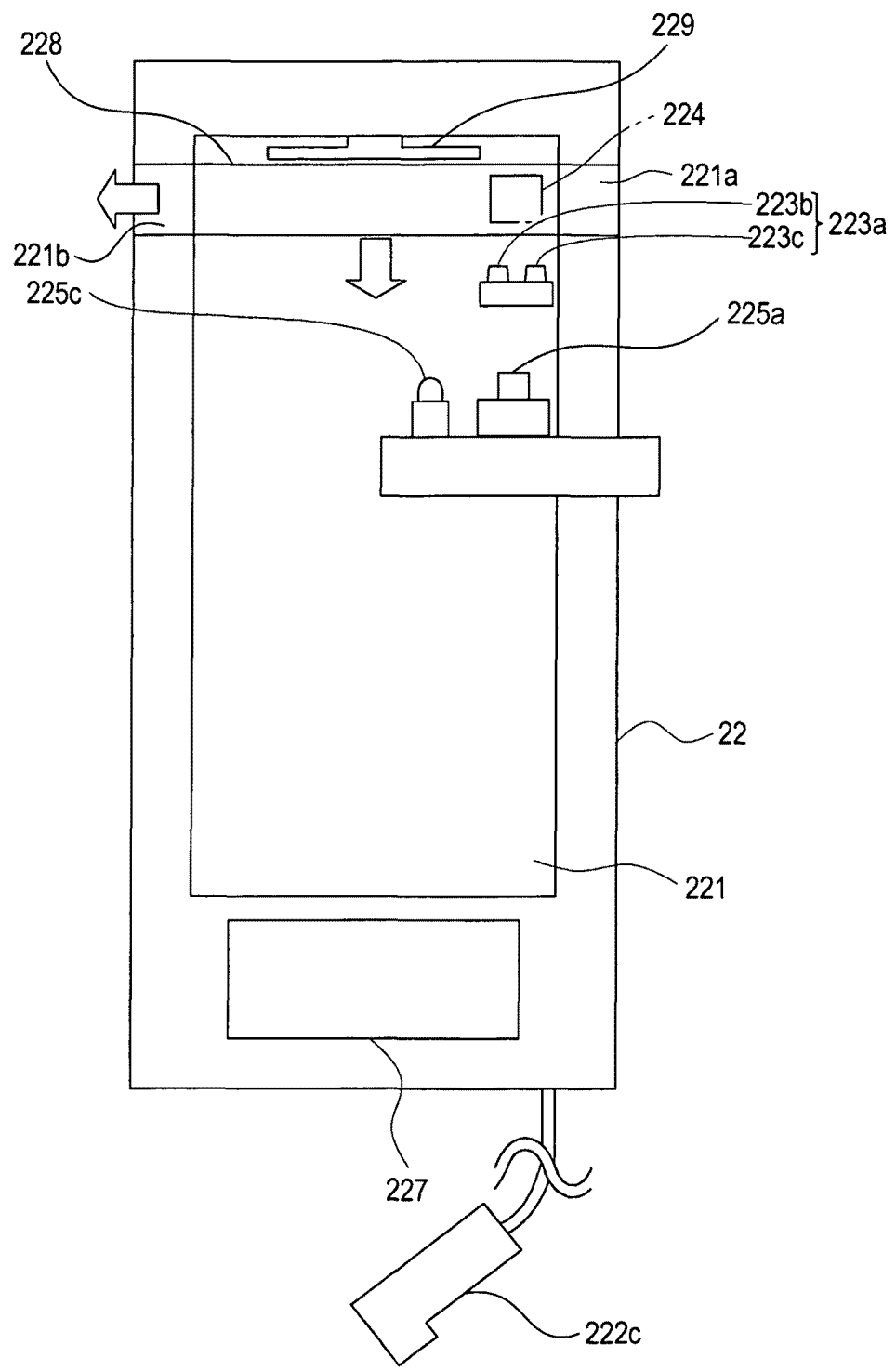
FIG. 5 is a plan view showing the configuration of a specimen container accommodating unit according to the first embodiment.

FIG. 5 is a plan view showing the configuration of the specimen container accommodating unit 22. As shown in FIG. 5, the specimen container accommodating unit 22 includes a rack accommodating section 221, which has a quadrangular shape when viewed from above, capable of accommodating the plural sample racks L. Further, the specimen container accommodating unit 22 includes a handy bar-code reader 222c which is manually operated by the user, an optical sensor 223a for detecting the presence or absence of the bar-code label BL1 of the specimen container T, a camera 225a for imaging the specimen container T and a liquid crystal display section 227.

The rack accommodating section 221 is a rectangular recessed portion when viewed from above. A rack feed port 221a for feeding the sample rack L from the specimen putting unit 21 is provided in a right wall section at the inner end of the rack accommodating section 221. In addition, a rack delivery port 221b for delivering the sample rack L to the specimen delivery unit 23 is provided in a left wall section at the inner end of the rack accommodating section 221. A transport belt 228 for transporting the sample rack L is provided between the rack feed port 221a and the rack delivery port 221b. The transport belt 228 is an annular belt and is driven by a stepping motor (not shown) so as to transport the sample rack L placed on the transport belt 228 to the left in the drawing. Moreover, a rack delivery section 229 is provided at the further inner side of the transport belt 228. The rack delivery section 229 is driven by a stepping motor (not shown) or the like so as to push forward the sample rack L on the transport belt 228. The sample rack L delivered to the front by the rack delivery section 229 is retained by the rack accommodating section 221.

By using the transport belt 228, the sample rack L is intermittently moved to the left in a pitch feeding manner in which the gap between the neighboring specimen containers T is set to one pitch. An imaging position 224 for capturing an image to judge the type of the specimen container T is provided on a transport path which is formed by the transport belt 228.

The specimen container T accommodated in the sample rack L reaches the imaging position 224 by moving the sample rack L to the left. The optical sensor 223a is disposed in front of the imaging position 224. The optical sensor 223a is composed of a light-emitting element 223b and a light-receiving element 223c. When the specimen container T reaches the imaging position 224, the specimen container T is irradiated with light by the light-emitting element 223b. This light is reflected by the specimen container T and the reflected light is received by the light-receiving element 223c. On the other hand, when the specimen container T is not positioned at the imaging position 224, the light of the light-emitting element 223b is not reflected and the reflected light is not received by the light-receiving element 223c. Accordingly, the light-receiving level of the light-receiving element 223c when the specimen container T is positioned at the imaging position is higher than that in the case in which the specimen container T is not positioned at the imaging position. From the difference in the light-receiving level, the presence or absence of the specimen container T at the imaging position 224 is determined.

The camera 225a is disposed in front of the specimen container T positioned at the imaging position 224. The camera 225a is disposed so that the cap section CP of the specimen container T positioned at the imaging position 224 is in the imaging range. A white LED 225c is disposed at a predetermined position with respect to the camera 225a and the specimen container T is illuminated by the white LED 225c.

Figure 6:
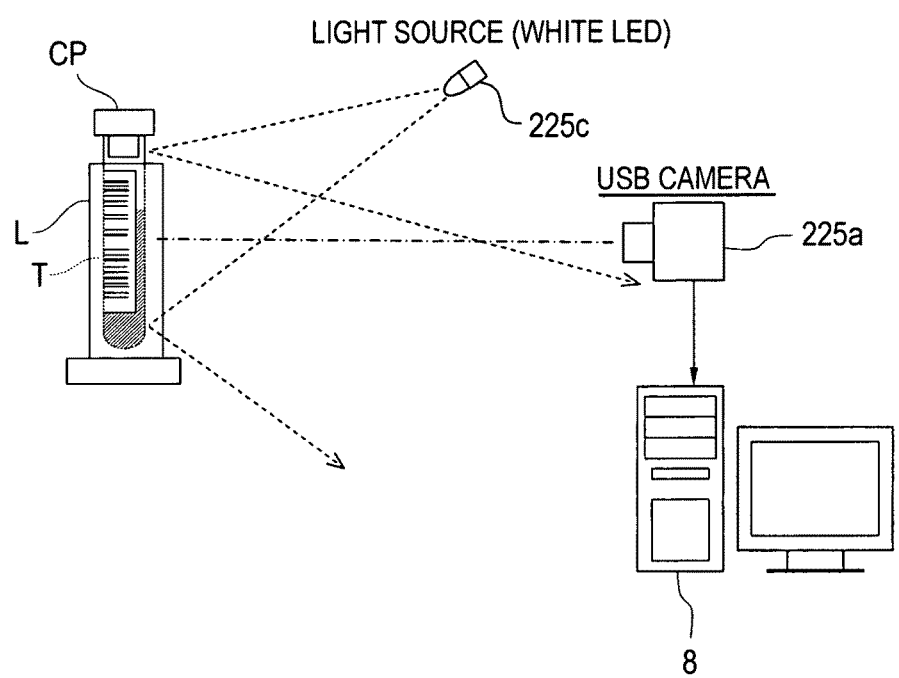
FIG. 6 is a schematic diagram for illustrating the positional relationship between a camera, a white LED and a specimen container in the specimen container accommodating unit according to the first embodiment, and the direction of the light emitted from the white LED.

FIG. 6 is a schematic diagram for illustrating the positional relationship between the camera 225a, the white LED 225c and the specimen container T, and the direction of the light emitted from the white LED. As shown in FIG. 6, the white LED 225c is disposed so that light is emitted toward the specimen container T positioned at the imaging position 224 and the light reflected from the specimen container T does not directly enter the camera 225a positioned in front of the specimen container T. Accordingly, the camera 225a is not directly exposed to the reflected light and so-called halation due to overexposure can be prevented.

The specimen container T held in the sample rack L at the imaging position 224 is imaged by the camera 225a, and the image data obtained in this manner is transmitted to the system control apparatus 8. The sample rack L in which the imaging of all the specimen containers T has been completed is delivered from the rack delivery port 221b by the transport belt 228.

The optical sensor 223a, the camera 225a and the white LED 225c can be vertically moved by a vertical driving mechanism (not shown). When the sample rack L is on the transport path of the rack accommodating section 221, the optical sensor 223a, the camera 225a and the white LED 225c are disposed in front of the sample rack L. When the sample rack L is moved to the front side of the rack accommodating section 221, the optical sensor 223a is lifted by the vertical driving mechanism up to a position which does not interfere with the movement of the sample rack L.

The bar-code reader 222c includes a light-emitting section and a light-receiving section (line sensor) (not shown), and is connected to a main body of the specimen container accommodating unit 22 by a flexible cable for transmitting an electric signal. The bar-code reader 222c is used when the user manually re-reads a bar-code which cannot be read by a bar-code reader 222b.

The specimen delivery unit 23 disposed on the left side of the specimen container accommodating unit 22 includes a rack re-putting section 231 in which the plural sample racks L are placed (see FIG. 1 for reference). The rack re-putting section 231 has the same rectangular parallelepiped shape as the rack placing section 211 of the specimen putting unit 21 when viewed from above. There is no right wall section at the inner side of the rack re-putting section 231 and this forms a rack feed port. The sample rack L is fed from the specimen container accommodating unit 22, through the rack feed port, to the specimen delivery unit 23. In addition, there is also no left wall section at the front side (front-face side) of the rack re-putting section 231 of the specimen delivery unit 23 and this portion serves as a rack delivery port. The sample rack L fed from the rack feed port is moved to the front by the rack re-putting section 231 so as to reach the most forward position and is then delivered to the left from the rack delivery port. Moreover, the specimen delivery unit 23 is provided with a bar-code reader 23a for reading a rack bar-code. By using the bar-code reader, the rack ID of the sample rack L transported to the rack re-putting section 231 is read, and before the sample rack L is transported to the following specimen transport apparatus 3, convey request data including the rack ID is transmitted to the system control apparatus 8.

<Configuration of Specimen Transport Apparatus 3>

Next, the configuration of the specimen transport apparatus 3 will be described. As shown in FIG. 1, the specimen processing system 1 includes three specimen transport apparatuses 3. The specimen transport apparatuses 3, 3 and 3 are each disposed in front of three measuring units 51, 51 and 51 of the blood cell analyzing apparatus 5. Neighboring specimen transport apparatuses 3 and 3 are connected to each other so as to send and receive the sample rack L to and from each other. The rightmost specimen transport apparatus 3 is connected to the above-described specimen putting apparatus 2 so as to feed the sample rack L conveyed from the specimen putting apparatus 2 thereto. The leftmost specimen transport apparatus 3 is connected to the specimen transport apparatus 301 so as to convey the sample rack L to the specimen transport apparatus 301.

Figure 7:
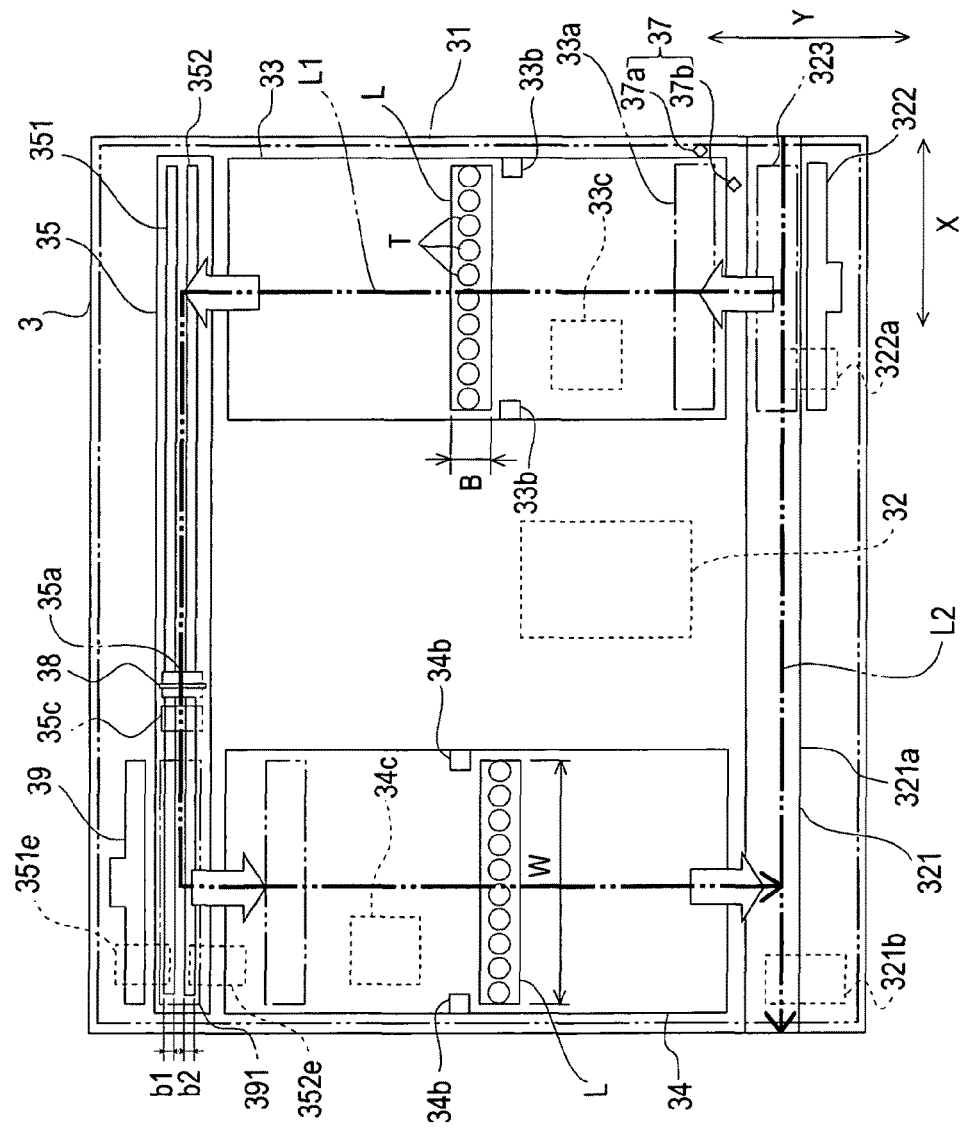
FIG. 7 is a plan view showing the configuration of a specimen transport apparatus.

FIG. 7 is a plan view showing the configuration of the specimen transport apparatus 3. As shown in FIG. 7, the specimen transport apparatus 3 includes a transport mechanism 31 for transporting a specimen and a control section 32 for controlling the transport mechanism 31. The transport mechanism 31 includes a before-analysis rack holding section 33 capable of temporarily holding the plural sample racks L holding the specimen containers T accommodating the specimens before the analysis is performed, an after-analysis rack holding section 34 capable of temporarily holding the plural sample racks L holding the specimen containers T in which the specimen is aspirated by the measuring unit 51, a rack transport section 35 for horizontally moving the sample rack L in a straight line in a direction of the arrow X in the drawing so as to supply the specimen to the measuring unit 51 and transporting the sample rack L received from the before-analysis rack holding section 33 to the after-analysis rack holding section 34, and a rack transport section 321 for conveying the sample rack L from the apparatus (specimen putting apparatus 2 or specimen transport apparatus 3) on the upstream side of the transport and conveying the sample rack L to the apparatus (specimen transport apparatus 3 or 301) on the downstream side of the transport without supplying the specimen accommodated in the sample rack L to the measuring unit 51.

The before-analysis rack holding section 33 has a quadrangular shape when viewed from above, and its width is slightly larger than the width of the sample rack L. The before-analysis rack holding section 33 is formed to be lower by one stage than the surrounding surface, and on an upper face thereof, the before-analysis sample racks L are placed. The before-analysis rack holding section 33 is connected to the rack transport section 321, and the sample rack L is sent from the rack transport section 321 by a rack delivery section 322 to be described later. A rack sensor 37 is installed near the before-analysis rack holding section 33, and a rack detection position 33a at which the sample rack L is detected by the rack sensor 37 is provided on the before-analysis rack holding section 33. The rack sensor 37 is an optical sensor and includes a light-emitting section 37a and a light-receiving section 37b. The light-emitting section 37a is provided lateral to the rack detection position 33a and the light-receiving section 37b is provided in front of the rack detection position 33a. The light-emitting section 37a is disposed so as to emit light diagonally in a forward direction and the light-receiving section 37b is disposed so as to receive the light. Accordingly, the sample rack L sent from the rack transport section 321 is positioned at the rack detection position 33a and the light emitted from the light-emitting section 37a is thus blocked by the sample rack L. Therefore, there is a fall in the light-receiving level of the light-receiving section 37b and the sample rack L is thus detected by the rack sensor 37. Further, rack sending sections 33b are provided in both faces of the before-analysis rack holding section 33 so as to be protruded inward. When the sample rack L is detected by the rack sensor 37, the rack sending sections 33b protrude so as to be engaged with the sample rack L. In this state, the rack sending sections 33b are moved backward (moved in a direction so as to be closer to the rack transport section 35) and thus the sample rack L is moved backward. The rack sending sections 33b are configured to be driven by a stepping motor 33c provided below the before-analysis rack holding section 33.

As shown in FIG. 7, the rack transport section 35 can move the sample rack L, which is moved by the before-analysis rack holding section 33, in the X direction. On the path of the transport of the sample rack L by the rack transport section 35, there are a specimen container detection position 35a where the specimen container is detected by a specimen container sensor 38 and a specimen supply position 35c for supplying the specimen to the measuring unit 51 of the blood cell analyzing apparatus 5. The rack transport section 35 is configured to transport the sample rack L via the specimen container detection position 35a so that the specimen is transported to the specimen supply position 35c. The specimen supply position 35c is positioned on the downstream side in the transport direction so as to be separated from the specimen container detection position 35a by a distance corresponding to one specimen. When the specimen is transported to the specimen supply position 35c by the rack transport section 35, a hand section of the measuring unit 51 of the blood cell analyzing apparatus 5 to be described later grasps the specimen container T of the specimen and takes out the specimen container T from the sample rack L so as to aspirate the specimen from the specimen container T, and thus the specimen is supplied to the measuring unit 51. After transporting the specimen container to the specimen supply position 35c, the rack transport section 35 stands by to transport the sample rack L while the supplying of the specimen is completed and the specimen container T is returned to the sample rack L.

Figure 8:
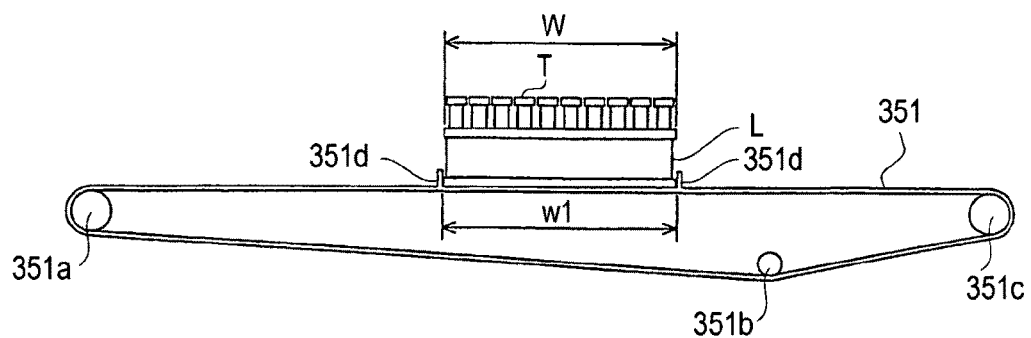
FIG. 8 is a front view showing the configuration of a first belt of the specimen transport apparatus.
Figure 9:
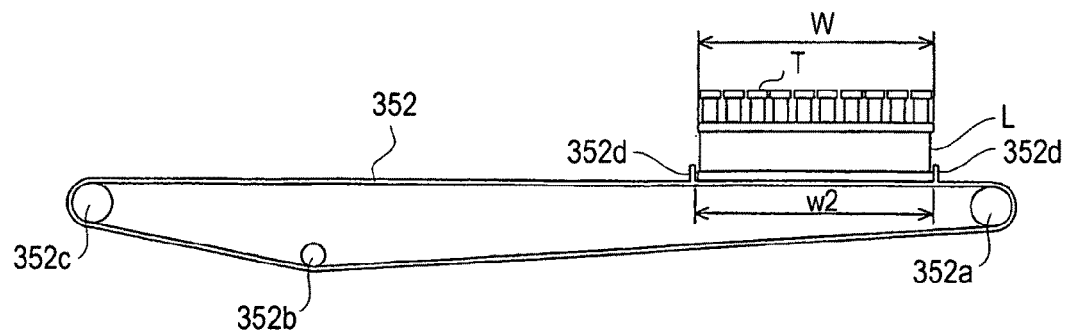
FIG. 9 is a front view showing the configuration of a second belt of the specimen transport apparatus.

In addition, the rack transport section 35 has two independently operable belts, that is, a first belt 351 and a second belt 352. Widths b1 and b2 in a direction of the arrow Y of the first belt 351 and the second belt 352 are equal to or smaller than half of a width B in the direction of the arrow Y of the sample rack L. The first belt 351 and the second belt 352 are disposed in parallel so as not to protrude from the width B of the sample rack L when the rack transport section 35 transports the sample rack L. FIG. 8 is a front view showing the configuration of the first belt 351 and FIG. 9 is a front view showing the configuration of the second belt 352. As shown in FIGS. 8 and 9, the first belt 351 and the second belt 352 are annularly formed respectively. The first belt 351 is disposed so as to surround rollers 351a to 351c and the second belt 352 is disposed so as to surround rollers 352a to 352c. In a peripheral section of the first belt 351, two protrusions 351d are provided so as to have an inner width w1 slightly larger (for example, 1 mm) than a width W in the X direction of the sample rack L, and similarly, in a peripheral section of the second belt 352, two protrusions 352d are provided so as to have nearly the same inner width w2 as the inner width w1. The first belt 351 is configured so that the sample rack L held inside of the two protrusions 351d is moved in the direction of the arrow X by being moved along the peripheries of the rollers 351a to 351c by a stepping motor 351e (see FIG. 7 for reference). The second belt 352 is configured so that the sample rack L held inside of the two protrusions 352d is moved in the direction of the arrow X by being moved along the peripheries of the rollers 352a to 352c by a stepping motor 352e (see FIG. 7 for reference). In addition, the first belt 351 and the second belt 352 are configured so as to move the sample rack L independently of each other.

The specimen container sensor 38 is a contact sensor and has a contact piece, a light-emitting element for emitting light and a light-receiving element (not shown). The specimen container sensor 38 is configured so that the contact piece is bent when brought into contact with a substance to be detected which is a detection object and the light emitted from the light-emitting element is thus reflected by the contact piece and enters the light-receiving element. Accordingly, while the specimen container T which is a detection object accommodated in the sample rack L passes under the specimen container sensor 38, the contact piece is bent by the specimen container T and the specimen container T can be detected.

A rack delivery section 39 is disposed so as to be opposed to the after-analysis rack holding section 34 to be described later with the rack transport section 35 interposed therebetween. The rack delivery section 39 is configured to be horizontally moved in a straight line in the direction of the arrow Y by a driving force of a stepping motor 39a. Accordingly, when the sample rack L is transported to a position 391 (hereinafter, referred to as "after-analysis rack delivery position") between the after-analysis rack holding section 34 and the rack delivery section 39, by moving the rack delivery section 39 toward the after-analysis rack holding section 34, the sample rack L is pushed so as to be moved to the inside of the after-analysis rack holding section 34. In this manner, the sample rack L in which the analysis has been completed is delivered to the after-analysis rack holding section 34 from the rack transport section 35.

The rack transport section 321 extends in the direction of the arrow X in the drawing and can horizontally move the sample rack L in a straight line in the direction of the arrow X. The rack transport section 321 has an annular belt 321a and a stepping motor 321b and is configured so as to rotate the belt 321a in the direction of the arrow X by a driving force of the stepping motor 321b. Accordingly, the sample rack L placed on the belt 321a can be moved in the X direction. In addition, the rack delivery section 322 is disposed in front of the before-analysis rack holding section 33 so as to be opposed to the before-analysis rack holding section 33 with the rack transport section 321 interposed therebetween. The rack delivery section 322 is configured to be horizontally moved in a straight line in the direction of the arrow Y by a driving force of a stepping motor 322a. Accordingly, when the sample rack L is transported to a position 323 (hereinafter, referred to as "before-analysis rack delivery position") between the before-analysis rack holding section 33 and the rack delivery section 322, by moving the rack delivery section 322 toward the before-analysis rack holding section 33, the sample rack L is pushed so as to be moved to the rack detection position 33a in the before-analysis rack holding section 33.

The after-analysis rack holding section 34 has a quadrangular shape when viewed from above, and its width is slightly larger than the width of the sample rack L. The after-analysis rack holding section 34 is formed to be lower by one stage than the surrounding surface, and on an upper face thereof, the sample racks L in which the analysis has been completed are placed. The after-analysis rack holding section 34 is connected to the rack transport section 35, and as described above, the sample rack L is sent from the rack transport section 35 by the rack delivery section 39. Rack sending sections 34b are provided in both faces of the after-analysis rack holding section 34 so as to protrude inward. When the sample rack L is conveyed by the rack delivery section 39, the rack sending sections 34b protrude so as to be engaged with the sample rack L. In this state, the rack sending sections are moved forward (moved in a direction so as to be closer to the rack transport section 321) and thus the sample rack L is moved forward. The rack sending sections 34b are configured to be driven by a stepping motor 34c provided below the after-analysis rack holding section 34.

Due to such a configuration, a measuring line L1, which is used as a transport line for the sample rack L passing through the specimen supply position 35c, and a skip line L2, which is used as a transport line for conveying the sample rack L not passing through the specimen supply position 35c to the apparatus on the downstream side, are formed in the transport mechanism 31.

The transport mechanism 31 having the above-described configuration is controlled by the control section 32. The control section 32 is composed of a CPU, a ROM, a RAM and the like (not shown) and a control program of the transport mechanism 31, which is stored in the ROM, can be executed by the CPU. The control section 32 includes an Ethernet (registered trade name) interface and is connected to an information processing unit 52 and the system control apparatus 8 via a LAN so as to communicate therewith.

Due to the above-described configuration, the specimen transport apparatus 3 transports the sample rack L, which is transported from the specimen putting apparatus 2, to the before-analysis rack delivery position 323 by using the rack transport section 321, moves the sample rack to the before-analysis rack holding section 33 by using the rack delivery section 322, delivers the sample rack L from the before-analysis rack holding section 33 to the rack transport section 35, and also transports the sample rack by using the rack transport section 35, and thus the specimen can be supplied to the measuring unit 51 of the blood cell analyzing apparatus 5. The sample rack L, which accommodates the specimens for which the aspiration has been completed, is moved to the after-analysis rack delivery position 391 by the rack transport section 35 and is delivered to the after-analysis rack holding section 34 by the rack delivery section 39. The sample rack L held in the after-analysis rack holding section 34 is moved to the rack transport section 321 and is conveyed to the following apparatus (specimen transport apparatus 3 or 301) by the rack transport section 321. When the sample rack L, which accommodates the specimens to be processed by the measuring unit 51 or the smear preparing apparatus 6 on the downstream side of the transport or the specimens in which the analysis has been completed, is received by the specimen transport apparatus 3 from the preceding apparatus, the sample rack L is transported in the direction of the arrow X by the rack transport section 321 and is conveyed to the following specimen transport apparatus 3.

<Configuration of Specimen Transport Apparatus 301>

As shown in FIG. 1, the specimen transport apparatus 301 is disposed in front of the smear preparing apparatus 6. The right end of the specimen transport apparatus 301 is connected to the specimen transport apparatus 3 positioned on the downmost-stream side of the transport (left side in the drawing) among the three specimen transport apparatuses 3, 3 and 3. The left end of the specimen transport apparatus 301 is connected to the processed specimen accommodating apparatus 4.

The specimen transport apparatus 301 includes a conveyor 302 and a rack slider 303. The conveyor 302 is provided with two rack transport paths 302a and 302b extending in a horizontal direction. The rack transport path 302a which is closer to the smear preparing apparatus 6 is a measuring line for transporting the sample rack L accommodating the specimen to be supplied to the smear preparing apparatus 6. The rack transport path 302b which is separated from the smear preparing apparatus 6 is a skip line for transporting the sample rack L not accommodating the specimen to be supplied to the smear preparing apparatus 6. The conveyor 302 includes a CPU, a memory and a control section (not shown) for controlling the operating mechanisms.

The rack slider 303 is disposed on the right side of the conveyor 302, and sorts and puts the sample racks L to the measuring line 302a and the skip line 302b of the conveyor 302.

<Configuration of Processed Specimen Accommodating Apparatus 4>

The processed specimen accommodating apparatus 4 is configured so as the plural sample racks L can be placed. The processed specimen accommodating apparatus 4 receives from the specimen transport apparatus 301 the sample rack L in which the analysis or the smear preparation has been completed, and accommodates the sample rack L.

<Configuration of Blood Cell Analyzing Apparatus 5>

The blood cell analyzing apparatus 5, which is used as an optical flow cytometry type multiple blood cell analyzing apparatus, obtains the fluorescent intensity, the side-scattered light intensity and the like of blood cells included in a blood specimen, classifies the blood cells included in the specimen on the basis of the above intensities, and counts the number of blood cells for each type. Moreover, the blood cell analyzing apparatus 5 creates a scattergram in which the classified blood cells are color-coded for each type, and displays the scattergram. The blood cell analyzing apparatus 5 includes the measuring units 51 for measuring a blood specimen and the information processing unit 52 for processing measuring data output from the measuring unit 51 and displaying analysis results of the blood specimen.

As shown in FIG. 1, the blood cell analyzing apparatus 5 includes the three measuring units 51, 51 and 51 and the one information processing unit 52. The information processing unit 52 is connected to the three measuring units 51, 51 and 51 so as to communicate therewith and can control the operations of the three measuring units 51, 51 and 51. The information processing unit 52 is also connected to the three specimen transport apparatuses 3, 3 and 3, which are respectively disposed in front of the three measuring units 51, 51 and 51, so as to communicate therewith.

Figure 10:
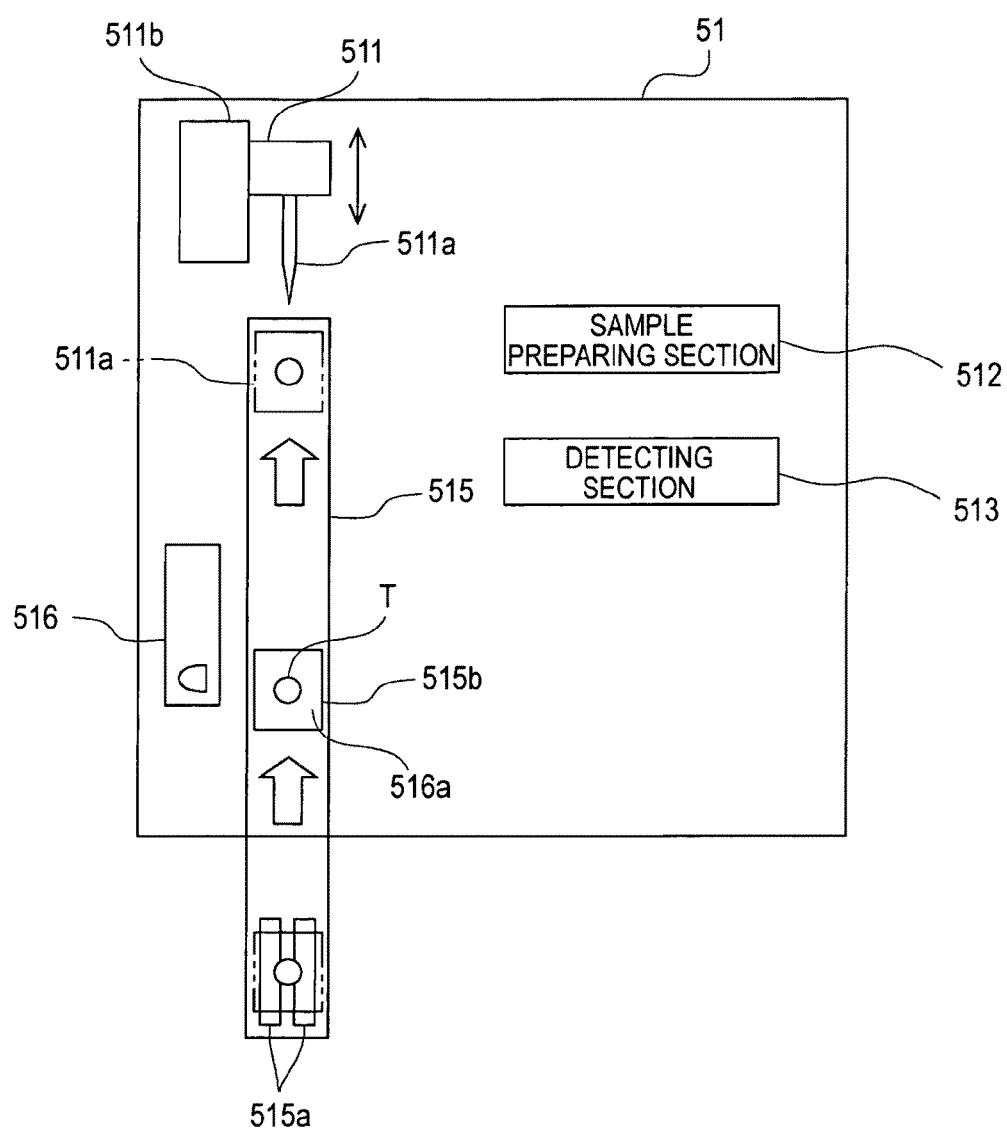
FIG. 10 is a block diagram showing the configuration of a measuring unit of a specimen analyzing apparatus.

The three measuring units 51, 51 and 51 have the same configuration. FIG. 10 is a block diagram showing the configuration of the measuring unit 51. As shown in FIG. 10, the measuring unit 51 includes a specimen aspirating section 511 for aspirating blood which is a specimen from the specimen container (blood collection tube) T, a sample preparing section 512 for preparing a measurement sample which is used in the measurement from the blood aspirated by the specimen aspirating section 511 and a detecting section 513 for detecting a blood cell from the measurement sample prepared by the sample preparing section 512. Moreover, the measuring unit 51 further has a taking port (not shown) for taking the specimen container T accommodated in the sample rack L transported by the rack transport section 35 of the specimen transport apparatus 3 into the measuring unit 51, and a specimen container transport section 515 for taking the specimen container T from the sample rack L into the measuring unit 51 and transporting the specimen container T to an aspiration position where the aspiration is performed by the specimen aspirating section 511.

An aspiration tube 511a is provided at the tip end of the specimen aspirating section 511. The specimen aspirating section 511 includes a driving mechanism 511b with a belt and a motor, and the aspiration tube 511a can be vertically moved by a driving force of the driving mechanism 511b. As described later, the aspiration tube 511a is configured to be moved downward by a descent amount which is determined in accordance with the type of a specimen container, so that the aspiration tube 511a penetrates into the cap section CP of the specimen container T transported to the aspiration position so as to aspirate the blood in the specimen container.

The aspiration tube 511a is formed of a pipe made of stainless steel and includes an aspiration flow path (not shown) at the center of the pipe. At the tip end of the aspiration tube 511a, a tapered, sharp pyramidal section having a trigonal pyramid shape is formed toward the apex. Accordingly, the descent force of the aspiration tube 511a is concentrated on the apex and thus the aspiration tube 511a can easily break through the cap section CP of the specimen container T.

Moreover, the aspiration tube 511a has, in its peripheral surface, three groove-like elongated concave sections which are parallel to a center axis and extend in a line. These concave sections are provided with predetermined intervals therebetween. When the aspiration tube 511a configured in this manner is lowered and the tip end of the aspiration tube penetrates into the cap section CP, the inside of the specimen container T is directly released to the open air by the concave sections of the peripheral surfaces of the aspiration tube 511a and the pressure in the specimen container T is thus returned to atmospheric pressure. Accordingly, the blood in the specimen container T is smoothly aspirated by the aspiration tube 511a and can be aspirated in certain quantities with high accuracy. The technique in which the inside of the specimen container T is released to the open air by the concave sections of the peripheral surface of the aspiration tube 511a is described in detail in JP-A-2004-170156.

The sample preparing section 512 includes plural reaction chambers (not shown). Further, the sample preparing section 512 is connected to a reagent container (not shown) and can supply reagents such as a smearing reagent, a hemolytic agent and a diluent to the reaction chamber. The sample preparing section 512 is also connected to the aspiration tube 511a of the specimen aspirating section 511 and can supply the blood specimen aspirated by the aspiration tube 511a to the reaction chamber. The sample preparing section 512 mixes and stirs the specimen and the reagent in the reaction chamber to prepare a sample (measurement sample) for the measurement by the detecting section 513.

The detecting section 513 can detect red blood cells (RBC) and platelets (PLT) by using a sheath flow DC detection method. In detecting RBCs and PLTs by using the sheath flow DC detection method, a measurement sample in which a specimen and a diluent are mixed is measured, and measuring data obtained in this manner is analyzed by the information processing unit 52 so as to measure the RBCs and PLTs. In addition, the detecting section 513 is configured to detect hemoglobin (HGB) by using a SLS-hemoglobin method and detect white blood cells (WBC), neutrophils (NEUT), lymphocytes (LYMPH), eosinophils (EO), basophil (BASO) and monocytes (MONO) by using a flow cytometry method using semiconductor lasers. In the detecting section 513, the detection of WBCs unaccompanied by 5 classifications of white blood cells, that is, the detection of WBCs unaccompanied by the detection of NEUTs, LYMPHs, EOs, BASOs and MONOs is different in detection method from the detection of WBCs accompanied by 5 classifications of white blood cells. In the detection of WBCs unaccompanied by 5 classifications of white blood cells, a measurement sample in which a specimen, a hemolytic agent and a diluent are mixed is measured, and measuring data obtained in this manner is analyzed by the information processing unit 52 so as to measure WBCs. In the detection of WBCs accompanied by 5 classifications of white blood cells, a measurement sample in which a smearing reagent, a hemolytic agent and a diluent are mixed is measured, and measuring data obtained in this manner is analyzed by the information processing unit 52 so as to measure NEUTs, LYMPHs, EOs, BASOs, MONOs and WBCs.

The specimen container transport section 515 includes a hand section 515a capable of grasping the specimen container T. The hand section 515a includes a pair of grasping members opposed to each other and can allow the grasping members to be closer to each other or farther from each other. The specimen container T can be held by allowing the grasping members with the specimen container T interposed therebetween to be closer to each other. Further, the specimen container transport section 515 can move the hand section 515a in a vertical direction and in a front-back direction (Y direction) and can oscillate the hand section 515a. Accordingly, by holding the specimen container T accommodated in the sample rack L and positioned at the supply position 35c with the hand section 515a and moving the hand section 515a upward, the specimen container T is pulled out of the sample rack L, and by oscillating the hand section 515a, the specimen in the specimen container T can be stirred.

In addition, the specimen container transport section 515 includes a specimen container setting section 515b having a hole to which the specimen container T can be inserted. The specimen container T grasped by the above-described hand section 515a is moved after the completion of stirring and the grasped specimen container T is inserted into the hole of the specimen container setting section 515b. Then, by allowing the grasping members to be separated from each other, the specimen container T is released from the hand section 515a and the specimen container T is set in the specimen container setting section 515b. The specimen container setting section 515b can be horizontally moved in the Y direction by the power of a stepping motor (not shown). A bar-code reading section 516 is provided in the measuring unit 51. The specimen container setting section 515b can be moved to a bar-code reading position 516a near the bar-code reading section 516 and an aspiration position 511a where the aspiration is performed by the specimen aspirating section 511. When the specimen container setting section 515b is moved to the bar-code reading position 516a, the set specimen container T is horizontally rotated by a rotation mechanism (not shown) and the specimen bar-code is read by the bar-code reading section 516. Accordingly, even when the bar-code label BL1 of the specimen container T is positioned on the opposite side with respect to the bar-code reading section 516, the bar-code label BL1 can face the bar-code reading section 516 by rotating the specimen container T and the bar-code reading section 516 can read the specimen bar-code. When the specimen container setting section 515b is moved to the aspiration position, the specimen is aspirated from the set specimen container T by the specimen aspirating section 511.

Figure 11:
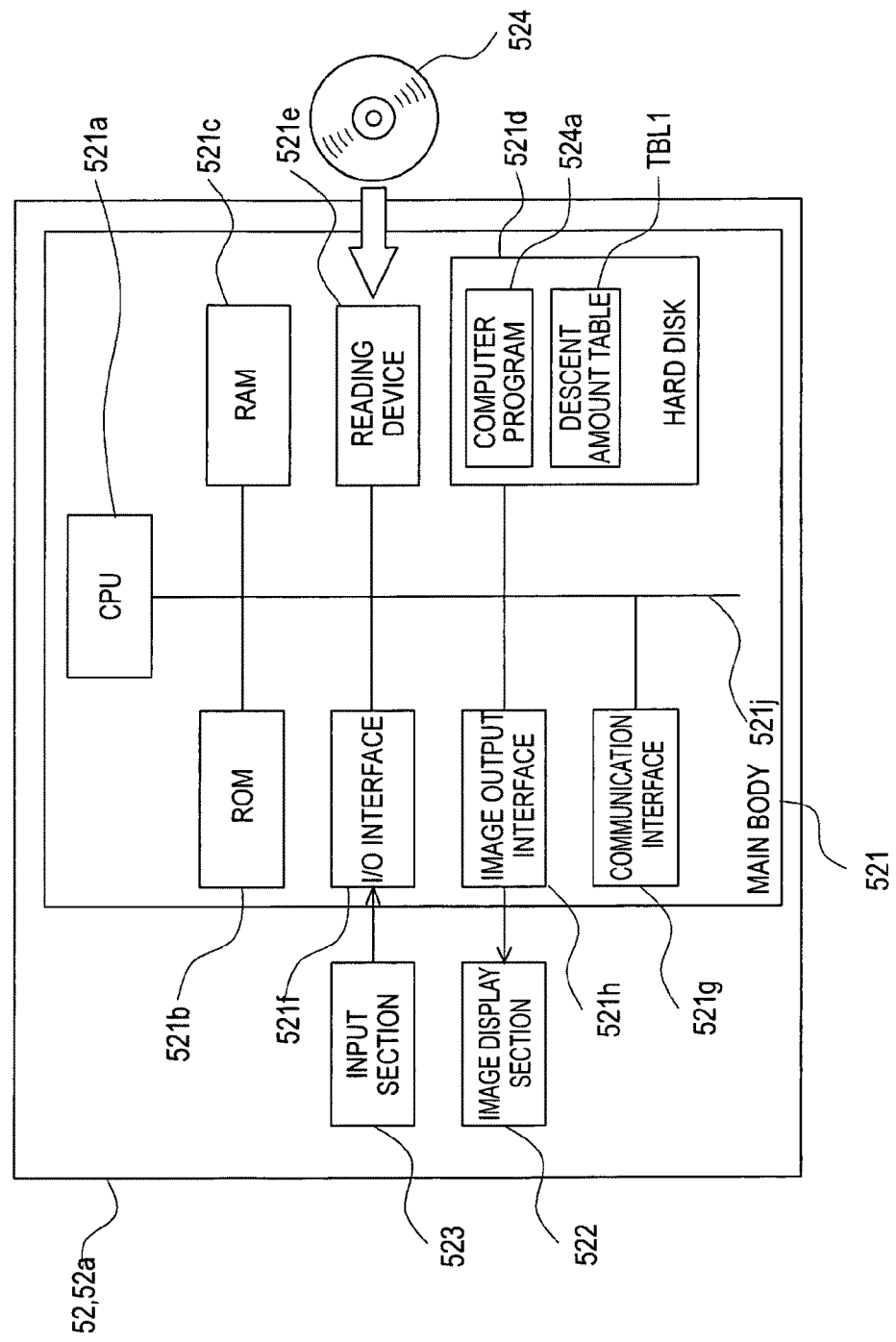
FIG. 11 is a block diagram showing the configuration of an information processing unit of the specimen analyzing apparatus.

Next, the configuration of the information processing unit 52 will be described. The information processing unit 52 is composed of a computer. FIG. 11 is a block diagram showing the configuration of the information processing unit 52. The information processing unit 52 is realized by a computer 52a. As shown in FIG. 11, the computer 52a includes a main body 521, an image display section 522 and an input section 523. The main body 521 includes a CPU 521a, a ROM 521b, a RAM 521c, a hard disk 521d, a reading device 521e, an I/O interface 521f, a communication interface 521g and an image output interface 521h. The CPU 521a, ROM 521b, RAM 521c, hard disk 521d, reading device 521e, I/O interface 521f, communication interface 521g and image output interface 521h are connected to each other by a bus 521j.

The CPU 521a can execute a computer program loaded to the RAM 521c. The CPU 521a executes a computer program 524a for analyzing a specimen and controlling the measuring unit 51, which will be described later, so that the computer 52a functions as the information processing unit 52.

The ROM 521b is composed of a mask ROM, a PROM, an EPROM, an EEPROM or the like and the computer program executed by the CPU 521a and data used for the computer program are recorded in the ROM.

The RAM 521c is composed of a SRAM, a DRAM or the like. The RAM 521c is used to read the computer program 524a recorded in the hard disk 521d. Moreover, the RAM is used as an operating area of the CPU 521a when the CPU 521a executes a computer program.

In the hard disk 521d, various computer programs for execution by the CPU 521a, such as an operating system and an application program, and data, which are used to execute the computer programs, are installed. The computer program 524a to be described later is also installed in the hard disk 521d.

The reading device 521e is composed of a flexible disk drive, a CD-ROM drive, a DVD-ROM drive or the like and can read the computer program or data recorded in a portable recording medium 524. In the portable recording medium 524, the computer program 524a for prompting the computer to function as the information processing unit 52 is stored. The computer 52a can read the computer program 524a from the portable recording medium 524 and install the computer program 524a in the hard disk 521d.

The computer program 524a is provided by the portable recording medium 524 and can be also provided from an external device, which is connected to the computer 52a by an electric communication line (which may be wired or wireless) to communicate therewith, through the electric communication line. For example, the computer program 524a is stored in a hard disk of a server computer on the internet and the computer 52a accesses the server computer to download the computer program and install the computer program in the hard disk 521d.

Furthermore, in the hard disk 521d, for example, a multitasking operating system such as Windows (registered trade name), which is made and distributed by Microsoft corporation in America, is installed. In the following description, the computer program 524a according to this embodiment operates on the above operating system.

Moreover, a descent amount table TBL1 which is used to determine a descent amount of the specimen aspirating section 511 is provided in the hard disk 521d. FIG. 12 is a schematic diagram showing the structure of the descent amount table TBL1. As shown in the drawing, the descent amount table TBL1 is data having a two-dimensional table form and each row corresponds to the type of a specimen container. Each row includes a container type ID for specifying the type of a specimen container and a descent amount of the specimen aspirating section 511 when the specimen is aspirated from this specimen container.

The I/O interface 521f is composed of, for example, a serial interface such as USB, IEEE1394 or RS-232C, a parallel interface such as SCSI, IDE or IEEE 1284, and an analog interface including a D/A converter and an A/D converter. The input section 523 composed of a keyboard and a mouse is connected to the I/O interface 521f and the user uses the input section 523 so as to input data to the computer 52a. In addition, the I/O interface 521f is connected to the three measuring units 51, 51 and 51 so as to send and receive data to and from the respective three measuring units 51, 51 and 51.

The communication interface 521g is an Ethernet (registered trade name) interface. The communication interface 521g is connected to the system control apparatus 8 via a LAN. Via the communication interface 521g, the computer 52a can send and receive data to and from the system control apparatus 8 connected to the LAN by using a predetermined communication protocol. In addition, the communication interface 521g is connected to the host computer 9 and each of the specimen transport apparatuses 3, 3, and 3 via the LAN so as to communicate therewith.

The image output interface 521h is connected to the image display section 522 composed of a LCD, a CRT or the like so as to output a picture signal corresponding to the image data provided from the CPU 521a to the image display section 522. The image display section 522 displays an image (screen) in accordance with an input picture signal.

<Configuration of Smear Preparing Apparatus 6>

The smear preparing apparatus 6 aspirates a blood specimen so as to deliver it onto a slide glass by drops, spreads and dries the blood specimen on the slide glass, and supplies a stain solution to the slide glass to stain the blood on the slide glass. In this manner, the smear preparing apparatus prepares a smear.

Figure 13:
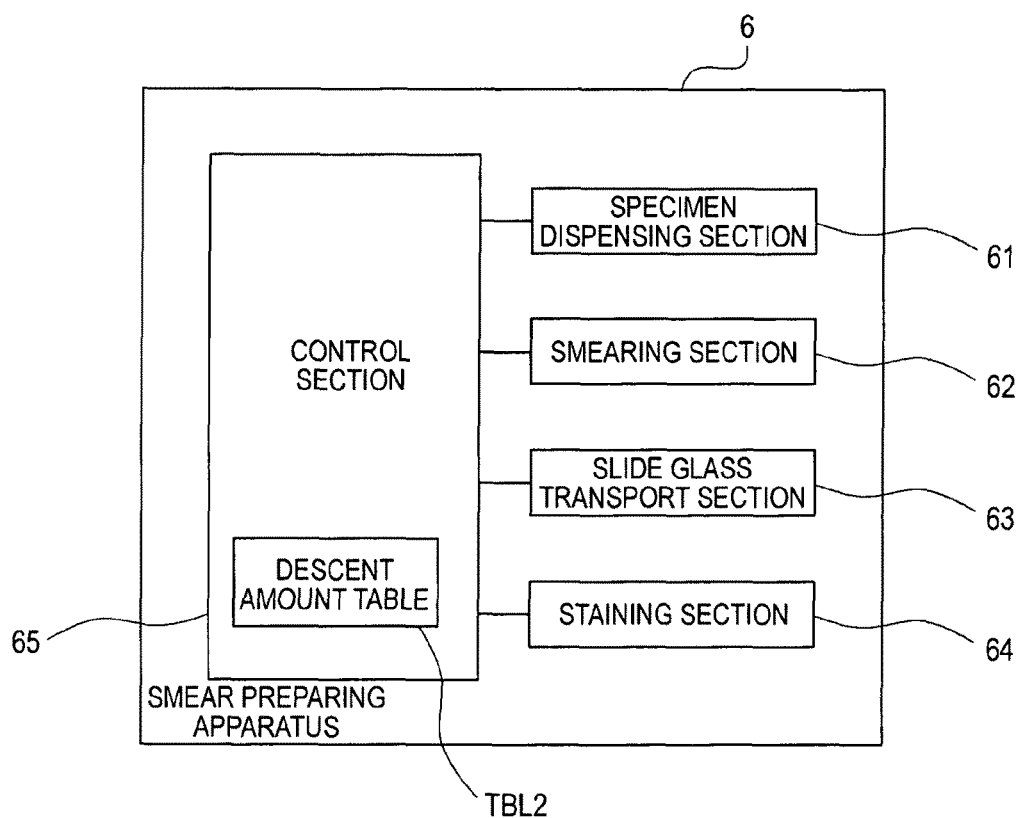
FIG. 13 is a block diagram showing the schematic configuration of a smear preparing apparatus.

FIG. 13 is a block diagram showing the schematic configuration of the smear preparing apparatus 6. As shown in FIG. 13, the smear preparing apparatus 6 includes a specimen dispensing section 61, a smearing section 62, a slide glass transport section 63, a staining section 64 and a control section 65.

The specimen dispensing section 61 includes an aspiration tube (not shown) and the aspiration tube is stuck in the cap section CP of a specimen container T in the sample rack L transported on a measuring line 31a of the specimen transport apparatus 3 so as to aspirate a blood specimen from the specimen container T. The specimen dispensing section 61 is configured to drop the aspirated blood specimen onto a slide glass. The smearing section 62 is configured to smear and dry the blood specimen dropped onto the slide glass and perform printing on the slide glass.

The slide glass transport section 63 is provided to accommodate the slide glass on which the blood specimen is smeared by the smearing section 62 in a cassette (not shown) and to transport the cassette. The staining section 64 supplies a stain solution to the slide glass in the cassette transported to a staining position by the slide glass transport section 63. The control section 65 controls the specimen dispensing section 61, the smearing section 62, the slide glass transport section 63 and the staining section 64 in accordance with a smear preparing instruction issued from the specimen transport apparatus 3 so as to perform the above smear preparing operation. The smear prepared in this manner is delivered to a blood cell image display apparatus 7.

The control section 65 includes a CPU and a memory. This memory includes a nonvolatile memory and a descent amount table TBL2 is stored in the nonvolatile memory. The descent amount table TBL2 is a two-dimensional table in which container type IDs correspond to descent amounts, as in the above-described descent amount table TBL1. However, in the blood cell analyzing apparatus 5 and the smear preparing apparatus 6, a descent amount of the aspiration tube varies even in the specimen containers of the same type. Thus, the descent amounts stored in the descent amount table TBL2 are descent amounts when the aspiration tube of the specimen dispensing section 61 is lowered and the tip end of the aspiration tube approaches near to the bottom surface of the specimen container T but is not brought into contact with the bottom surface of the specimen container T. In addition, the descent amounts stored in the descent amount table TBL2 are different from the descent amounts stored in the descent amount table TBL1.

<Configuration of System control Apparatus 8>

Figure 14:
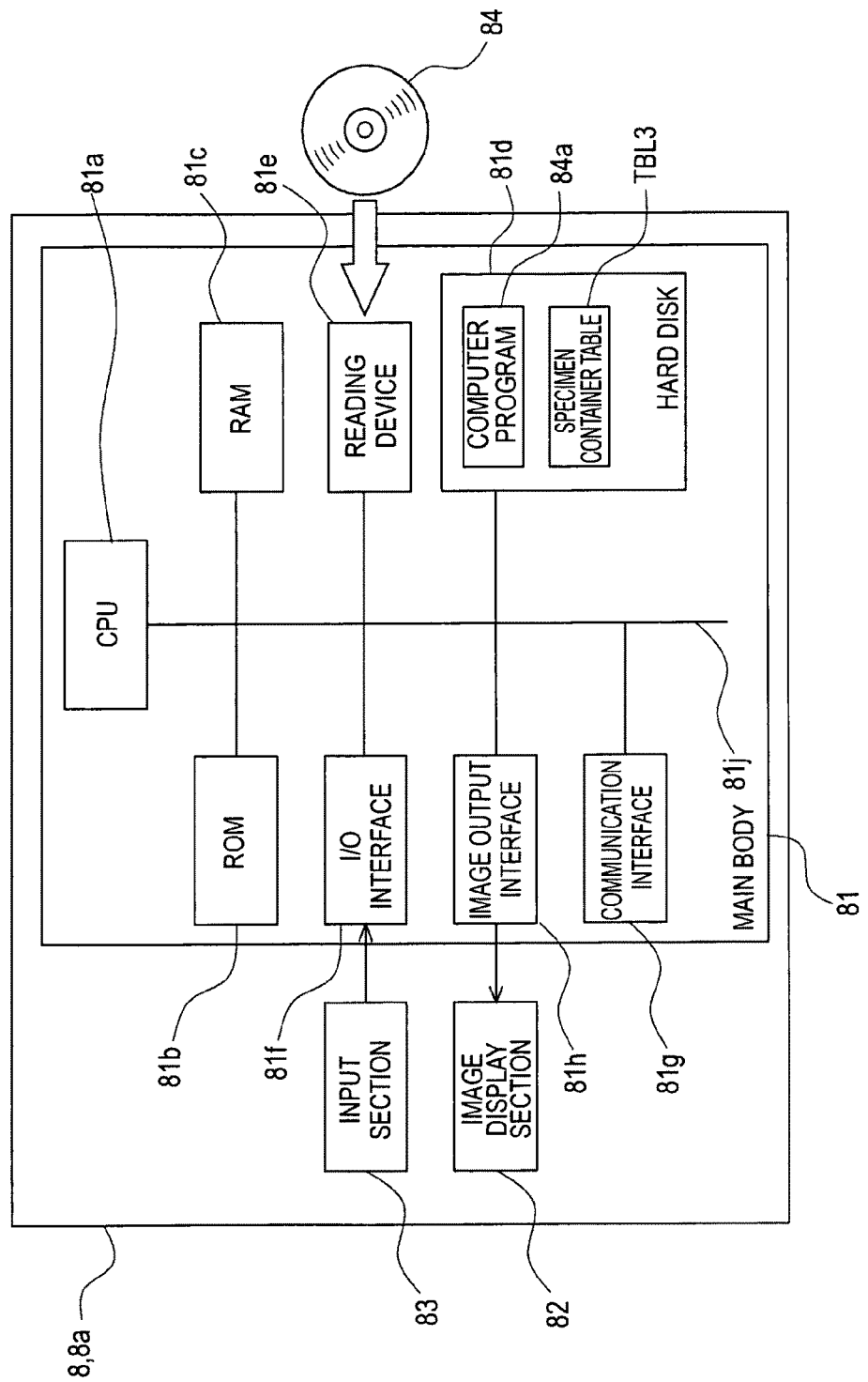
FIG. 14 is a block diagram showing the configuration of a system control apparatus.

FIG. 14 is a block diagram showing the configuration of the system control apparatus 8 according to this embodiment. The system control apparatus 8 is composed of a computer and controls the entire specimen processing system 1. The system control apparatus 8 receives the number of the sample rack L from the specimen putting apparatus 2 and determines the transport destination of the sample rack L.

The system control apparatus 8 is realized by a computer 8a. As shown in FIG. 14, the computer 8a includes a main body 81, an image display section 82 and an input section 83. The main body 81 includes a CPU 81a, a ROM 81b, a RAM 81c, a hard disk 81d, a reading device 81e, an I/O interface 81f, a communication interface 81g and an image output interface 81h. The CPU 81a, ROM 81b, RAM 81c, hard disk 81d, reading device 81e, I/O interface 81f, communication interface 81g and image output interface 81h are connected to each other by a bus 81j.

In the hard disk 81d, various computer programs for execution by the CPU 81a, such as an operating system and an application program, and data, which are used to execute the computer programs, are installed. A system control program 84a to be described later is also installed in the hard disk 81d.

A specimen container table TBL3 which is used to discriminate the types of the specimen containers is provided in the hard disk 81d. FIG. 15 is a schematic diagram showing the structure of the specimen container table TBL3. As shown in the drawing, the specimen container table TBL3 is data having a two-dimensional table form and each row corresponds to the type of a specimen container. Each row stores reference values (hereinafter, referred to as "reference characteristic information") of characteristic information indicating characteristics of a specimen container. Specifically, this reference characteristic information includes a container type ID for specifying the type of specimen container, a length (height) of the specimen container, a length of a cap section, a diameter of the cap section, a length of a small diameter section of a two-stage cap (cap section having two cap diameters of the small diameter section and a large diameter section), a diameter of the small diameter section and color information of the cap section (R value (luminance of red color components), G value (luminance of green color components) and B value (luminance of blue color components)).

The reading device 81e is composed of a flexible disk drive, a CD-ROM drive, a DVD-ROM drive or the like and can read the computer program or data recorded in a portable recording medium 84. In the portable recording medium 84, the system control program 84a for prompting the computer to function as the system control apparatus 8 is stored. The computer 8a can read the system control program 84a from the portable recording medium 84 so as to install the system control program 84a in the hard disk 81d.

The I/O interface 81f is composed of, for example, a serial interface such as USB, IEEE1394 or RS-232C, a parallel interface such as SCSI, IDE or IEEE1284, and an analog interface including a D/A converter and an A/D converter. The input section 83 composed of a keyboard and a mouse is connected to the I/O interface 81f and the user uses the input section 83 so as to input data to the computer 8a.

The communication interface 81g is an Ethernet (registered trade name) interface. The communication interface 81g is connected to the specimen putting apparatus 2, the specimen transport apparatus 3, the processed specimen accommodating apparatus 4, the information processing unit 52 and the host computer 9 via a LAN. Via the communication interface 81g, the computer 8a can send and receive data to and from the above respective apparatuses connected to the LAN by using a predetermined communication protocol.

Since the other configurations of the system control apparatus 8 are the same as the configurations of the above-described information processing unit 52, a description thereof will be omitted.

<Configuration of Host Computer 9>

The host computer 9 is composed of a computer and includes a CPU, a ROM, a RAM, a hard disk, a communication interface and the like. The communication interface is connected to the above-described LAN so as to communicate with the system control apparatus 8, the information processing unit 52 of the blood cell analyzing apparatus 5, an image processing unit 73 of the blood cell image display apparatus 7, the specimen putting apparatus 2, the specimen transport apparatus 3 and the processed specimen accommodating apparatus 4. In the hard disk, measuring orders are stored. The measuring orders include specimen IDs and information on measuring items of objects. When having received request data for a measuring order including a specimen ID from another apparatus, the host computer 9 reads measuring data corresponding to the specimen ID from the hard disk and transmits the measuring data to the apparatus which was the request source. Since the other configurations of the host computer 9 are the same as the configurations of the above-described other computers, a description thereof will be omitted.

Hereinafter, an operation of the specimen processing system 1 according to this embodiment will be described.

<Operation of Specimen Putting Apparatus 2>

Specimen Sorting Operation

Figure 16A:
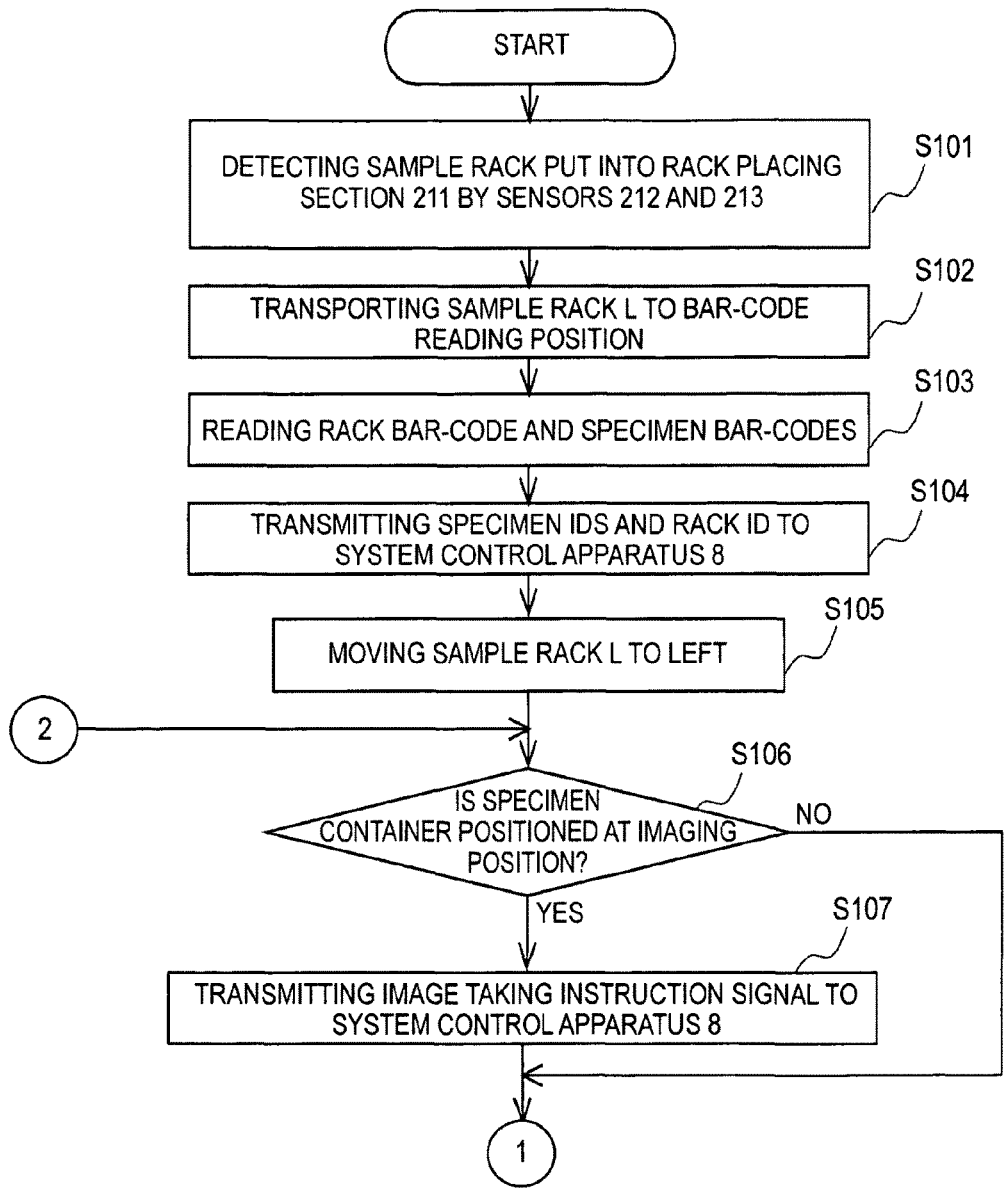
FIG. 16A is a flowchart (first half) showing the flow of a specimen sorting operation of the specimen putting apparatus.

When a specimen is put into the specimen processing system 1, the specimen putting apparatus 2 sorts the sample rack L as to whether it is a rack to be transported to the measuring unit 51 or not. FIGS. 16A and 16B are flowcharts showing the flow of the specimen sorting operation of the specimen putting apparatus 2. The user places the sample rack L accommodating the specimen containers T on the rack placing section 211 of the specimen putting unit 21 and operates the operating panel 214 of the specimen putting unit 21 so as to issue an analysis start instruction to the specimen processing system 1. The control section 2a of the specimen putting apparatus 2 detects the sample rack L put into the rack placing section 211 by the sensors 212 and 213 when the analysis start instruction has been received (Step S101). When an event occurs in which the sensors 212 and 213 detect the sample rack L, the control section 2a starts the movement of the sample rack L. The sample rack L placed on the rack placing section 211 of the specimen putting unit 21 is moved backward on the rack placing section 211 and reaches the bar-code reading position (Step S102).

Next, the control section 2a reads the specimen IDs of the specimens accommodated in the sample rack L and the rack ID of the sample rack L by the bar-code readers 21b and 21c (Step S103). At this time, each of the specimen containers T is horizontally rotated by the horizontal rotation mechanism 21d while being held in the sample rack L, and the specimen bar-code is read when the bar-code label BL1 faces the bar-code reader 21b. In addition, the control section 2a transmits the read specimen IDs and rack ID to the system control apparatus 8 (Step S104). In the data transmitted in Step S104, holding positions (1 to 10) of the specimen containers T in the sample rack L correspond to the specimen IDs of the held specimen containers. Then, the control section 2a moves the sample rack L to the left to deliver the sample rack to the specimen container accommodating unit 22. When the specimen ID cannot be obtained due to a failure to read the specimen bar-code, data indicating the reading failure of the specimen bar-code associated with the holding position is transmitted.

The control section 2a moves the sample rack L, which is fed to the specimen container accommodating unit 22, to the left one pitch at a time by using the transport belt 228 of the rack accommodating section 221 (Step S105). The control section 2a determines whether the specimen container T is positioned at the imaging position 224 (Step S106). This process is performed by referring to a light-receiving level of the light-receiving element 223c of the optical sensor 223a. When the specimen container T is not positioned at the imaging position 224 (No in Step S106), the control section 2a performs a process of Step S108. On the other hand, when the specimen container T is positioned at the imaging position 224 (Yes in Step S106), the control section 2a transmits an image taking instruction signal to the system control apparatus 8 (Step S107). The image taking instruction signal includes the rack ID of the rack, the specimen ID of the specimen and information on the holding position of the specimen container in the sample rack L. As described later, the system control apparatus 8 takes an image captured by the camera 225a when the image taking instruction signal has been received, and then performs image processing on the image so as to determine the type of the specimen container T.

The control section 2a determines whether all the specimen containers T accommodated in the sample rack L have been subjected to the above process, or more precisely, whether a specimen container holding position at the right end of the sample rack L is positioned at the imaging position 224 (Step S108). When the right end of the sample rack L has not yet reached the imaging position 224 (No in Step S108), the control section moves the sample rack L to the left by one pitch (Step S109) and returns the process to Step S106.

When the right end of the sample rack L has reached the imaging position 224 (Yes in Step S108), the control section 2a transmits sorting preparation completion data to the system control apparatus 8 (Step S110) and then stands by to receive transport instruction data or storage instruction data (No in Step S111). The transport instruction data is transmitted from the system control apparatus 8 when the sample rack L accommodates only the specimens to be provided for the blood cell analysis of the blood cell analyzing apparatus 5, and the storage instruction data is transmitted from the system control apparatus 8 when the sample rack L accommodates a specimen which is not to be provided for the blood cell analysis of the blood cell analyzing apparatus 5.

Figure 17:
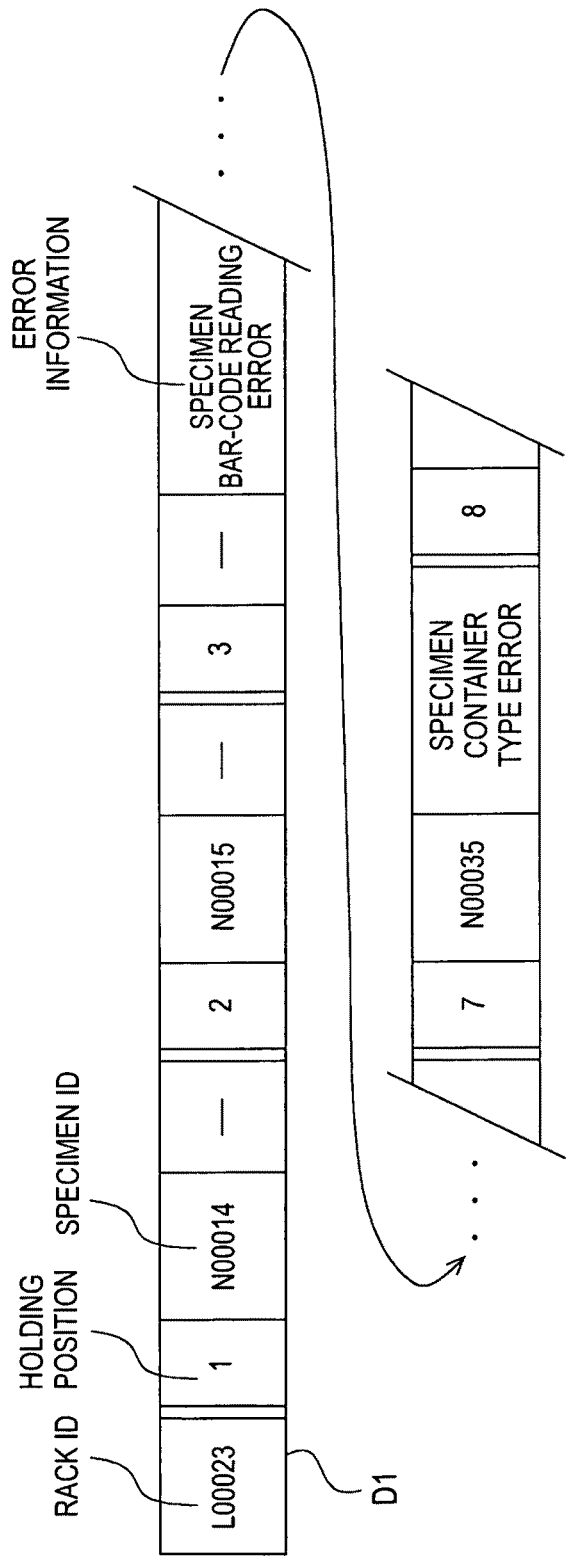
FIG. 17 is a schematic diagram showing the structure of storage instruction data.

When having received the transport instruction data or the storage instruction data (Yes in Step S111), the control section 2a determines whether the received data is the storage instruction data (Step S112). FIG. 17 is a schematic diagram showing the structure of the storage instruction data. Storage instruction data D1 includes the rack ID of the sample rack L, the holding positions (1 to 10) of the specimen containers T in the sample rack L, the specimen IDs of the specimen containers T and error information (abnormal code) indicating the details of the abnormality. The holding position, the specimen ID and the error information of the specimen container T correspond to each other, and the holding position, the specimen ID and the error information of the specimen container T in which an error has occurred can be specified.

Figure 18:
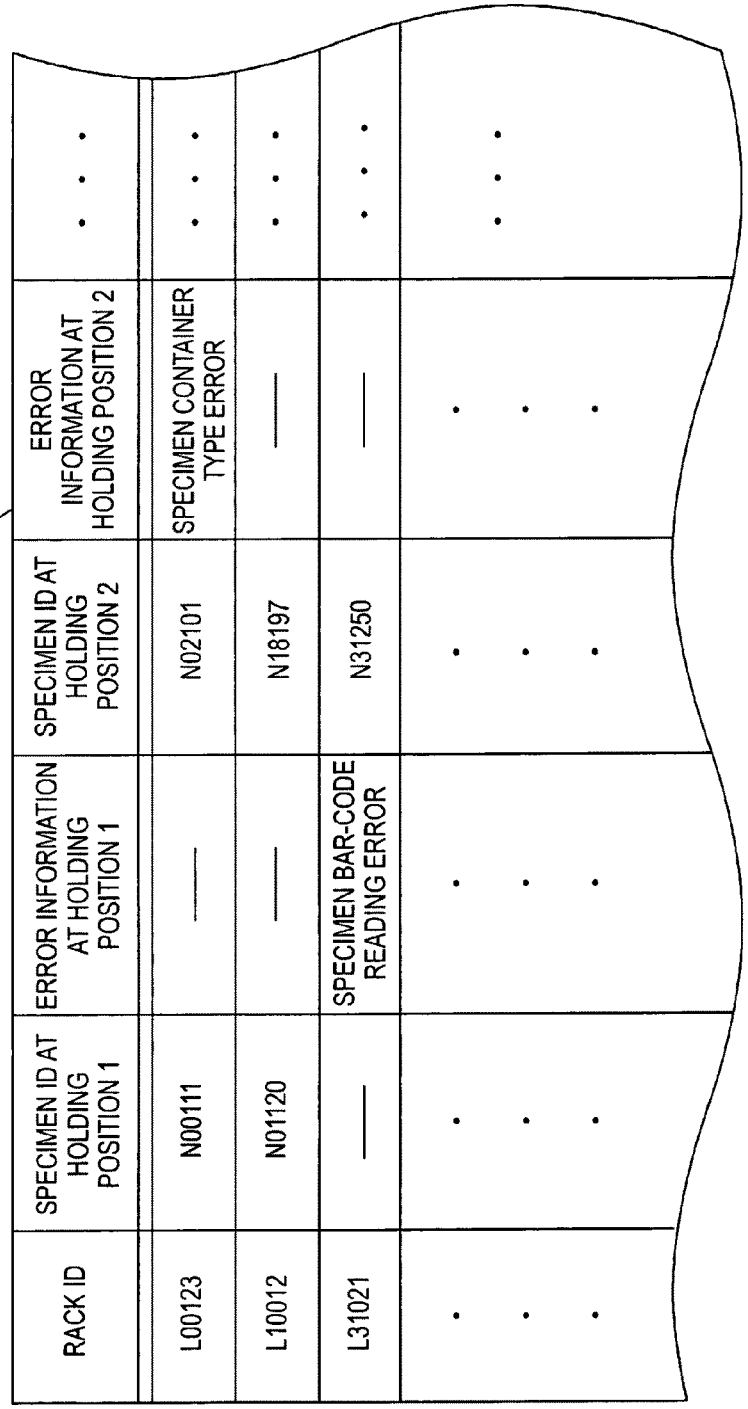
FIG. 18 is a schematic diagram showing the structure of stored rack information.

In Step S112, when the received data is the storage instruction data (No in Step S112), the control section 2a adds the information on the sample rack L to the stored rack information in the memory of the control section 2a on the basis of the storage instruction data (Step S113). FIG. 18 is a schematic diagram showing the structure of the stored rack information. As shown in the drawing, stored rack information D2 includes the rack IDs, the specimen IDs of the holding positions and the error information of the holding positions. The specimen ID and the error information correspond to each other, and it is possible to specify which specimen has which kind of error. In such stored rack information D2, the information relating to all the sample racks L accommodated in the rack accommodating section 221 is included. After that, the control section 2a moves the sample rack L to the rack accommodating section 221 by using the rack delivery section 229 (Step S114) and completes the process.

In Step S112, when the received data is the transport instruction data (Yes in Step S112), the control section 2a further moves the sample rack L to the left so as to deliver the sample rack L to the specimen delivery unit 23 (Step S115). The control section 2a reads the rack bar-code of the sample rack L by using the bar-code reader 23a (Step S116) and moves the sample rack L to the rack conveying position for conveying the sample rack L to the following specimen transport apparatus 3 (Step S117). Then, the control section 2a transmits conveyance request data including the rack ID of the sample rack L to the system control apparatus 8 (Step S118) and stands by to receive conveyance instruction data to be transmitted from the system control apparatus 8 (No in Step S119). When having received the conveyance instruction data from the system control apparatus 8 (Yes in Step S119), the specimen putting apparatus 2 conveys the sample rack L to the adjacent specimen transport apparatus 3 (Step S120) and transmits conveyance completion data to the system control apparatus 8 (Step S121). After that, the control section 2a completes the process.

Retreated Rack Information Display Operation

Figure 19:
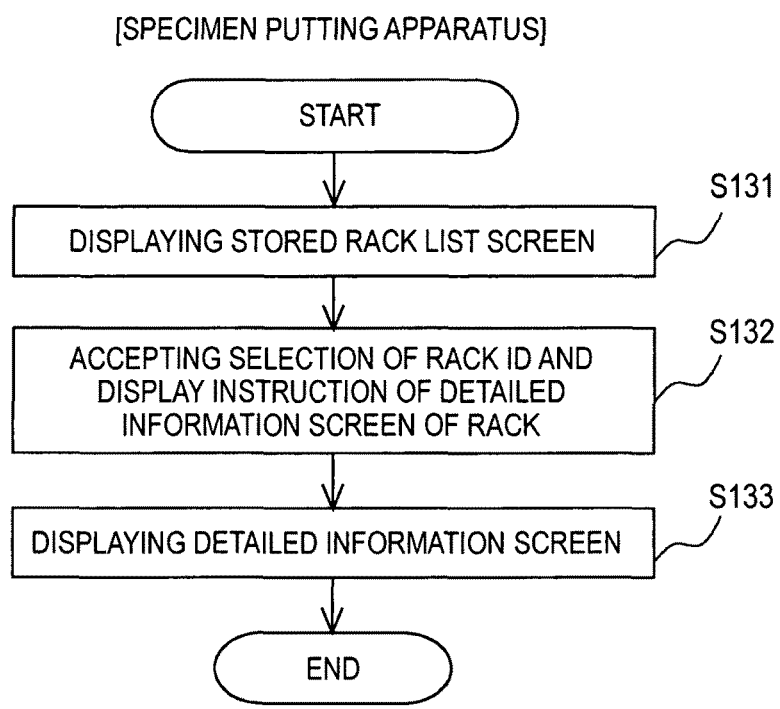
FIG. 19 is a flowchart showing the flow of a retreated rack information display operation of the specimen putting apparatus.

The information relating to the sample rack L, which has been retreated to the rack accommodating section 221 of the specimen container accommodating unit 22 as described above, is displayed on the liquid crystal display section 227 of the specimen container accommodating unit 22. FIG. 19 is a flowchart showing the flow of the retreated rack information display operation. When the storage instruction data D1 is transmitted from the system control apparatus 8, the stored rack information D2 of the control section 2a is updated and the sample rack L is moved to the rack accommodating section 221, the control section 2a displays a stored rack list screen on the liquid crystal display section 227 on the basis of the stored rack information D2 (Step S131).

Figure 20:
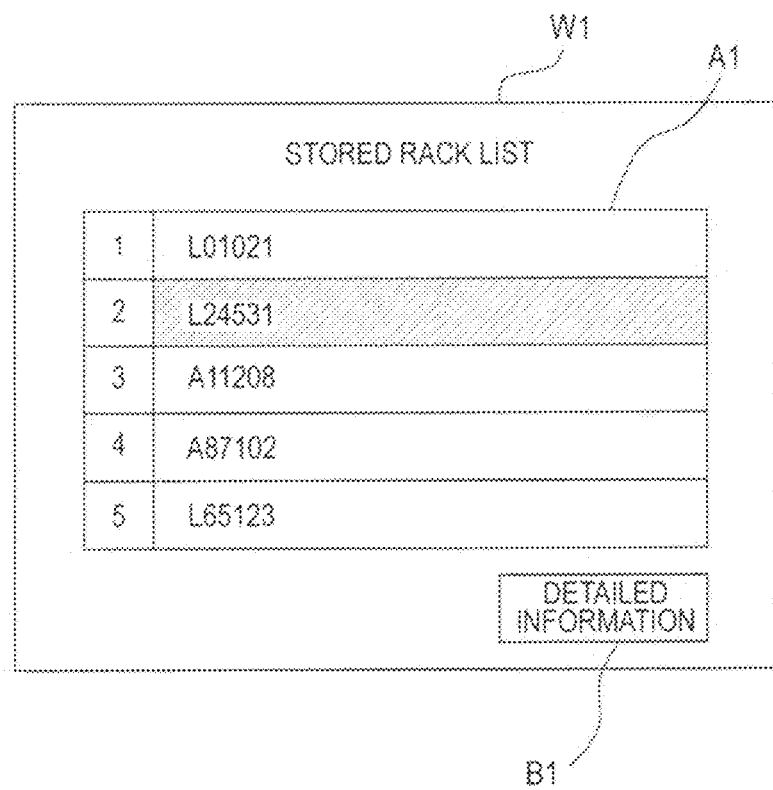
FIG. 20 is a diagram showing an example of a stored rack list screen.

FIG. 20 is a diagram showing an example of the stored rack list screen. As shown in the drawing, in a stored rack list screen W1, a list display area A1 in which the rack IDs of the sample racks L in which an abnormality has been detected are displayed as a list is provided. In the list display area A1, an operator touches each rack ID with a finger so as to select the rack ID. The selected rack ID is displayed with a color different from that of the rack IDs which are not selected. In addition, in the stored rack list screen W1, a display switching button B1 is provided for switching the screen display into a detailed information screen of the rack ID selected in the list display area A1. When accepting the selection of the rack ID from the operator and a display instruction of the detailed information screen of the sample rack L (Step S132), the control section 2a displays the detailed information screen on the liquid crystal display section 227 (Step S133). The operator may not operate the touch panel so as to select the rack ID and input the display instruction of the detailed information screen, but may read the rack bar-code of the sample rack L by the handy bar-code reader 222c so as to input the read rack ID to the control section 2a to thereby display the detailed information screen of the sample rack L. After displaying the detailed information screen, the control section 2a completes the process.

Figure 21:
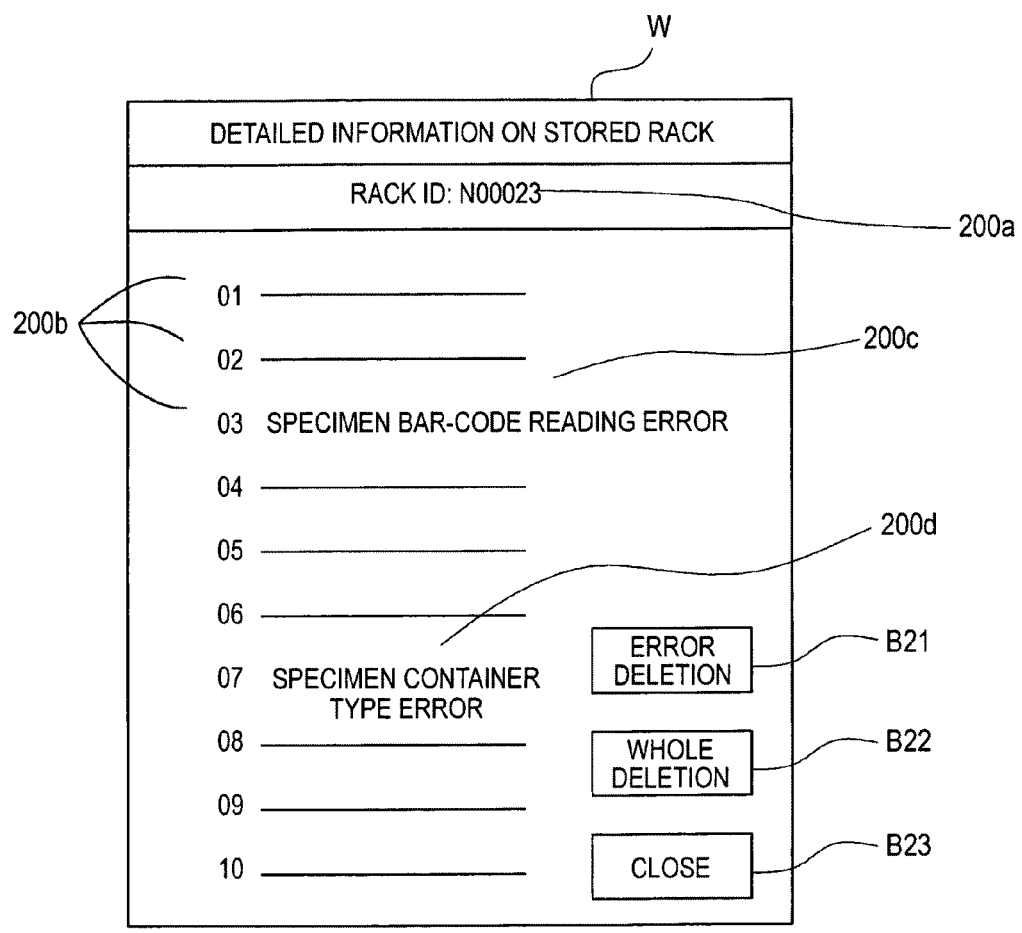
FIG. 21 is a diagram showing an example of a detailed information screen of a sample rack.

FIG. 21 is a diagram showing an example of the detailed information screen of the sample rack L. As shown in the drawing, a detailed information screen W2 includes a rack ID 200a, holding position numbers 200b in the sample rack and error information 200c and 200d corresponding to the holding positions. The error information 200c is information indicating the failure in specimen bar-code reading and the error information 200d is information indicating the specimen container type error. Furthermore, the detailed information screen W2 is provided with a first delete button B21 for deleting the information on the sample rack L, a second delete button B22 for deleting the selected error information and a close button B23 for instructing the completion of the display of this screen. In the detailed information screen W2, desired error information can be selected through the touch panel operation by the operator. In a state in which the error information is selected in this manner, the operator selects the second delete button B22 and thus can input an instruction to delete the error information. Moreover, by selecting the specimen bar-code reading error, taking out the specimen container T in which the specimen bar-code reading has failed from the sample rack L, and re-reading the specimen bar-code with the handy bar-code reader 222c, the operator can solve the specimen bar-code reading error.

By confirming with the detailed information screen, the operator can take appropriate action, such as taking out the specimen container T having a specimen container shape error from the sample rack L and replacing the specimen container with another specimen container, or taking out the specimen container T in which the bar-code reading has failed, re-reading the specimen bar-code by using the handy bar-code reader 222c, returning the specimen container to its original holding position in the sample rack L and placing the sample rack L in the rack re-putting section 231 of the specimen delivery unit 23. The sample rack L re-put into the rack re-putting section 231 is automatically conveyed to the specimen transport apparatus 3.

<Operation of System Control Apparatus 8>

Next, an operation of the system control apparatus 8 will be described.

Measuring Order Obtaining Operation

The system control apparatus 8 receives a specimen ID from the specimen putting apparatus 2 and makes an inquiry to the host computer 9 for a measuring order by using the specimen ID as a key. Herein, the measuring order is data indicating an instruction of analysis items to be analyzed for the specimen, and includes attribute information on the specimen, such as the specimen ID, patient ID and the name of the patient, and information on the analysis item. Hereinafter, this operation will be described in detail.

FIG. 22 is a flowchart showing the flow of the measuring order obtaining operation of the system control apparatus 8. As described above, the specimen putting apparatus 2 transmits the specimen IDs and rack ID read by the bar-code readers 21b and 21c to the system control apparatus 8. The rack ID and the specimen IDs are received by the communication interface 81g of the system control apparatus 8 (Step S201). In the CPU 81a, a process of Step S202 is invoked when an event occurs in which the rack ID and the specimen IDs are received.

In Step S202, the CPU 81a determines whether specimen ID reading failure data is included in the received data (Step S202). When the specimen ID reading failure data is included in the received data (Yes in Step S202), the CPU 81a stores in a hard disk 51d specimen bar-code reading error information, indicating that a specimen bar-code reading failure has occurred, which corresponds to the rack ID of the sample rack L (in the case of a rack ID reading failure, a rack sequential number sequentially assigned to the put sample rack L) and the holding position of the specimen container (Step S203), and performs a process of Step S204. On the other hand, when the specimen ID reading failure data is not included (No in Step S202), the CPU 81a performs the process of Step S204.

In Step S204, the CPU 81a transmits one of the received specimen IDs to the host computer 9 and requests a measuring order corresponding to the specimen ID from the host computer 9 (Step S204). The CPU 81a stands by to receive the measuring order (Step S205). When the system control apparatus 8 receives the measuring order transmitted from the host computer 9 ("successful reception" in Step S205), the CPU associates the received measuring order with the rack ID and stores the measuring order in the hard disk 81d (Step S206). On the other hand, when the measuring order corresponding to the specimen ID cannot be received (when the measuring order is not received within a predetermined reception period, or when information indicating that the corresponding measuring order does not exist is received from the host computer 9) ("reception failure" in Step S205), the information indicating that the measuring order does not exist (measuring order obtaining error information) is associated with the rack ID and the holding position of the specimen container T and this information is stored (Step S207).

Next, the CPU 81a determines whether the specimen IDs corresponding to the rack ID, that is, the specimen IDs of all the specimens accommodated in the sample rack L with the rack ID have been subjected to an inquiry of measuring order (Step S208). When there is a specimen ID not subjected to the inquiry of measuring order (No in Step S208), the CPU returns the process to Step S204 and requests a measuring order corresponding to the specimen ID not yet subjected to the inquiry of measuring order from the host computer 9.

On the other hand, when all of the specimen IDs have been subjected to the inquiry of measuring order (Yes in Step S208), the CPU 81a completes the process.

Specimen Container Type Discriminating Process

Figure 23:
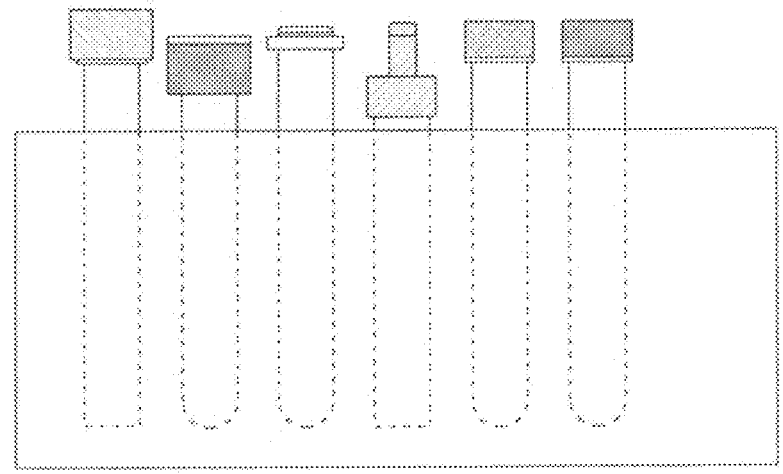
FIG. 23 is a diagram showing examples of specimen container shapes.

FIG. 23 is a diagram showing examples of a specimen container shape. Currently, various types of specimen containers are commercially available. Depending on the type, these specimen containers have different heights, widths (sizes), heights of inner bottom surfaces and the like, so their shapes are different from each other. The thickness and width of the cap section CP also vary in accordance with the specimen container type. When plural types of specimen containers are intermingled with each other, the biggest problem is that the heights of inner bottom surfaces of specimen containers are different. In specimen containers having different inner bottom surface heights, if a movement distance of the aspiration tube of the specimen aspirating section 511 of the measuring unit 51 is not changed for each container, the aspiration tube is brought into contact with and jabbed into the inner bottom surface of the specimen container, or the movement distance is insufficient and the specimen cannot be aspirated in an amount necessary for the measurement. In this manner, a failure is caused in aspiration.

In specimen processing systems having a transport apparatus for automatically transporting specimens, specimen containers sealed by cap sections are used. In many cases, cap sections of these specimen containers have different shapes and colors in accordance with the type. Accordingly, the system control apparatus 8 according to this embodiment obtains an image of the specimen container T put into the specimen putting apparatus 2 so as to discriminate the type of the specimen container on the basis of the cap section in the image. Hereinafter, this operation will be described in detail.

FIG. 24 is a flowchart showing the flow of the specimen container type discriminating process of the system control apparatus 8 according to this embodiment. As shown in FIG. 24, in the CPU 81a of the system control apparatus 8, a process of Step S212 is invoked when an event occurs in which an image taking instruction signal transmitted from the specimen putting apparatus 2 is received by the system control apparatus 8 (Step S211).

In Step S212, the CPU 81a takes an image captured by the camera 225a at that time point (Step S212). The entire cap section CP of the specimen container T is included in the image. Next, the CPU 81a detects a shape and a position of the cap section CP of the specimen container T in the taken image (Step S213). Hereinafter, this operation will be described in detail.

FIG. 25 is a schematic diagram for illustrating the process of detecting the shape and the position of the cap section CP of the specimen container T in the image. First, the CPU 81a performs the following process on a processing area 101 for detecting the shape and the position of the cap section of the specimen container T in an image 100. In this embodiment, imaging is performed while a white wall or the like is disposed behind the specimen container T, so that a background in the image captured by the camera 225a is brighter than the cap section. The processing area 101 is a predetermined area, which includes the cap section of the specimen container T. For each Y coordinate in the processing area 101, the CPU 81a accumulates luminance values of pixels in an X direction in the processing area 101. That is, an accumulation value (hereinafter, referred to as "horizontal luminance accumulation value") of the luminance values of the pixels in a transverse row of pixel groups at the upper end included in the processing area 101 is calculated, and a horizontal luminance accumulation value of a transverse row of pixel groups on the lower side thereof is calculated. This operation is repeated until reaching the lower end of the processing area 101 while incrementing a Y coordinate value. A horizontal luminance accumulation value HD is expressed by the following formula (1).

$$HD(y) = \sum_{x=XL}^{x=XR} Y(x, y) \quad (1)$$

Herein, XL is an X coordinate value at the left end of the processing area 101, and XR is an X coordinate value at the right end of the processing area 101. A luminance value Y of a pixel (coordinate=x, y) is obtained by the following formula (2).

$$Y(x,y)=R(x,y)\times 0.30+G(x,y)\times 0.59+B(x,y)\times 0.11 \quad (2)$$

Herein, R is a luminance of red color components, G is a luminance of green color components and B is a luminance of blue color components.

In FIG. 25, a graph of the horizontal luminance accumulation value obtained as described above in the processing area 101 is denoted by reference numeral 101a. The horizontal luminance accumulation value related to the processing area 101 is high in the background and is low in the image of the cap section CP of the specimen container T. Accordingly, the CPU 81a differentiates the horizontal luminance accumulation value in a Y direction and detects a portion in which the horizontal luminance accumulation value is sharply lowered in a direction toward the lower side from the upper end of the processing area 101. In this manner, a position of the upper end of the cap section CP is detected.

The CPU 81a further checks the horizontal luminance accumulation value in the direction toward the lower side of the processing area 101. Herein, when a portion in which the horizontal luminance accumulation value is sharply lowered is detected, the position of this portion is determined as a stage section (boundary position between a small diameter section and a large diameter section) of a two-stage cap (cap section having two cap diameters of the small diameter section and the large diameter section).

The CPU 81a further checks the horizontal luminance accumulation value in the direction toward the lower side of the processing area 101 and detects a portion in which the horizontal luminance accumulation value sharply increases. In this manner, a position of the lower end of the cap section CP is detected. When the stage section of the two-stage cap is not detected and the position of the lower end of the cap section CP is detected, this cap section is a one-stage cap (cap section having no stage section and having the same diameter as a whole).

A portion in which the horizontal luminance accumulation value is sharply lowered is also detected in the direction toward the lower side of the processing area 101. When the position of this portion is in a prescribed range, the position is recognized as the upper end of the sample rack L.

By the information obtained as described above, the CPU 81a obtains a length (hereinafter, referred to as "cap length") from the upper end to the lower end of the cap section, a length (hereinafter, referred to as "cap small diameter section length") from the upper end to the stage section of the two-stage cap, and a length (height) of the specimen container. The length of the specimen container is obtained by adding the length from the upper end position of the cap section to the upper end position of the rack to an insertion depth (predetermined value) of the specimen container in the sample rack L.

Moreover, the CPU 81a determines a square processing area 102, of which the upper and lower ends are equal to the upper end position and the lower end position of the cap section obtained as described above, and the left and right ends are equal to the left and right ends of the processing area 101. For each X coordinate value in the processing area 102, the CPU 81a calculates a luminance accumulation value (hereinafter, referred to as "vertical luminance accumulation value"). That is, an accumulation value (vertical luminance accumulation value) of luminance values of pixels in a vertical column of pixel groups at the left end included in the processing area 102 is calculated, and a vertical luminance accumulation value of a vertical column of pixel groups on the right side thereof is calculated. This operation is repeated until reaching the right end of the processing area 102 while incrementing an X coordinate value. A vertical luminance accumulation value VD is expressed by the following formula (3).

$$VD(x) = \sum_{y=YT}^{y=YB} Y(x, y) \quad (3)$$

Herein, YT is a Y coordinate value at the upper end of the processing area 102 and YB is a Y coordinate value at the lower end of the processing area 102.

In the drawing, a graph of the vertical luminance accumulation value in the processing area 102 is denoted by reference numeral 102a. As shown by the graph 102a, the vertical luminance accumulation value is high in a background and is low in the image of the cap section CP of the specimen container T. In the case of the two-stage cap, the vertical luminance accumulation value of the large diameter section is lower than that of the small diameter section. Accordingly, the CPU 81*a* differentiates the vertical luminance accumulation value in the X direction and detects a portion in which the vertical luminance accumulation value is sharply lowered in a direction toward the right side from the left end of the processing area 102. In this manner, a position of the left end of the cap section CP is detected.

The CPU 81*a* checks the vertical luminance accumulation value in the direction toward the right side of the processing area 102. Herein, when a portion in which the vertical luminance accumulation value is sharply lowered is detected, the position of this portion is determined as the left end of the small diameter section of the two-stage cap. When the left end position of the two-stage cap is detected, the CPU 81*a* checks the vertical luminance accumulation value in the direction toward the right side of the processing area 102 and determines a portion in which the vertical luminance accumulation value sharply increases as the right end of the small diameter section.

The CPU 81*a* further checks the vertical luminance accumulation value in the direction toward the right side of the processing area 102 and detects a portion in which the vertical luminance accumulation value sharply increases. In this manner, a position of the right end of the cap section CP is detected. When the left and right ends of the two-stage cap are not detected and the position of the right end of the cap section is detected, this cap section is a one-stage cap.

By the information obtained as described above, the CPU 81*a* obtains a diameter (the length from the left end to the right end of the cap section. Hereinafter, referred to as "cap diameter") of the cap section and a diameter (the length from the left end to the right end of the small diameter section. Hereinafter, referred to as "small cap diameter") of the small diameter section of the two-stage cap.

The CPU 81*a* determines whether the detection of the shape and the position of the cap section of the specimen container, which is performed by the above-described process, has succeeded (Step S214). When the detection of the shape and the position of the cap section has failed (No in Step S214), the CPU associates specimen container cap error information indicating that the specimen container does not have a cap section with the rack ID of the sample rack L, the specimen ID of the specimen and the holding position of the specimen container T in the sample rack L, stores the information in the hard disk 81*d* (Step S215), and completes the process.

On the other hand, when the detection of the shape and the position of the cap section has succeeded (Yes in Step S214), the CPU 81*a* uses the positions of the upper, lower, left and right ends of the cap section obtained as described above, and as well as the above positions, the position of the stage section and the positions of the left and right ends of the small diameter section in the case of the two-stage cap, to specify an area of the cap section in the image, and then obtains R, G and B values of pixels in this area. The CPU calculates an average value of each of the R, G and B values (Step S216).

Next, the CPU 81*a* compares the characteristic information on the specimen container obtained by the above-described process, that is, the length of the specimen container, the shape information (cap length, cap diameter, cap small diameter section length and small cap diameter) of the cap section and the color information (average value of each of the R, G and B values) of the cap section with the reference characteristic information on the various specimen containers registered in the specimen container table TBL3 so as to determine whether there is a specimen container type corresponding to the specimen container T in a predetermined error range (Step S217). When there is a specimen container type corresponding to the specimen container T in the predetermined error range (Yes in Step S217), the CPU 81*a* associates the container type ID for specifying the type of the specimen container with the rack ID of the sample rack L, the specimen ID of the specimen and the holding position of the specimen container T in the sample rack L, stores the container type ID in the hard disk 81*d* (Step S218) and completes the process. On the other hand, when there is no specimen container type corresponding to the specimen container T in the predetermined error range (No in Step S217), the CPU 81*a* associates specimen container type error information indicating a specimen container type abnormality with the rack ID of the sample rack L, the specimen ID of the specimen and the holding position of the specimen container T in the sample rack L, stores the information in the hard disk 81*d* (Step S219) and completes the process.

Sorting Instruction Process

The system control apparatus 8 instructs the specimen putting apparatus 2 to sort specimens into the specimens (sample rack L) to be transported to the following measuring unit 51 and the specimens (sample rack L) which are not to be transported to the measuring unit 51. Hereinafter, this process will be described in detail.

FIG. 26 is a flowchart showing the procedure of the sorting instruction process of the system control apparatus 8. As shown in FIG. 26, in the CPU 81*a*, a process of Step S242 is invoked when an event occurs in which the system control apparatus 8 receives sorting preparation completion data transmitted from the specimen putting apparatus 2 (Step S241).

The sorting preparation completion data includes the rack ID. When having received the sorting preparation completion data, the CPU 81*a* reads from the hard disk 51*d* the specimen IDs, the specimen bar-code reading error information (information indicating that the reading of the specimen ID has failed), the specimen container cap error information (information indicating that the specimen container does not have a cap), the measuring order obtaining error information (information indicating that the measuring order corresponding to the specimen ID does not exist), and the specimen container type error information (information indicating that the type of the specimen container is unknown), which correspond to the rack IDs included in the sorting preparation completion data (Step S242). Then, the CPU 81*a* performs a determining operation on all the specimen containers corresponding to the rack ID for determining whether the error information exists (Step S243). When there is no error information on any of the specimen containers (Yes in Step S243), the CPU transmits transport instruction data to the specimen putting apparatus 2 (Step S244) and completes the process. On the other hand, in Step S243, when the error information exists on at least one specimen container (No in Step S243), the CPU 81*a* transmits the storage instruction data D1 (see FIG. 17 for reference) including the above read error information to the specimen putting apparatus 2 (Step S245) and completes the process. In the sorting instruction process, even when the sorting preparation completion data does not include the rack ID (when the reading of the rack bar-code has failed), the storage instruction data including rack ID reading error information is transmitted.

Transport Instruction Process

The system control apparatus 8 receives the conveyance request data from the specimen putting apparatus 2, determines the transport destination of the sample rack L by using the specimen ID included in the conveyance request data and instructs the respective apparatuses to transport the sample rack to the determined transport destination. Hereinafter, this operation will be described in detail.

FIG. 27A is a flowchart showing the procedure of a first transport instruction process of the system control apparatus 8. In the first transport instruction process, the transport destination of the sample rack L is determined and a transport instruction is issued to the specimen transport apparatus 3 disposed in front of the measuring unit 51 on the uppermost-stream side in the transport direction. The conveyance request data transmitted from the specimen putting apparatus 2 is received by the communication interface 81g of the system control apparatus 8 (Step S251). In the CPU 81a, a process of Step S252 is invoked when an event in which the conveyance request data is received occurs.

In Step S252, the CPU 81a searches the measuring order stored in the hard disk 81d by using the rack ID, included in the received conveyance request data, as a key (Step S252). Next, the CPU 81a determines the transport destination of the sample rack L on the basis of the measuring items included in each received measuring order (Step S253). In this process, the measuring unit 51, which is capable of executing all the measuring items included in the measuring order and which is not performing a measurement or has the smallest number of planned measurements at that time point is determined as a measurement destination.

Next, on the basis of the determined transport destination, the CPU 81a transmits conveyance preparation instruction data of the sample rack L to the specimen transport apparatus 3 (that is, the rightmost specimen transport apparatus 3 in FIG. 1) adjacent to the specimen putting apparatus 2 (Step S254). The conveyance preparation instruction data includes data (hereinafter, referred to as "designated transport line instruction data") indicating the transport line (measuring line L1 or skip line L2) for transporting the sample rack L in the specimen transport apparatus 3. In addition, the conveyance preparation instruction data includes the measuring orders of the specimens and the container type IDs of the specimen containers in the sample rack L. That is, when the transport destination of the sample rack L is the measuring unit 51 on the uppermost-stream side in the transport direction of the sample rack L, data indicating the measuring line L1 as the designated transport line instruction data is set in the conveyance preparation instruction data. On the other hand, when another measuring unit 51 is determined as the transport destination, data indicating the skip line L2 as the designated transport line instruction data is set in the conveyance preparation instruction data. The specimen transport apparatus 3 receiving the conveyance preparation instruction data performs an operation of preparing the transport mechanism indicated by the designated transport line instruction data included in the conveyance preparation instruction data (an operation to receive the sample rack L), and then transmits conveyance preparation completion data.

The CPU 81a stands by to receive the conveyance preparation completion data from the specimen transport apparatus 3 (No in Step S255). When the conveyance preparation completion data is transmitted from the specimen transport apparatus 3 and is received by the system control apparatus 8 (Yes in Step S255), the CPU 81a transmits conveyance instruction data of the sample rack L to the specimen putting apparatus 2 (Step S256). As described above, when having received the conveyance instruction data, the specimen putting apparatus 2 conveys the sample rack L to the specimen transport apparatus 3 and transmits conveyance completion data. The CPU 81a stands by to receive the conveyance completion data from the specimen putting apparatus 2 (No in Step S257). When the conveyance completion data is transmitted from the specimen putting apparatus 2 and is received by the system control apparatus 8 (Yes in Step S257), the CPU 81a stands by to receive conveyance completion data from the specimen transport apparatus 3 (No in Step S258). When the conveyance completion data is transmitted from the specimen transport apparatus 3 and is received by the system control apparatus 8 (Yes in Step S258), the CPU 81a completes the process.

Figure 27B:
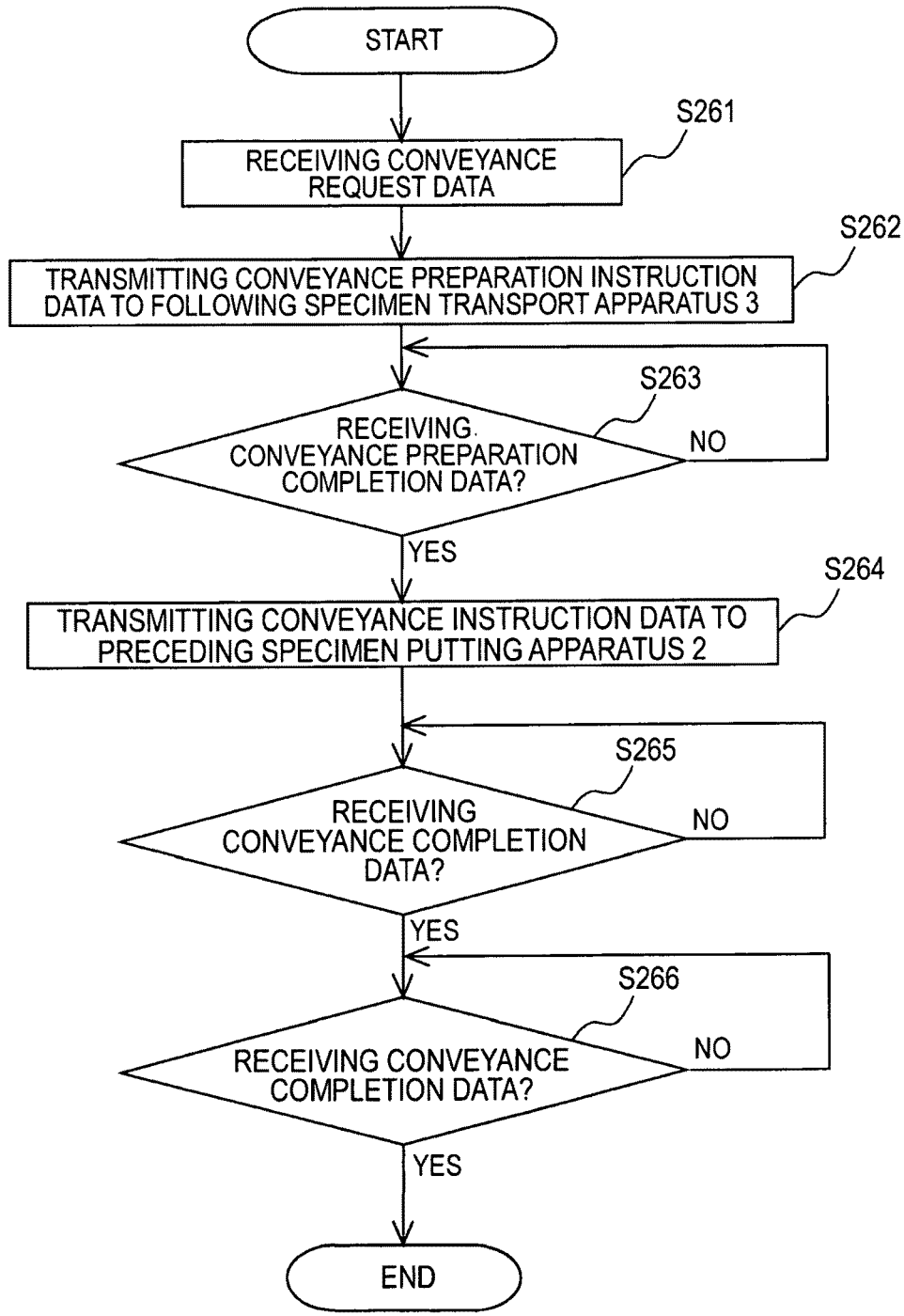
FIG. 27B is a flowchart showing the procedure of a second transport instruction process of the system control apparatus.

Next, a second transport instruction process of the system control apparatus 8 will be described. In the second transport instruction process, a transport instruction is issued to the specimen transport apparatus 3 disposed in front of the second or third measuring unit 51 in the transport direction of the sample rack L. FIG. 27B is a flowchart showing the procedure of the second transport instruction process. When the sample rack L transported by the specimen transport apparatus 3 reaches a conveyance position for conveying the sample rack L to the following specimen transport apparatus 3 (or specimen transport apparatus 301), conveyance request data including the rack ID of the sample rack L is transmitted from the specimen transport apparatus 3. The conveyance request data transmitted from the specimen transport apparatus 3 is received by the communication interface 81g of the system control apparatus 8 (Step S261). In the CPU 81a, a process of Step S262 is invoked when an event in which the conveyance request data is received from the specimen transport apparatus 3 occurs.

In Step S262, the CPU 81a transmits conveyance preparation instruction data of the sample rack L to the specimen transport apparatus 3 following the present specimen transport apparatus 3 on the basis of the transport destination determined by the transport destination determining process (Step S262). Since the conveyance preparation instruction data is the same as the above-described conveyance preparation instruction data, a description thereof will be omitted.

Next, the CPU 81a stands by to receive conveyance preparation completion data from the specimen transport apparatus 3 (No in Step S263). When the conveyance preparation completion data is transmitted from the specimen transport apparatus 3 and is received by the system control apparatus 8 (Yes in Step S263), the CPU 81a transmits conveyance instruction data of the sample rack L to the preceding specimen transport apparatus 3 (conveyance side) (Step S264). When having received the conveyance instruction data, the preceding specimen transport apparatus 3 conveys the sample rack L to the following specimen transport apparatus 3 and transmits conveyance completion data. The CPU 81a stands by to receive the conveyance completion data from the preceding specimen transport apparatus 3 (No in Step S265). When the conveyance completion data is transmitted from the preceding specimen transport apparatus 3 and is received by the system control apparatus 8 (Yes in Step S265), the CPU 81a stands by to receive conveyance completion data from the following specimen transport apparatus 3 (No in Step S266). When the conveyance completion data is transmitted from the following specimen transport apparatus 3 and is received by the system control apparatus 8 (Yes in Step S266), the CPU 81a completes the process.

<Operation of Control Section 32 of Specimen Transport Apparatus 3>

Figure 28A:
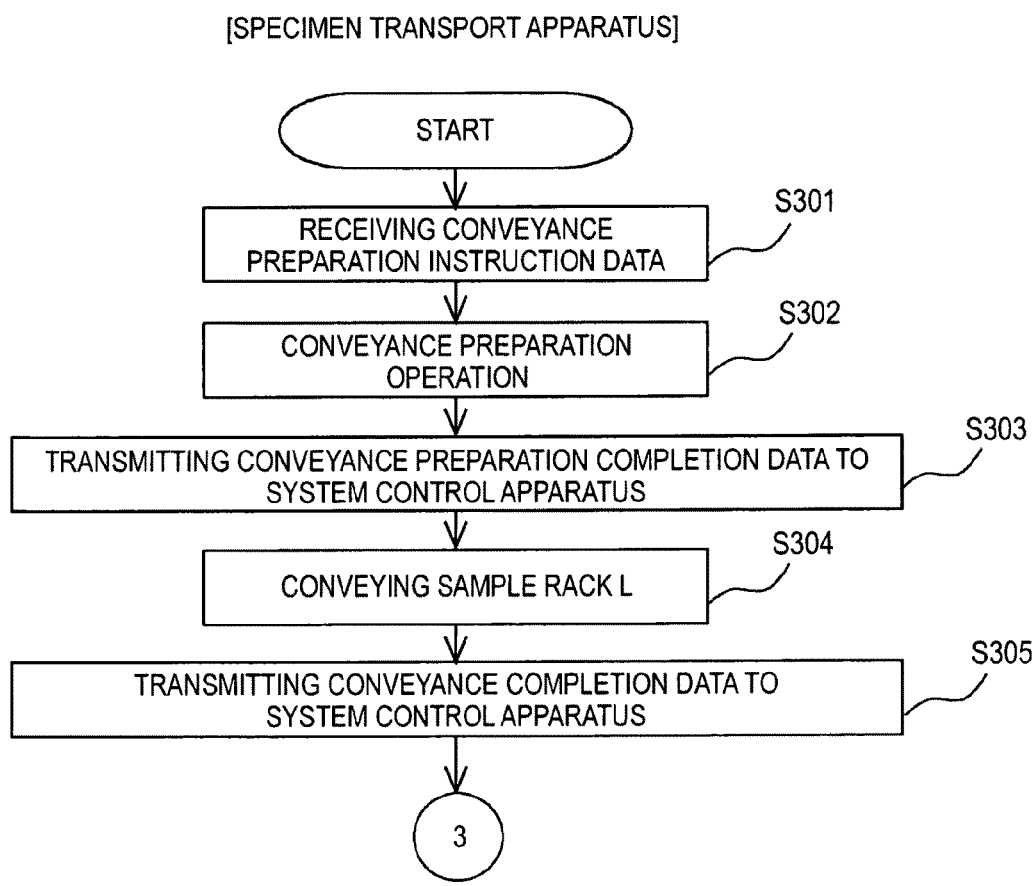
FIG. 28A is a flowchart (first half) showing the flow of a process of controlling a transport mechanism by a control section of the specimen transport apparatus.
Figure 28B:
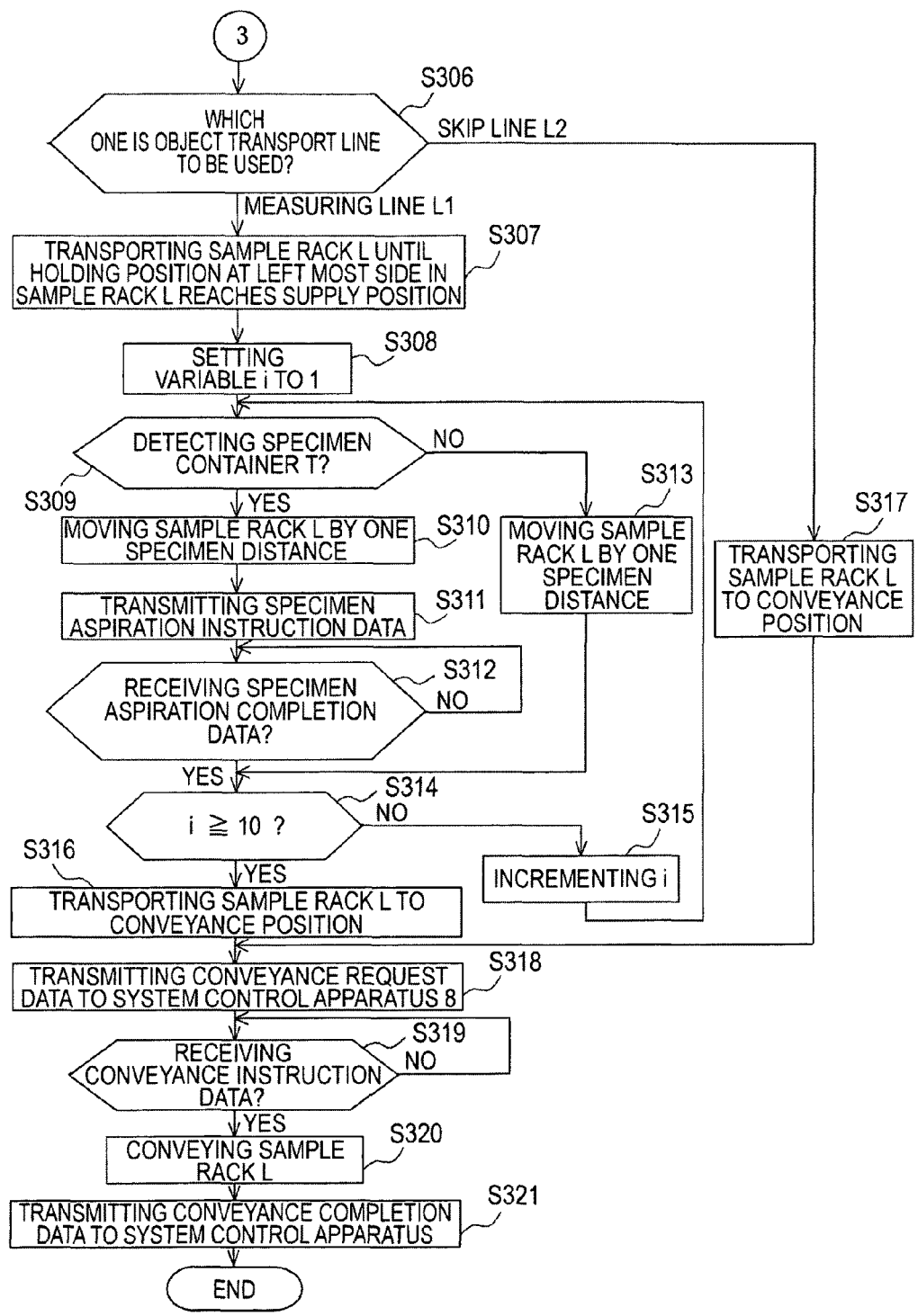
FIG. 28B is a flowchart (second half) showing the flow of the process of controlling the transport mechanism by the control section of the specimen transport apparatus.

Herein, an operation of the control section 32 of the specimen transport apparatus 3 disposed in front of the measuring unit 51 will be described. FIGS. 28A and 28B are flowcharts showing the flow of the process of controlling the transport mechanism 31 by the control section 32. The conveyance preparation instruction data transmitted from the system control apparatus 8 is received by the control section 32 (Step S301). A transport control program which is executed by the CPU of the control section 32 is an event-driven program, and in the control section 32, a process of Step S302 is invoked when an event in which the conveyance preparation instruction data is received occurs.

In Step S302, the control section 32 performs a conveyance preparation operation by driving the belt 321a of the transport mechanism 31 and the like (Step S302). When the conveyance preparation is completed, the control section 32 transmits conveyance preparation completion data for notifying that the conveyance preparation is completed to the system control apparatus 8 (Step S303).

In response to the transmission of the conveyance preparation completion data, the sample rack L is conveyed from the preceding apparatus and is thus conveyed to the transport mechanism 31 (Step S304). When the conveyance of the sample rack L is completed, the control section 32 transmits conveyance completion data for notifying that the conveyance of the sample rack L is completed to the system control apparatus 8 (Step S305).

Next, the control section 32 determines whether designated transport line instruction data included in the conveyance preparation instruction data indicates the measuring line L1 or the skip line L2, that is, whether the object transport line to be used is the measuring line L1 or the skip line L2 (Step S306). In Step S306, when the designated transport line instruction data included in the conveyance preparation instruction data indicates the measuring line L1, that is, when the object transport line to be used is the measuring line L1 ("measuring line L1" in Step S306), the control section 32 controls the transport mechanism 31 so as to move the sample rack L until the holding section positioned at the leftmost side in FIG. 3, out of the holding sections for the specimen containers T in the sample rack L, reaches the specimen container detection position (Step S307). Next, the control section 32 sets a variable i, which indicates the holding position of the specimen container T in the sample rack L, to 1 (Step S308), and determines whether the specimen container sensor 38 detects the specimen container T at the specimen container detection position (Step S309). When the specimen container T is detected (Yes in Step S309), the control section moves the sample rack L to the left by one specimen distance (Step S310) and transmits specimen aspiration instruction data indicating a specimen aspiration instruction to the information processing unit 52 (Step S311). This specimen aspiration instruction data includes the container type ID for specifying the type of the specimen container for the specimen. When the information processing unit 52 receives the specimen aspiration instruction data, as described below, the specimen container T detected by the specimen container sensor 38 is transported to the specimen supply position 35c, the specimen container T is taken into the measuring unit 51, the specimen aspirating section 511 is lowered by a descent amount corresponding to the type of the specimen container T, and the specimen is aspirated. When the aspiration of the specimen is completed, the information processing unit 52 transmits specimen aspiration completion data. The control section 32 stands by to receive the specimen aspiration completion data (No in Step S312). When having received the specimen aspiration completion data (Yes in Step S312), the control section performs a process of Step S314.

On the other hand, when the specimen container T is not detected in Step S309 (No in Step S309), the control section 32 moves the sample rack L to the left by one specimen direction (Step S313) and performs the process of Step S314. In Step S314, the control section 32 determines whether i is equal to or greater than 10 (Step S314). When i is less than 10 (No in Step S314), the control section increments i by 1 (Step S315) and returns the process to Step S309.

In Step S314, when i is equal to or greater than 10 (Yes in Step S314), the control section 32 controls the transport mechanism 31 so as to bring the sample rack L to a conveyance position for conveying the sample rack L (Step S316). After that, the control section 32 performs a process of Step S318.

On the other hand, in Step S306, when the designated transport line instruction data included in the conveyance preparation instruction data indicates the skip line L2, that is, when the object transport line to be used is the skip line L2 ("skip line L2" in Step S306), the control section 32 controls the transport mechanism 31 so as to move the sample rack L on the skip line L2 to thereby bring the sample rack to a conveyance position for conveying the sample rack L (Step S317). After that, the control section 32 performs the process of Step S318.

In Step S318, the control section 32 transmits conveyance request data including the rack ID assigned to the sample rack L to the system control apparatus 8 (Step S318). Then, the control section 32 stands by to receive conveyance instruction data from the system control apparatus 8 (No in Step S319). When having received the conveyance instruction data (Yes in Step S319), the control section drives the stepping motor 321b to convey the sample rack L to the adjacent specimen transport apparatus 3 (Step S320) and transmits conveyance completion data to the system control apparatus 8 (Step S321). In addition, the control section 32 completes the process.

<Operation of Blood Cell Analyzing Apparatus 5>

Next, an operation of the blood cell analyzing apparatus 5 will be described. The information processing unit 52 controls the operation of the measuring units 51, 51 and 51 so as to perform the specimen measurement and analyzes measuring data obtained by the measurement.

Figure 29B:
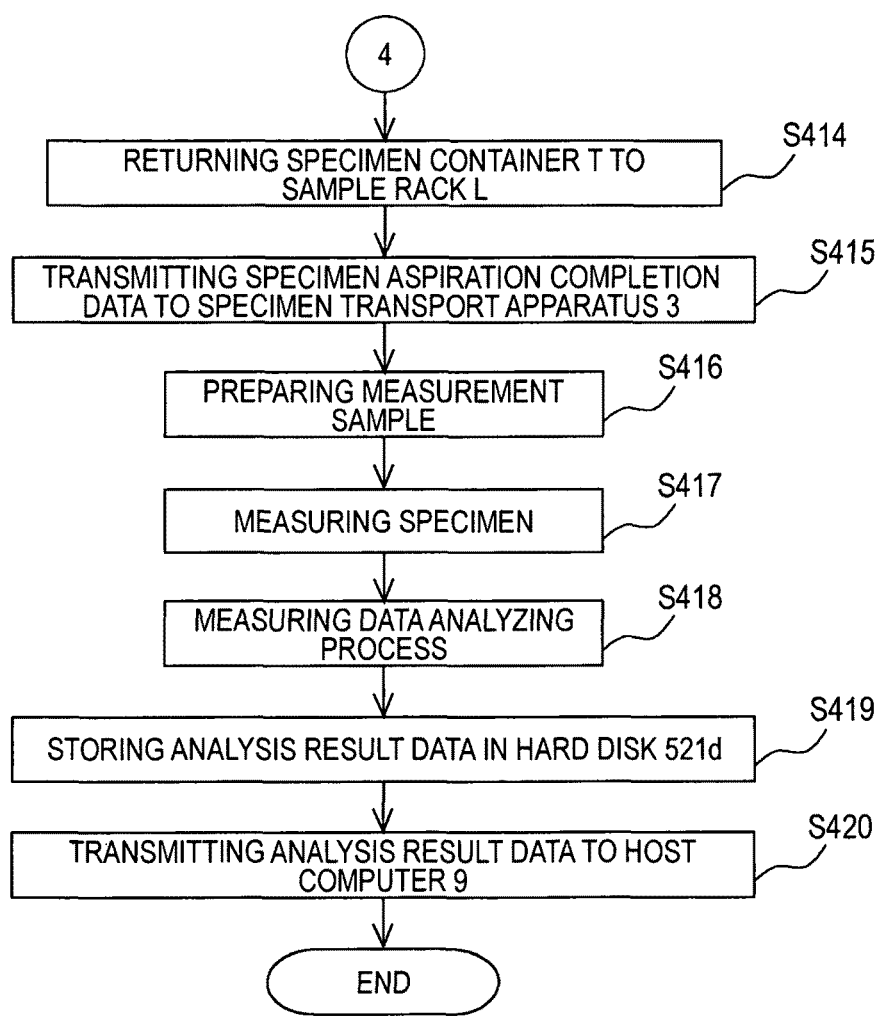
FIG. 29B is a flowchart (second half) showing the procedure of the specimen analyzing operation of the blood cell analyzing apparatus according to the first embodiment.

FIGS. 29A and 29B are flowcharts showing the procedure of the specimen analyzing operation of the blood cell analyzing apparatus 5 according to this embodiment. First, the information processing unit 52 receives aspiration instruction data transmitted from the control section 32 of the specimen transport apparatus 3 (Step S401). In the CPU 521a, a process of Step S402 is invoked when an event in which the aspiration instruction data is received occurs. The aspiration instruction data includes a measuring unit ID of the measuring unit 51 which is an object to be operated and a container type ID corresponding to the type of the specimen container T which is an object.

In Step S402, the CPU 521a controls the specimen container transport section 515 so as to pull the specimen container T at the supply position 35c out of the sample rack L (Step S402) and controls the hand section 515a so as to oscillate the specimen container T to thereby stir the specimen in the specimen container (Step S403). Next, the CPU 521a controls the hand section 515a so as to set the specimen container T in the specimen container setting section 515b (Step S404) and further controls the specimen container transport section 515 so as to transport the specimen container T to the bar-code reading position 516a (Step S405). Next, the CPU 521a reads the specimen bar-code of the specimen container T by the bar-code reading section 516 to obtain the specimen ID (Step S406). Further, the CPU 521a transmits order request data including the specimen ID to the host computer 9 via the communication interface 521g (Step S407) so as to make an inquiry of measuring order. After that, the CPU 521a stands by to receive a measuring order (No in Step S408). When the measuring order transmitted from the host computer 9 is received by the communication interface 521g of the information processing unit 52 (Yes in Step S408), the received measuring order is stored in the hard disk 521d (Step S409).

Moreover, the CPU 521a determines a descent amount (movement distance) of the specimen aspirating section 511 corresponding to the type of the specimen container (Step S410). As described above, the descent amount table TBL1 is provided in the hard disk 521d, and the descent amount is set by using the descent amount table TBL1. In this process, the CPU 521a extracts the container type ID from the aspiration instruction data and obtains the descent amount corresponding to the container type ID from the descent amount table TBL1. In this manner, the descent amount of the specimen aspirating section 511 is determined.

Next, the CPU 521a controls the specimen container transport section 515 so as to transport the specimen container T to the aspiration position (Step S411) and controls the specimen aspirating section 511 so as to lower the aspiration tube 511a by the determined descent amount (Step S412). In this manner, the movement distance of the aspiration tube 511a into the specimen container T (insertion amount of the aspiration tube 511a from the upper end of the cap section CP) is controlled and thus the aspiration tube 511a can be lowered to a suitable position for the type of the specimen container T. Accordingly, it is possible to suppress the occurrence of aspiration failures such as air aspiration due to the movement distance of the aspiration tube 511a being too short or jabbing of the aspiration tube 511a into the inner bottom surface of the specimen container T. Next, the CPU 521a controls the specimen aspirating section 511 so as to aspirate the specimen from the specimen container T in an amount necessary for the measuring items included in the stored measuring order (Step S413). After completing the aspiration of the specimen, the CPU 521a controls the specimen container transport section 515 so as to return the specimen container T to the sample rack L (Step S414) and transmits specimen aspiration completion data to the specimen transporting apparatus 3 which is transporting the sample rack L (Step S415). Accordingly, the sample rack L is transported by the rack transport section 35 as described above.

Furthermore, the CPU 521a controls the sample preparing section 512 so as to prepare a measurement sample in accordance with the measuring items (Step S416) and supplies the measurement sample to the detecting section 513 so as to perform the specimen measurement by the detecting section 513 (Step S417). In this manner, the CPU 521a obtains measuring data output from the detecting section 513. The CPU 521a performs a process of analyzing the measuring data (Step S418), classifies the blood cells included in the specimen and counts the number of blood cells for each type so as to create a scattergram in which the classified blood cells are color-coded for each type. The analysis result data generated by the measuring data analyzing process is stored together with the patient information and the like included in the measuring order in the hard disk 521d (Step S419) and is transmitted to the host computer 9 (Step S420). The host computer 9 integrates the analysis result data and the above-described measuring order and stores the result thereof in the hard disk. After the process of Step S420, the CPU 521a completes the process.

<Operation of Specimen Transport Apparatus 301>

The sample rack L delivered from the specimen transport apparatus 3 positioned on the downmost-stream side in the transport direction is fed to the rack slider 303. Although a detailed description is omitted, the rack slider 303 receives an instruction from the system control apparatus 8 and delivers the sample rack L to the measuring line 302a or the skip line 302b of the conveyor 302. When the sample rack L is conveyed to the measuring line 302a, the control section of the conveyor 302 operates the measuring line 302a so as to transport the sample rack L so that the specimen container T which is a smear preparing object is positioned at a supply position for supplying the specimen to the smear preparing apparatus 6. Herein, the control section of the specimen transport apparatus 301 transmits aspiration instruction data including the container type ID to the smear preparing apparatus 6. The control section 65 of the smear preparing apparatus 6 obtains the descent amount corresponding to the container type from the descent amount table TBL2 and lowers the aspiration tube of the dispensing section 61 by the descent amount to thereby aspirate the specimen. After the aspiration is completed, the specimen container T is returned to the sample rack L. After the supplying of the specimen to the smear preparing apparatus 6 is completed, the measuring line 302a is further driven so as to convey the sample rack L to the processed specimen accommodating apparatus 4. In addition, when the sample rack L is conveyed to the skip line 302b, the control section of the conveyor 302 operates the skip line 302b so as to transport the sample rack L on the skip line 302b to thereby convey the sample rack to the processed specimen accommodating apparatus 4.

<Operation of Processed Specimen Accommodating Apparatus 4>

The sample rack L delivered from the specimen transport apparatus 301 is fed to the processed specimen accommodating apparatus 4. The processed specimen accommodating apparatus 4 transports the sample rack L on the rack placing section and accommodates the sample rack.

By employing the above configuration, the type of the specimen container is determined on the basis of an image of the cap section of the specimen container, which is not affected by the presence or absence of the bar-code label adhered to the specimen container and the specimen amount in the specimen container, and thus the type of the specimen container can be accurately determined by image processing. Accordingly, the descent amount of the aspiration tube 511a suitable for the type of the specimen container is determined and the movement distance of the aspiration tube 511a into the specimen container can thus be controlled in accordance with the type of the specimen container.

In addition, the characteristic information includes dimension and color information, which indicates the characteristics of the cap section of the specimen container, of the cap section, and the type of the specimen container is determined on the basis of the dimensions and color of the cap section. Since the specimen containers of each type have a dedicated characteristic cap section, accuracy of the determination of the specimen container type is improved.

The configuration has been employed, in which the characteristic information, which is extracted from an image, of the specimen container is compared with the reference characteristic information registered in the specimen container table TBL3 so as to determine the type of the specimen container to thereby obtain the descent amount corresponding to the container type ID of the determined type of the specimen container from the descent amount table TBL1. Accordingly, only by adding reference characteristic information of a new type of specimen container to the specimen container table TBL3 and adding the descent amount corresponding to the type of the specimen container to the descent amount table TBL1, the system can easily deal with the new type of specimen container.

The configuration has been employed in which the descent amount tables TBL1 and TBL2 are individually provided in the blood cell analyzing apparatus 5 and the smear preparing apparatus 6. In the blood cell analyzing apparatus 5 and the smear preparing apparatus 6, a descent amount of the aspiration tube varies even in the specimen containers of the same type. However, by employing the above configuration, individual appropriate descent amounts can be set in the blood cell analyzing apparatus 5 and the smear preparing apparatus 6. When another specimen processing apparatus is added to the system, a descent amount table suitable for a specimen dispensing mechanism of this specimen processing apparatus is provided in the specimen processing apparatus, so more specimen processing apparatuses can be easily added without a change in the configuration of the system control apparatus 8 and the like.

Since the cap section CP of the specimen container T accommodated in the sample rack L protrudes from an upper face of the sample rack L, it is not necessary to pull the specimen container T out of the sample rack L to image the cap section CP. Accordingly, it is not necessary to provide a mechanism for pulling the specimen container T out of the sample rack L, and this suppresses the system from becoming more complicated and increasing in cost.

When a specimen container of an unknown type or a specimen container with no cap section is put, such a specimen container is automatically detected and accommodated in the rack accommodating section 221 of the specimen container accommodating unit 22. Accordingly, while continuously performing another specimen process by using the specimen processing system 1, the operator can take appropriate action, such as replacing the specimen from the specimen container of an unknown type with a specimen container suitable for the system or mounting a cap section on the specimen container. In addition, breakdown of the apparatus, which occurs by jabbing the aspiration tube into the bottom surface of the specimen container of an unknown type, is prevented, and pollution due to spilling of the specimen, which occurs by transport of the specimen container with no cap section, is prevented.

When a specimen container type error or a specimen container cap error is detected, the stored rack list screen and the detailed information screen are displayed on the liquid crystal display section 227 of the specimen container accommodating unit 22, and thus the operator can easily learn that such an error has occurred. Moreover, it can be easily confirmed which specimen container T in which sample rack L has the above error.

Since the above-described detailed information screen performs a display operation so as to specify which kind of error is generated, the operator can specify which kind of abnormality was generated with a simple confirmation of the detailed information screen displayed on the liquid crystal display section 227. Accordingly, it is possible to easily and rapidly judge which action is required.

Moreover, the rack re-putting section 231 is provided in the specimen delivery unit 23 following the specimen container accommodating unit 22. Accordingly, when although the sample rack is determined not to be provided for the measurement for the moment, all the specimens accommodated in the sample rack L are made measurable with an operation of the user (for example, specimen replacement to a proper specimen container, mounting of a cap section, and the like), the operator can put the sample rack L into the rack re-putting section 231 of the specimen delivery unit 23, not into the specimen putting unit 21. Accordingly, it is not necessary to re-read the specimen IDs of the specimens in the sample rack L by the specimen bar-code reader 21b and thus this improves system process efficiency.

Second Embodiment

This embodiment relates to a specimen processing apparatus which images a label section having a certain color and a certain size, corrects characteristic information obtained from an image of a cap section of a specimen container on the basis of the image of the imaged label section, and discriminates the type of the specimen container on the basis of the characteristic information after the correction.

[Configuration of Specimen Processing System]

Figure 30:
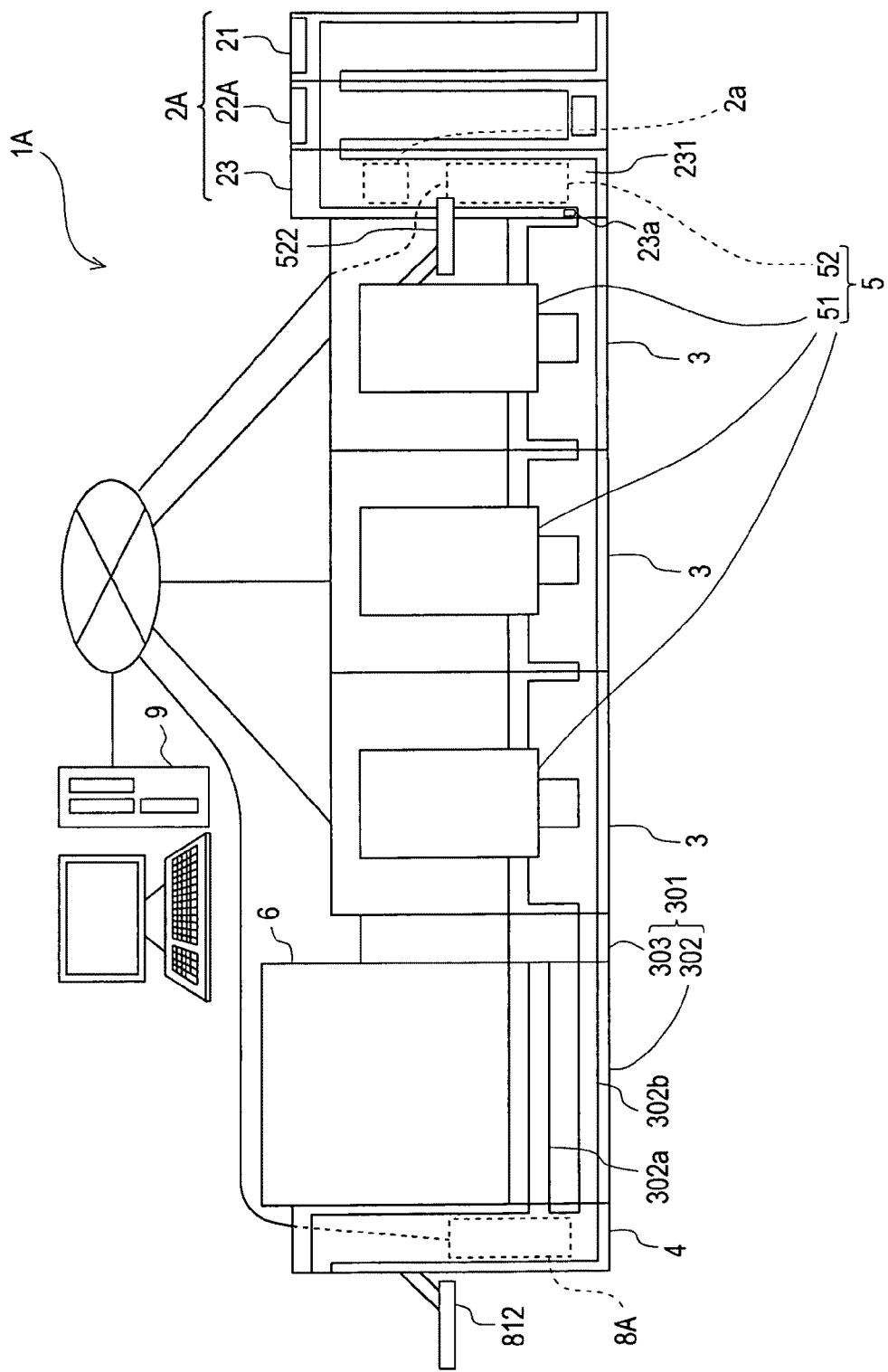
FIG. 30 is a schematic plan view showing the entire configuration of a specimen processing system according to a second embodiment.

FIG. 30 is a schematic plan view showing the entire configuration of a specimen processing system according to this embodiment. As shown in FIG. 30, a specimen processing system 1A according to this embodiment includes a specimen putting apparatus 2A and a system control apparatus 8A. The specimen putting apparatus 2A includes a specimen container accommodating unit 22A. Since the other configurations of the specimen processing system 1A according to this embodiment are the same as the configurations of the specimen processing system 1 according to the first embodiment, the same constituent elements will be denoted by the same reference numbers and a description thereof will be omitted.

Figure 31:
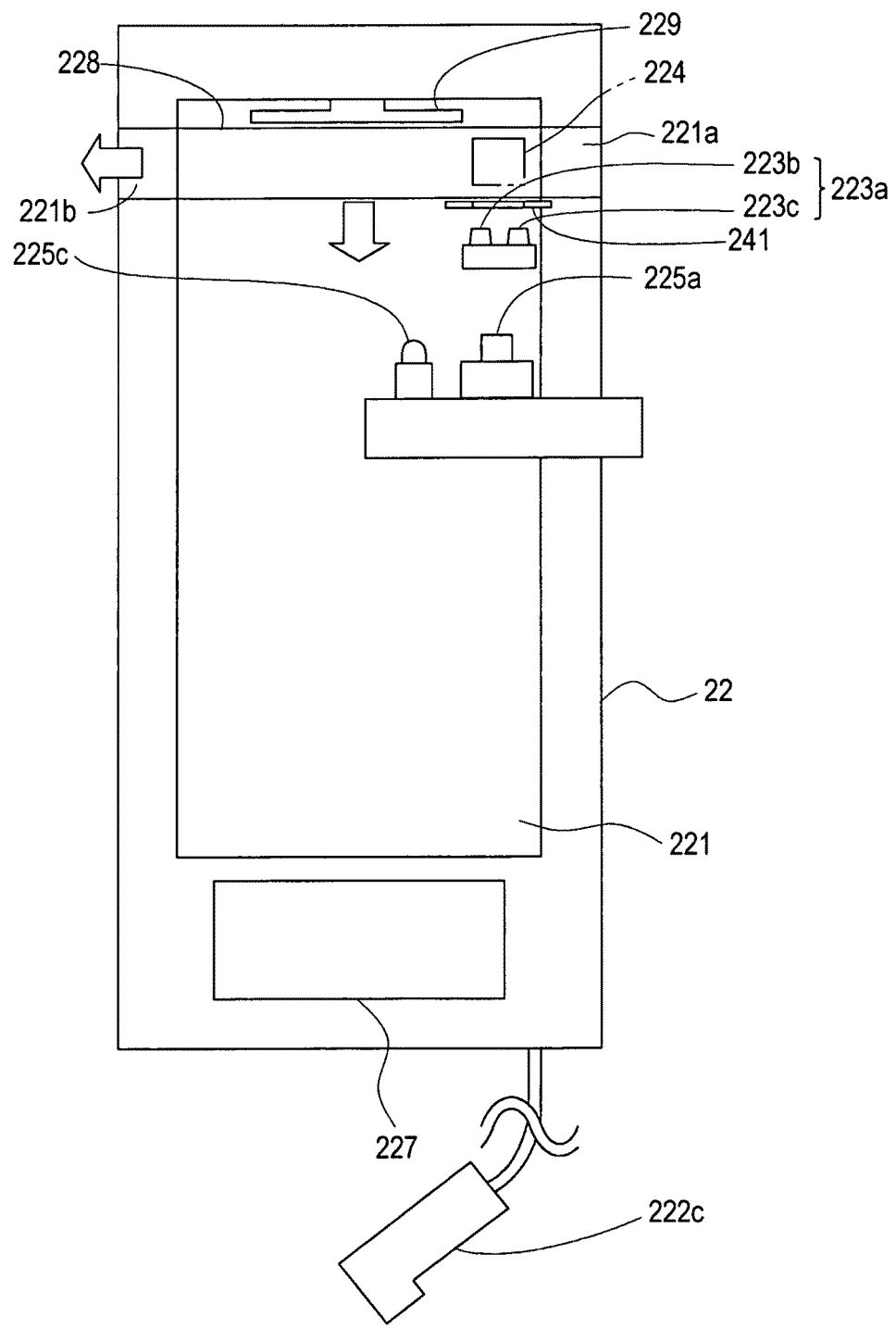
FIG. 31 is a plan view showing the configuration of a specimen container accommodating unit according to the second embodiment.

FIG. 31 is a plan view showing the configuration of the specimen container accommodating unit 22A according to this embodiment. In the specimen container accommodating unit 22A, a color bar 241 is provided near the imaging position 224. The color bar 241 does not interfere with the transport of the sample rack L by the transport belt 228 and is provided so that a part thereof (a part including a label section 242 to be described later) falls within an imaging range of the camera 225a.

Figure 32:
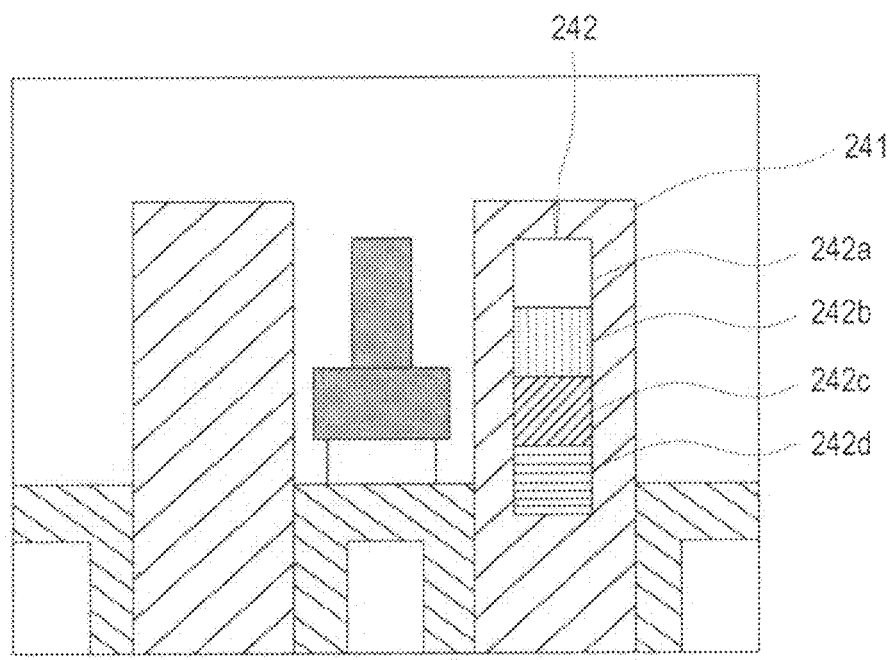
FIG. 32 is a diagram illustrating an imaging range of a camera according to the second embodiment.

FIG. 32 is a diagram illustrating the imaging range of the camera 225a according to this embodiment. As shown in the drawing, the camera 225a is disposed so that a cap section CP of a specimen container T, which is held in the sample rack L and positioned at the imaging position 224, is positioned at the center of the imaging range of the camera 225a. When viewed from the camera 225a, the color bar 241 is disposed on the right side of the specimen container T positioned at the imaging position 224. Since a part (label section 242) of the color bar 241 also falls within the imaging range, a part (label section 242) of the color bar 241 is simultaneously imaged when the specimen container T positioned at the imaging position 224 is imaged by the camera 225a.

The color bar 241 has an erected rectangular parallelepiped plate shape, and its front face (face opposed to the camera 225a) is provided with the label section 242 which is a reference for correcting cap characteristic information to be described later. The label section 242 is divided into 4 areas which are a white area 242a, a red area 242b, a green area 242c and a blue area 242d. A length of the label section 242 in a vertical direction is accurately defined. In addition, tone, intensity and brightness of the white color of the white area 242a are previously defined, and similarly, tones, intensities and brightnesses of the red color of the red area 242b, the green color of the green area 242c and the blue color of the blue area 242d are previously defined. Accordingly, label sections 242 in two specimen processing systems 1A have hardly any individual difference therebetween and thus have generally the same length and color.

Figure 33:
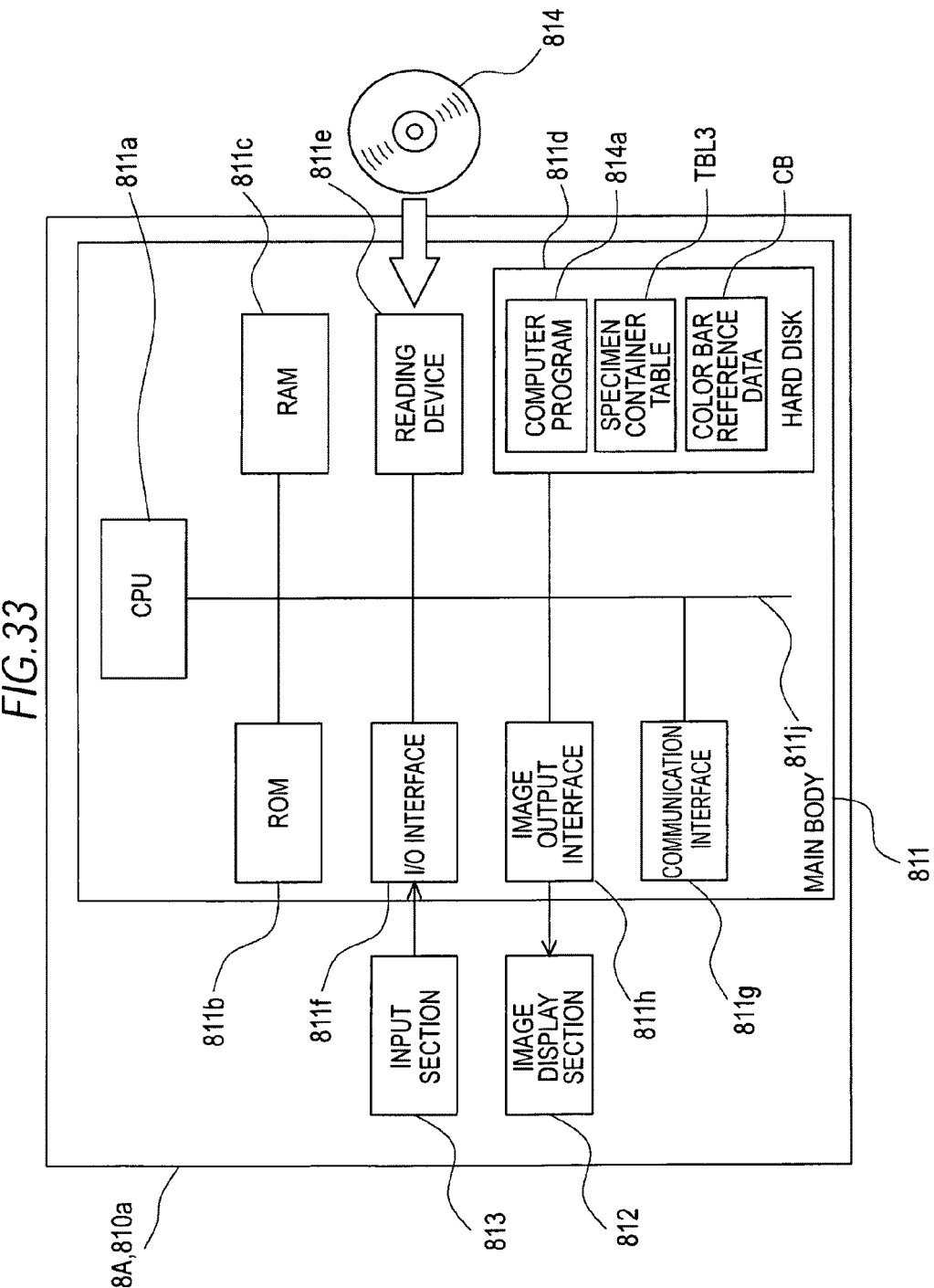
FIG. 33 is a block diagram showing the configuration of a system control apparatus according to the second embodiment.

FIG. 33 is a block diagram showing the configuration of the system control apparatus 8A according to this embodiment.

The system control apparatus 8A is composed of a computer and controls the entire specimen processing system 1A.

The system control apparatus 8A is realized by a computer 810a. AS shown in FIG. 33, the computer 810a includes a main body 811, an image display section 812 and an input section 813. The main body 811 includes a CPU 811a, a ROM 811b, a RAM 811c, a hard disk 811d, a reading device 811e, an I/O interface 811f, a communication interface 811g and an image output interface 811h. The CPU 811a, ROM 811b, RAM 811c, hard disk 811d, reading device 811e, I/O interface 811f, communication interface 811g and image output interface 811h are connected to each other by a bus 811j.

In the hard disk 811d, various computer programs for execution by the CPU 811a, such as an operating system and an application program, and data which are used to execute the computer programs are installed. A system control program 814a to be described later is also installed in the hard disk 811d.

Further, a specimen container table TBL3 which is used to discriminate the types of the specimen containers is provided in the hard disk 811d. Since the configuration of the specimen container table TBL3 is the same as that described in the first embodiment, a description thereof will be omitted. Moreover, a color bar reference data CB is stored in the hard disk 811d. The color bar reference data CB includes the length of the label section 242 of the color bar 241 and color information of the color areas 242a, 242b, 242c and 242d. That is, the color bar reference data CB includes information including L2, the number of pixels in a vertical direction in the partial image of the label section 242 included in the image captured by the camera 225a, a luminance value (hereinafter, referred to as "reference luminance") LU2 which is a reference for the partial image of the white area 242a, an upper limit value N and a lower limit value M of the luminance value of the partial image of the white area 242a, a R value (hereinafter, referred to as "reference R value") r2 which is a reference for the partial image of the red area 242b, a G value (hereinafter, referred to as "Reference G value") g2 which is a reference for the partial image of the green area 242c, and a B value (hereinafter, referred to as "reference B value") b2 which is a reference for the partial image of the blue area 242d. The upper limit value N and the lower limit value M indicate an upper limit value and a lower limit value of an average luminance of the partial image of the white area 242a included in the image captured by the camera 225a when the camera 225a and a white LED 225c are normal. That is, when an average luminance value of the partial image of the white area 242a included in the image captured by the camera 225a is more than the upper limit value N or less than the lower limit value M, it is possible to determine that the camera 225a or the white LED 225c has an abnormality.

The reading device 811e is composed of a flexible disk drive, a CD-ROM drive, a DVD-ROM drive or the like and can read the computer program or data recorded in a portable recording medium 814. In the portable recording medium 814, the system control program 814a for prompting the computer to function as the system control apparatus 8A is stored. The computer 810a can read the system control program 814a from the portable recording medium 814 and install the system control program 814a in the hard disk 811d.

The I/O interface 811f is composed of, for example, a serial interface such as USB, IEEE1394 or RS-232C, a parallel interface such as SCSI, IDE or IEEE 1284, and an analog interface including a D/A converter and an A/D converter. The input section 813 composed of a keyboard and a mouse is connected to the I/O interface 811f and a user uses the input section 813 so as to input data to the computer 810a.

The communication interface 811g is an Ethernet (registered trade name) interface. The communication interface 811g is connected to the specimen putting apparatus 2A, the specimen transport apparatus 3, the processed specimen accommodating apparatus 4, the information processing unit 52 and the host computer 9 via a LAN. Via the communication interface 811g, the computer 810a can send and receive data to and from the above respective apparatuses connected to the LAN by using a predetermined communication protocol.

Since the other configurations of the system control apparatus 8A are the same as the configurations of the system control apparatus 8 described in the first embodiment, a description thereof will be omitted.

[Operation of Specimen Processing System]

Next, an operation of the specimen processing system 1A according to this embodiment will be described. As described above, in the specimen processing system 1A according to this embodiment, the camera 225a images the label section 242 of the color bar 241 as well as the cap section CP of the specimen container T when the specimen container T is positioned at the imaging position 224 of the specimen container accommodating unit 22A. In order to eliminate discrimination error occurring due to individual differences between the devices, such as light intensity of the white LED 225c used as a light source, light-receiving sensitivity of the camera 225a and mounting position of the camera 225a in a specimen container type discriminating process, the specimen processing system 1A corrects the characteristic information by using a portion of the label section 242 in the image captured by the camera 225a. Hereinafter, the specimen container type discriminating process of the system control apparatus 8A according to this embodiment will be described.

Figure 34:
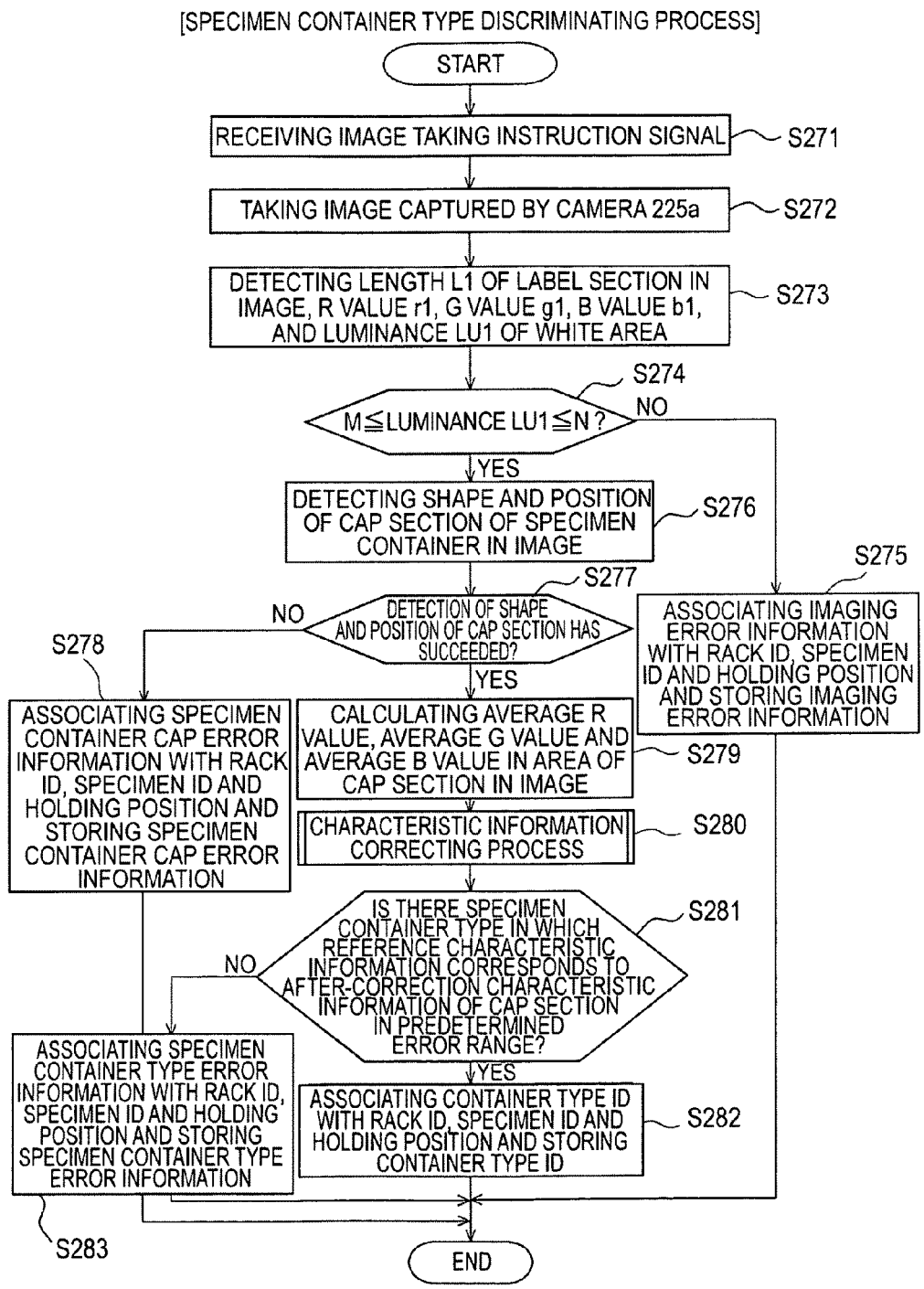
FIG. 34 is a flowchart showing the flow of a specimen container type discriminating process of the system control apparatus according to the second embodiment.

FIG. 34 is a flowchart showing the flow of the specimen container type discriminating process of the system control apparatus 8A according to this embodiment. As shown in FIG. 34, in the CPU 811a of the system control apparatus 8A, a process of Step S272 is invoked when an event in which an image taking instruction signal transmitted from the specimen putting apparatus 2 is received by the system control apparatus 8A occurs (Step S271).

In Step S272, the CPU 811a takes an image captured by the camera 225a at that time point (Step S272). The entire cap section CP of the specimen container T and the entire label section 242 of the color bar 241 are included in the image. Next, the CPU 811a detects the label section 242 by using a method such as a luminance value differentiating process in a portion including the label section 242 in the image and obtains a length (the number of pixels in a vertical direction) L1 of the label section 242, an average luminance value LU1 of the partial image of the white area 242a, an average R value r1 of the partial image of the red area 242b, an average G value g1 of the partial image of the green area 242c and an average B value b1 of the partial image of the blue area 242d (Step S273).

Next, the CPU 811a compares the obtained average luminance value LU1 of the partial image of the white area 242a with the upper limit N and the lower limit M included in the color bar reference data CB so as to determine whether the expression $M \leq LU1 \leq N$ is satisfied (Step S274). From this process, it is determined whether the state of the imaging by the camera 225a is normal. That is, when the expression $M \leq LU1 \leq N$ is satisfied, it can be judged that both of the sensitivity of the camera 225a and the light intensity of the white LED are normal, and when the expression $M \leq LU1 \leq N$ is not satisfied, it can be judged that the sensitivity of the camera 225a or the light intensity of the white LED is not normal. Herein, when the expression M≤LU1≤N is not satisfied (No in Step S274), the CPU 811*a* associates imaging error information with a rack ID, a specimen ID and a holding position, stores the information in the hard disk 811*d* (Step S275) and completes the process. When the imaging error information is stored, "imaging error" (not shown) associated with the holding position is displayed in a detailed information screen (see FIG. 21 for reference) of the sample rack L of the specimen container accommodating unit 22A. By confirming the display of the imaging error, a user or a service man can recognize that there is an abnormality in the sensitivity of the camera 225*a* or the light intensity of the white LED, and necessary measures can be taken, such as adjustments in the sensitivity of the camera 225*a*, adjustments in the light intensity of the white LED 225*c* and replacement of the white LED 225*c*.

In Step S274, when the expression M≤LU1≤N is satisfied (Yes in Step S274), the CPU 811*a* detects a shape and a position of the cap section CP of the specimen container T in the taken image (Step S276). Since this process is the same as the process of Step S213 described in the first embodiment, a description thereof will be omitted.

Next, the CPU 811*a* determines whether the detection of the shape and the position of the cap section of the specimen container by the above-described process has succeeded (Step S277). When the detection of the shape and the position of the cap section has failed (No in Step S277), the CPU associates specimen container cap error information indicating that the specimen container has no cap section with the rack ID of the sample rack L, the specimen ID of the specimen and the holding position of the specimen container T in the sample rack L, stores the information in the hard disk 811*d* (Step S278), and completes the process.

On the other hand, when the detection of the shape and the position of the cap section has succeeded (Yes in Step S277), the CPU 811*a* uses the positions of the upper, lower, left and right ends of the cap section obtained as described above, and as well as the above positions, the position of a stage section and the positions of the left and right ends of a small diameter section in the case of a two-stage cap, to specify an area of the cap section in the image, and then obtains R, G and B values of pixels in this area. The CPU calculates an average value of each of the R, G and B values (Step S279).

Next, the CPU 811*a* performs a characteristic information correcting process for correcting the characteristic information of the specimen container obtained by the above-described process, that is, the length of the specimen container, the shape information (cap length, cap diameter, cap small diameter section length and small cap diameter) of the cap section and the color information (average value of each of the R, G and B values) of the cap section (Step S280).

Figure 35:
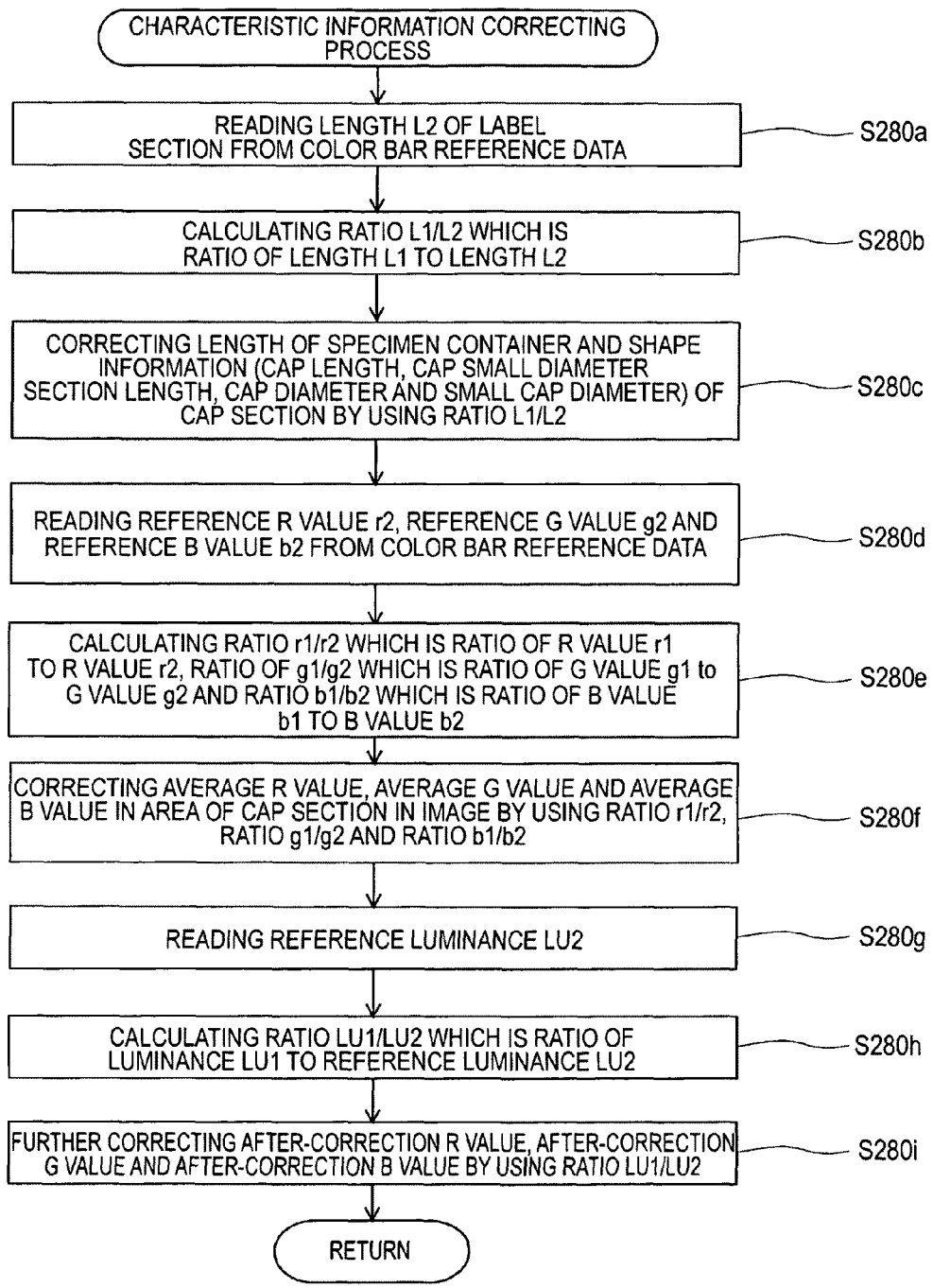
FIG. 35 is a flowchart showing the procedure of a characteristic information correcting process of the system control apparatus according to the second embodiment.

FIG. 35 is a flowchart showing the procedure of the characteristic information correcting process of the system control apparatus 8A according to this embodiment. In the characteristic information correcting process, first, the CPU 811*a* reads from the hard disk 811*d* the length L2 of the label section 242 included in the color bar reference data CB (Step S280*a*). Next, the CPU 811*a* calculates a ratio L1/L2 which is a ratio of the length L1 to length L2 (Step S280*b*). Further, the CPU 811*a* multiplies the length of the specimen container and the shape information (cap length, cap small diameter section length, cap diameter and small cap diameter) of the cap section included in the characteristic information by the ratio L1/L2 so as to correct the length of the specimen container and the shape information of the cap section included in the characteristic information (Step S280*c*).

Subsequently, the CPU 811*a* reads from the hard disk 811*d* the reference R value r2, the reference G value g2 and the reference B value b2 included in the color bar reference data CB (Step S280*d*). Further, the CPU 811*a* calculates a ratio r1/r2 which is a ratio of the average R value r1 to the reference R value r2, a ratio g1/g2 which is a ratio of the average G value g1 to the reference G value g2 and a ratio b1/b2 which is a ratio of the average B value b1 to the reference B value b2 (Step S280*e*). Moreover, the CPU 811*a* multiplies the average R value of the cap section included in the characteristic information by the ratio r1/r2, multiplies the average G value of the cap section included in the characteristic information by the ratio g1/g2 and multiplies the average B value of the cap section included in the characteristic information by the ratio b1/b2 so as to correct the color information of the cap section included in the characteristic information (Step S280*f*).

Next, the CPU 811*a* reads from the hard disk 811*d* the reference luminance LU2 included in the color bar reference data CB (Step S280*g*) and calculates a ratio LU1/LU2 which is a ratio of the luminance LU1 to the luminance LU2 (Step S280*h*). Further, the CPU 811*a* multiplies the R value, the G value and the B value after the correction, which are obtained in Step S280*f*, by the ratio LU1/LU2 so as to further correct the R value, the G value and the B value of the cap section (Step S280*i*) and returns the process to the calling address of the characteristic information correcting process.

Next, the CPU 811*a* compares the after-correction characteristic information of the specimen container obtained by the above-described process, that is, the length of the specimen container, the shape information (cap length, cap diameter, cap small diameter section length and small cap diameter) of the cap section and the color information (average value of each of the R, G and B values) of the cap section with the reference characteristic information on the various specimen containers registered in the specimen container table TBL3 so as to determine whether there is a specimen container type corresponding to the specimen container T in a predetermined error range (Step S281). When there is a specimen container type corresponding to the specimen container T in the predetermined error range (Yes in Step S281), the CPU 811*a* associates the container type ID for specifying the type of the specimen container with the rack ID of the sample rack L, the specimen ID of the specimen and the holding position of the specimen container T in the sample rack L, stores the container type ID in the hard disk 811*d* (Step S282) and completes the process. On the other hand, when there is no specimen container type corresponding to the specimen container T in the predetermined error range (No in Step S281), the CPU 811*a* associates specimen container type error information indicating that the type of the specimen container cannot be discriminated with the rack ID of the sample rack L, the specimen ID of the specimen and the holding position of the specimen container T in the sample rack L, stores the information in the hard disk 811*d* (Step S283) and completes the process.

Since the other operations of the system control apparatus 8A according to this embodiment are the same as those of the system control apparatus 8 according to the first embodiment, a description thereof will be omitted. In addition, since the other operations of the specimen processing system 1A according to this embodiment are the same as those of the specimen processing system 1 according to the first embodiment, a description thereof will be omitted.

Due to the above-described configuration, in the specimen processing system 1A according to this embodiment, the characteristic information of the cap section CP obtained by imaging the cap section CP of the specimen container T is corrected to prevent an error from being generated by the individual differences between the devices and to discriminate the type of the specimen container with higher accuracy.

Third Embodiment

This embodiment relates to a specimen processing apparatus which images a label section showing a certain color (white color), determines a threshold for a binarization process of an image, which is obtained by imaging a cap section of a specimen, on the basis of the image of the imaged label section, performs the binarization process on the image by the determined threshold, obtains characteristic information indicating characteristics of the cap section of the specimen container from the binarized image, and discriminates the type of the specimen container on the basis of the characteristic information.

[Configuration of Specimen Processing System]

Figure 36:
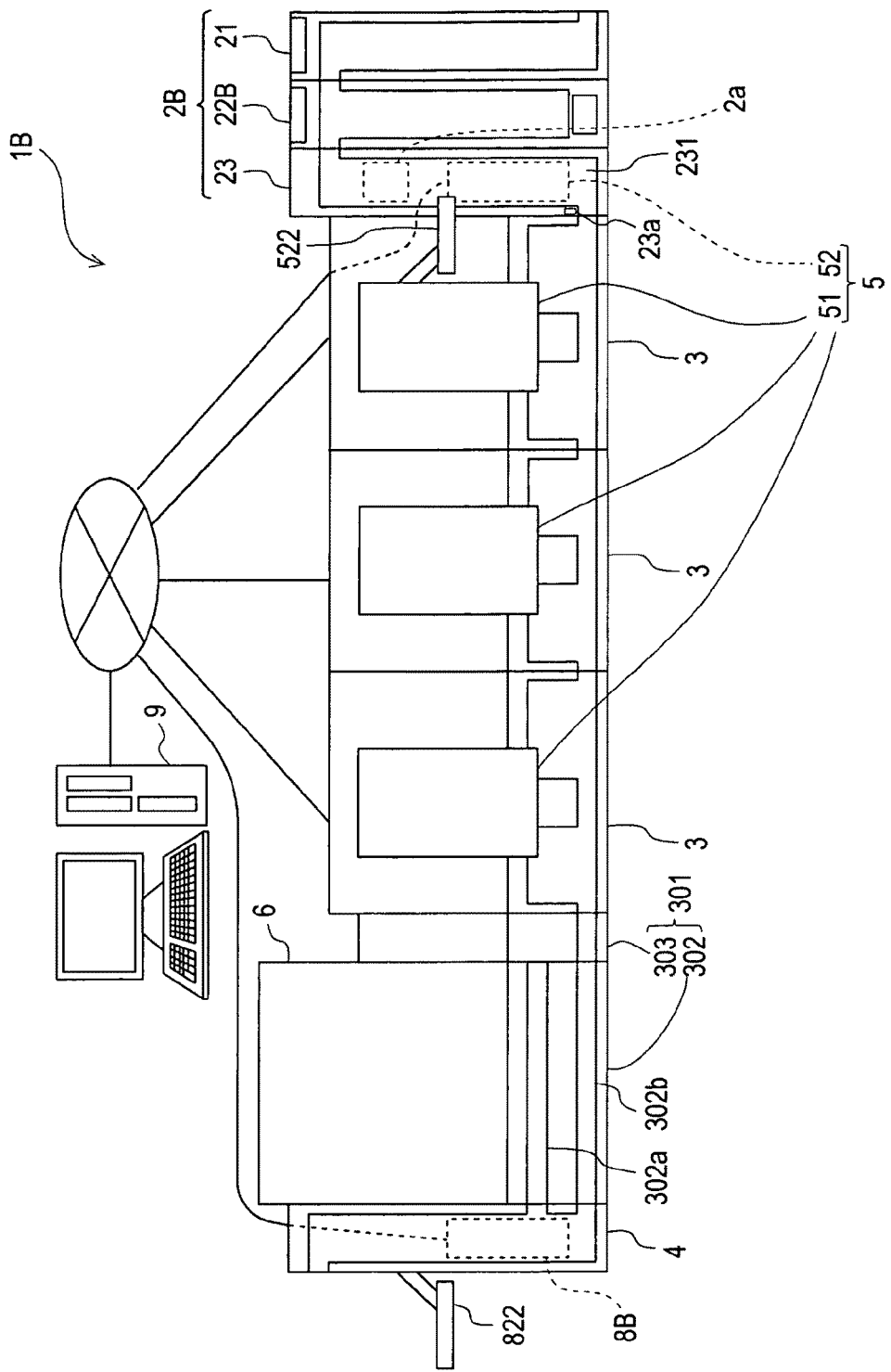
FIG. 36 is a schematic plan view showing the entire configuration of a specimen processing system according to a third embodiment.

FIG. 36 is a schematic plan view showing the entire configuration of the specimen processing system according to this embodiment. As shown in FIG. 36, a specimen processing system 1B according to this embodiment includes a specimen putting apparatus 2B and a system control apparatus 8B. The specimen putting apparatus 2B includes a specimen container accommodating unit 22B. Since the other configurations of the specimen processing system 1B according to this embodiment are the same as the configurations of the specimen processing system 1A according to the second embodiment, the same constituent elements will be denoted by the same reference numbers and a description thereof will be omitted.

Figure 37:
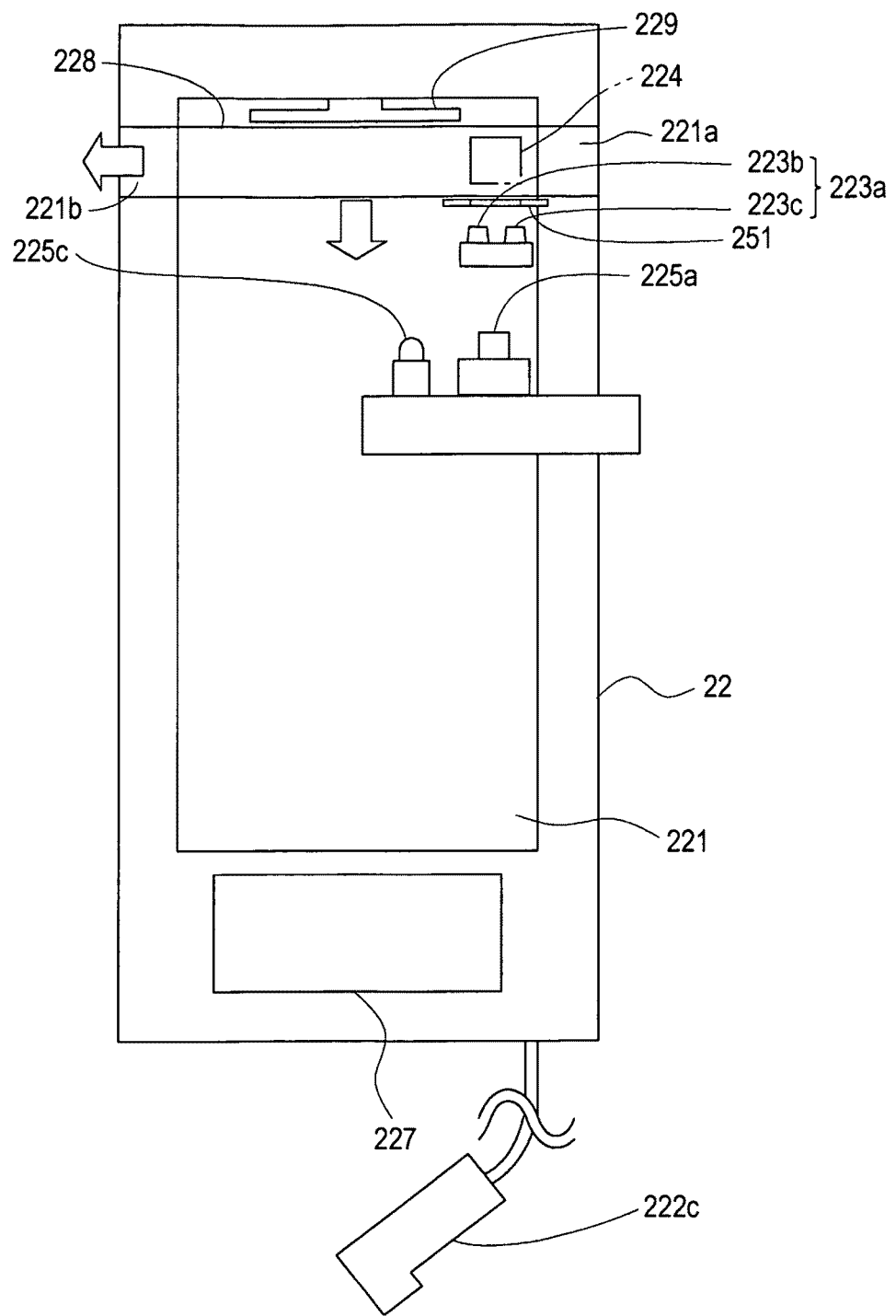
FIG. 37 is a plan view showing the configuration of a specimen container accommodating unit according to the third embodiment.

FIG. 37 is a plan view showing the configuration of the specimen container accommodating unit 22B according to this embodiment. In the specimen container accommodating unit 22B, a reference bar 251 is provided near the imaging position 224. The reference bar 251 does not interfere with the transport of the sample rack L by the transport belt 228 and is provided so that a part thereof (a part including a white section 252 to be described later) falls within an imaging range of the camera 225a.

Figure 38:
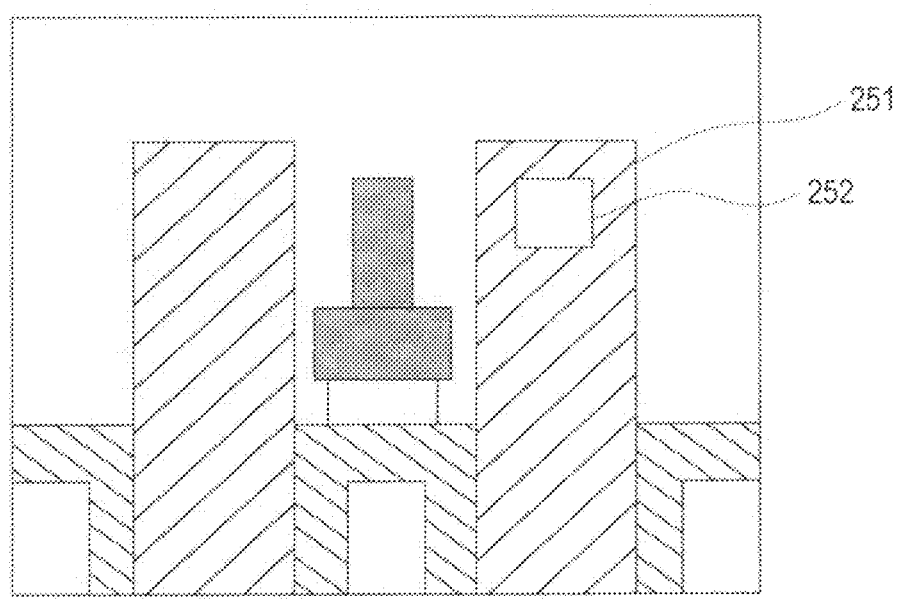
FIG. 38 is a diagram illustrating an imaging range of a camera according to the third embodiment.

FIG. 38 is a diagram illustrating the imaging range of the camera 225a according to this embodiment. As shown in the drawing, the camera 225a is disposed, so that the cap section CP of the specimen container T held in the sample rack L and positioned at the imaging position 224 is positioned at the center of the imaging range of the camera 225a. When viewed from the camera 225a, the reference bar 251 is disposed on the right side of the specimen container T positioned at the imaging position 224. Since a part (white section 252) of the reference bar 251 also falls within the imaging range, a part (white section 252) of the reference bar 251 is simultaneously imaged when the specimen container T positioned at the imaging position 224 is imaged by the camera 225a.

The reference bar 251 has an erected rectangular parallelepiped plate shape, and its front face (face opposed to the camera 225a) is provided with the white section 252 which is a reference for determining a threshold used in a binarization process to be described later. The white section 252 has a white color, the tone, the intensity and the brightness of which are previously defined. Accordingly, white sections 252 in two specimen processing systems 1B have hardly any individual difference therebetween and thus have generally the same white color.

Figure 39:
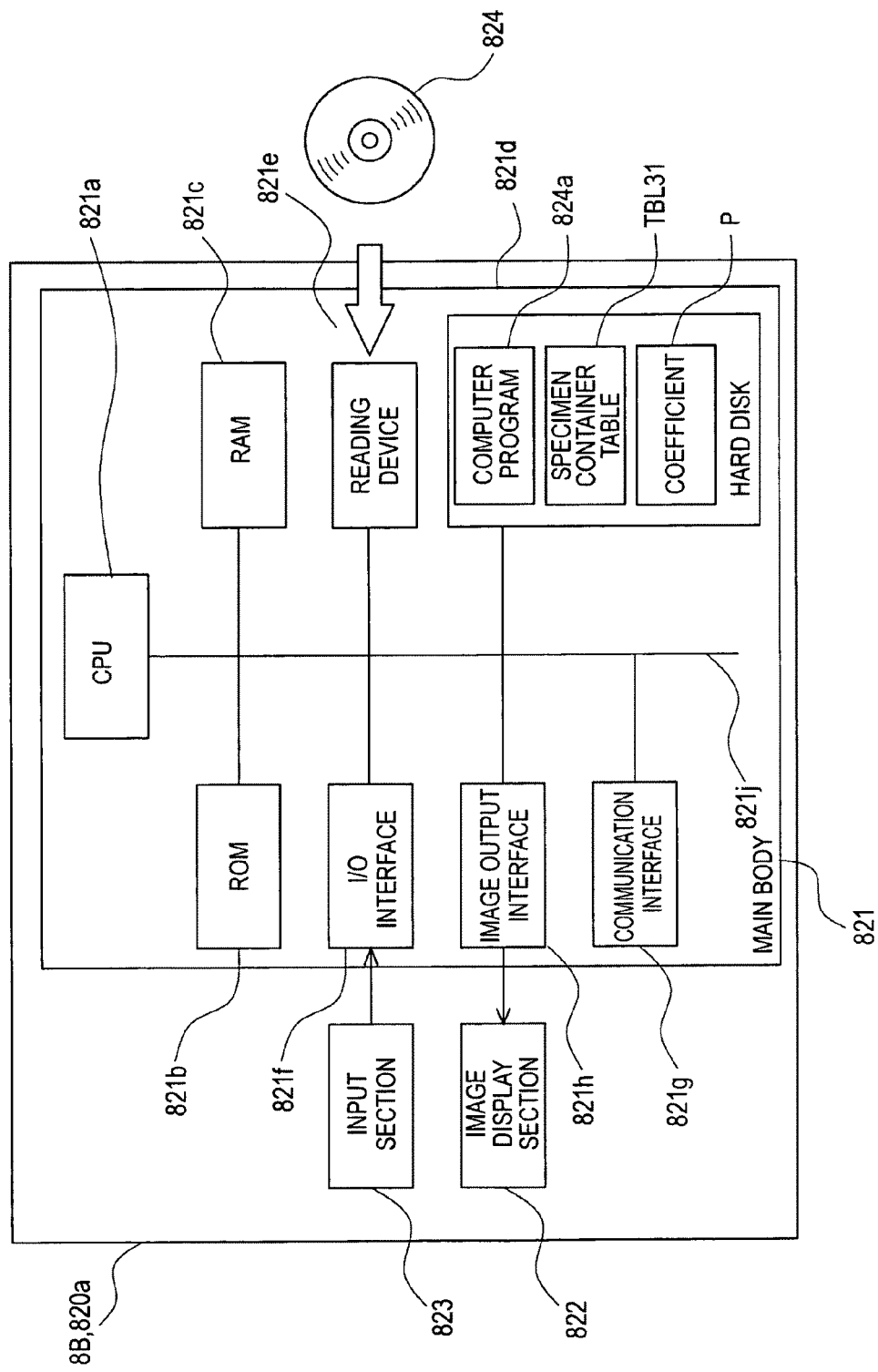
FIG. 39 is a block diagram showing the configuration of a system control apparatus according to the third embodiment.

FIG. 39 is a block diagram showing the configuration of the system control apparatus 8B according to this embodiment. The system control apparatus 8B is composed of a computer and controls the entire specimen processing system 1B.

The system control apparatus 8B is realized by a computer 820a. AS shown in FIG. 39, the computer 820a includes a main body 821, an image display section 822 and an input section 823. The main body 821 includes a CPU 821a, a ROM 821b, a RAM 821c, a hard disk 821d, a reading device 821e, an I/O interface 821f, a communication interface 821g and an image output interface 821h. The CPU 821a, ROM 821b, RAM 821c, hard disk 821d, reading device 821e, I/O interface 821f, communication interface 821g and image output interface 821h are connected to each other by a bus 821j.

In the hard disk 821d, various computer programs for execution by the CPU 821a, such as an operating system and an application program, and data, which are used to execute the computer programs, are installed. A system control program 824a to be described later is also installed in the hard disk 821d.

Further, a specimen container table TBL31 which is used to discriminate the types of the specimen containers is provided in the hard disk 821d. The specimen container table TBL31 is data having a two-dimensional table form and each row corresponds to the type of a specimen container. Each row stores reference characteristic information indicating characteristics of a specimen container. Specifically, this reference characteristic information includes a container type ID for specifying the type of a specimen container, a length (height) of the specimen container, and information indicating a shape of a cap section including a length of the cap section, a diameter of the cap section, a length of a small diameter section of a two-stage cap (cap section having two cap diameters of the small diameter section and a large diameter section) and a diameter of the small diameter section (not shown). In addition, a coefficient P is stored in the hard disk 821d. This coefficient P is a coefficient for determining a threshold which is used in a binarization process for obtaining characteristic information.

The reading device 821e is composed of a flexible disk drive, a CD-ROM drive, a DVD-ROM drive or the like and can read the computer program or data recorded in a portable recording medium 824. In the portable recording medium 824, the system control program 824a for prompting the computer to function as the system control apparatus 8B is stored. The computer 820a can read the system control program 824a from the portable recording medium 824 and install the system control program 824a in the hard disk 821d.

The I/O interface 821f is composed of, for example, a serial interface such as USB, IEEE1394 or RS-232C, a parallel interface such as SCSI, IDE or IEEE 1284, and an analog interface including a D/A converter and an A/D converter. The input section 823 composed of a keyboard and a mouse is connected to the I/O interface 821f and a user uses the input section 823 so as to input data to the computer 820a.

The communication interface 821g is an Ethernet (registered trade name) interface. The communication interface 821g is connected to the specimen putting apparatus 2B, the specimen transport apparatus 3, the processed specimen accommodating apparatus 4, the information processing unit 52 and the host computer 9 via a LAN. Via the communication interface 821g, the computer 820a can send and receive data to and from the above respective apparatuses connected to the LAN by using a predetermined communication protocol.

Since the other configurations of the system control apparatus 8B are the same as the configurations of the system control apparatus 8 described in the first embodiment, a description thereof will be omitted.

[Operation of Specimen Processing System]

Next, an operation of the specimen processing system 1B according to this embodiment will be described. In the specimen processing system 1B according to this embodiment, before the sample rack L is conveyed to the specimen container accommodating unit 22B, the camera 225a images an area including a part (portion including the white section 252) of the reference bar 251 once to obtain a background image. Then, when the specimen container T is positioned at the imaging position 224 of the specimen container accommodating unit 22B, the camera 225a images the cap section CP of the specimen container T. In order to eliminate discrimination error occurring due to individual differences between the devices, such as light intensity of a white LED 225c used as a light source, light-receiving sensitivity of the camera 225a and mounting position of the camera 225a in a specimen container type discriminating process, the specimen processing system 1B determines a threshold which is used in a binarization process by using a portion of the white section 252 in the image captured by the camera 225a and obtains a difference image between the image which is obtained by imaging the specimen container and the background image to binarize the difference image by using the threshold, and thus obtains characteristic information indicating characteristics of the cap section CP. Hereinafter, the specimen container type discriminating process of the system control apparatus 8B according to this embodiment will be described.

Before the sample rack L is conveyed to the specimen container accommodating unit 22B, the CPU 821a of the system control apparatus 8B takes the image captured by the camera 225a just one time. At this time, the specimen container T is not positioned at the imaging position 224 and the CPU 821a of the system control apparatus 8B stores this image as a background image in the hard disk 821d. In addition, from the partial image of the white section 252 included in the background image, the CPU 821a of the system control apparatus 8B obtains an average luminance value W of the portion and stores the average luminance value W in the hard disk 821d. In this state, the following specimen container discriminating process is performed.

Figure 40:
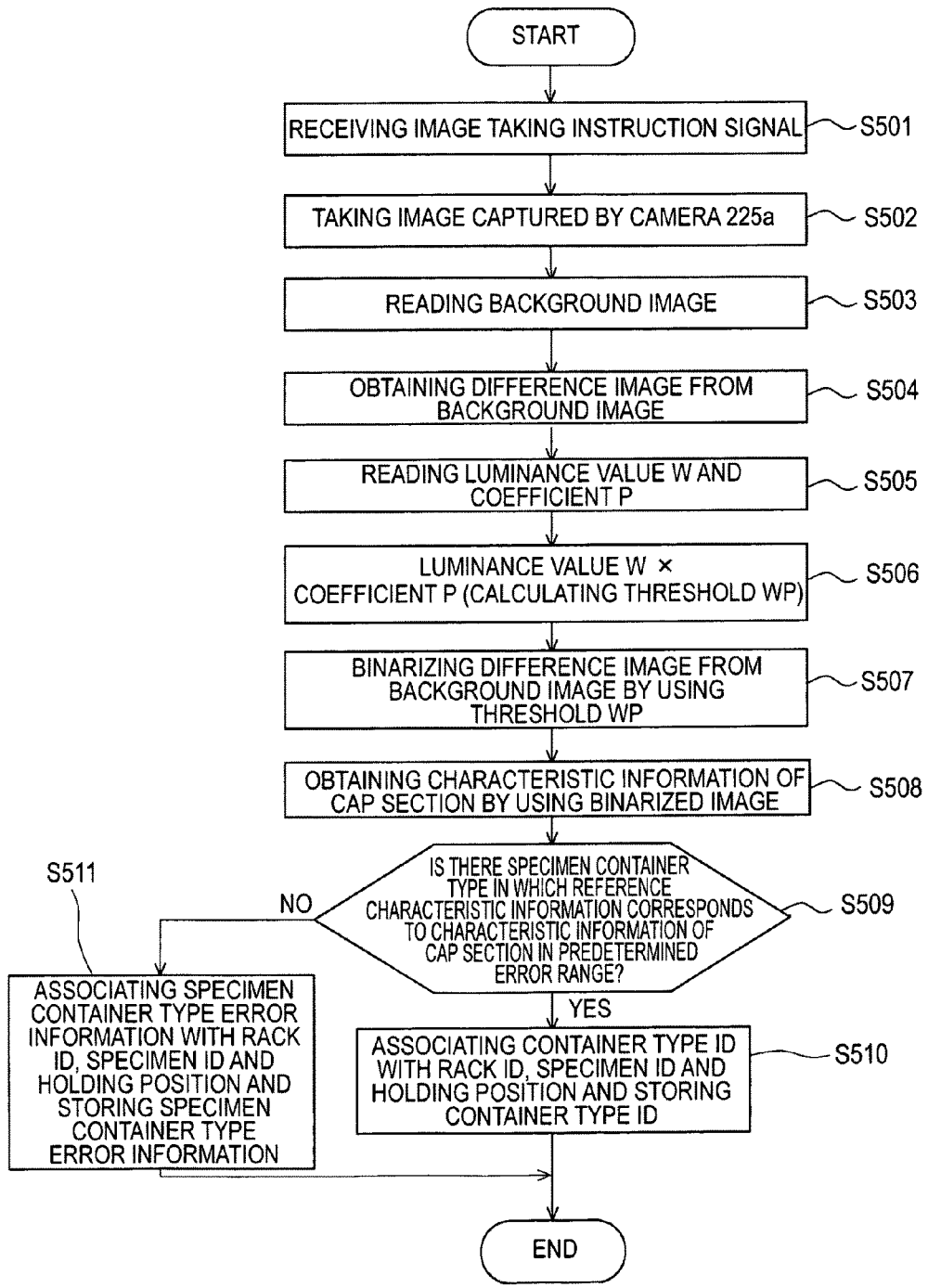
FIG. 40 is a flowchart showing the flow of a specimen container type discriminating process of the system control apparatus according to the third embodiment.

FIG. 40 is a flowchart showing the flow of the specimen container type discriminating process of the system control apparatus 8B according to this embodiment. As shown in FIG. 40, in the CPU 821a of the system control apparatus 8B, a process of Step S502 is invoked when an event in which an image taking instruction signal transmitted from the specimen putting apparatus 2B is received by the system control apparatus 8B occurs (Step S501).

In Step S502, the CPU 821a takes an image captured by the camera 225a at that time point (Step S502). The entire cap section CP of the specimen container T is included in the image. Next, the CPU 821a reads the above-described background image from the hard disk 821d (Step S503) and obtains differences between corresponding pixels of the image taken in Step S502 and the background image so as to obtain a difference image (Step S504).

Next, the CPU 821a reads the average luminance value W and the coefficient P from the hard disk 821d (Step S505). Further, the CPU 821a obtains a result of multiplication of the average luminance value W and the coefficient P as a threshold WP (Step S506).

The CPU 821a binarizes the difference image obtained in Step S504 by using the threshold WP so as to obtain a binarized image (Step S507). The difference image is an image in which the background portion, which is not required for obtaining characteristic information of the cap section, is removed from the image which is obtained by imaging the specimen container T. Accordingly, by such a binarization process, the binarized image in which the cap section CP of the specimen container T can be distinguished from the other portion can be obtained.

Next, the CPU 821a obtains the characteristic information indicating characteristics of the cap section from the above-described binarized image (Step S508). Since pixels in the area of the cap section have values different from those of pixels in another area in the binarized image, a shape of the cap section CP can be recognized in the binarized image. Accordingly, the characteristic information is information indicating the shape (a length of the cap section, a diameter of the cap section, a length of a small diameter section of a two-stage cap (cap section having two cap diameters of the small diameter section and a large diameter section) and a diameter of the small diameter section) of the cap section.

Next, the CPU 821a compares the characteristic information obtained by the above-described process, that is, the shape information (cap length, cap diameter, cap small diameter section length and small cap diameter) of the cap section with the reference characteristic information on the various specimen containers registered in the specimen container table TBL31 so as to determine whether there is a specimen container type corresponding to the specimen container T in a predetermined error range (Step S509). When there is a specimen container type corresponding to the specimen container T in the predetermined error range (Yes in Step S509), the CPU 821a associates the container type ID for specifying the type of the specimen container with the rack ID of the sample rack L, the specimen ID of the specimen and the holding position of the specimen container T in the sample rack L, stores the container type ID in the hard disk 821d (Step S510) and completes the process. On the other hand, when there is no specimen container type corresponding to the specimen container T in the predetermined error range (No in Step S509), the CPU 821a associates specimen container type error information indicating that the type of the specimen container cannot be discriminated with the rack ID of the sample rack L, the specimen ID of the specimen and the holding position of the specimen container T in the sample rack L, stores the information in the hard disk 821d (Step S511) and completes the process.

Since the other operations of the system control apparatus 8B according to this embodiment are the same as those of the system control apparatus 8 according to the first embodiment, a description thereof will be omitted. In addition, since the other operations of the specimen processing system 1B according to this embodiment are the same as those of the specimen processing system 1 according to the first embodiment, a description thereof will be omitted.

Due to the above-described configuration, in the specimen processing system 1B according to this embodiment, by using the image of the white section 252, where luminance as a reference is previously determined, as the basis for determining the threshold which is used in the binarization process, which is performed to obtain the characteristic information of the cap section CP, of the image of the cap section CP of the specimen container T, an error can be prevented from being generated by the individual differences between the devices and the type of the specimen container can be discriminated with higher accuracy.

Other Embodiments

In the above-described first to third embodiments, the specimen processing system which includes the plural measuring units 51, 51 and 51 and transports specimens to the measuring units has been described. However, the invention is not limited to this. A specimen analyzing apparatus which includes a measuring unit and a specimen transport unit and transports specimens to the measuring unit by the specimen transport unit may be used. In this case, the specimen transport unit includes a putting area in which plural sample racks accommodating specimens before analysis can be placed, a storage area in which plural sample racks accommodating specimens after analysis can be placed and a camera. The specimen processing apparatus images a cap section of a specimen container accommodated in a sample rack L in the putting area, determines the type of the specimen container from the image, lowers an aspiration tube by a descent amount corresponding to the type of the specimen container, aspirates a specimen from the specimen container and measures the specimen.

Figure 41:
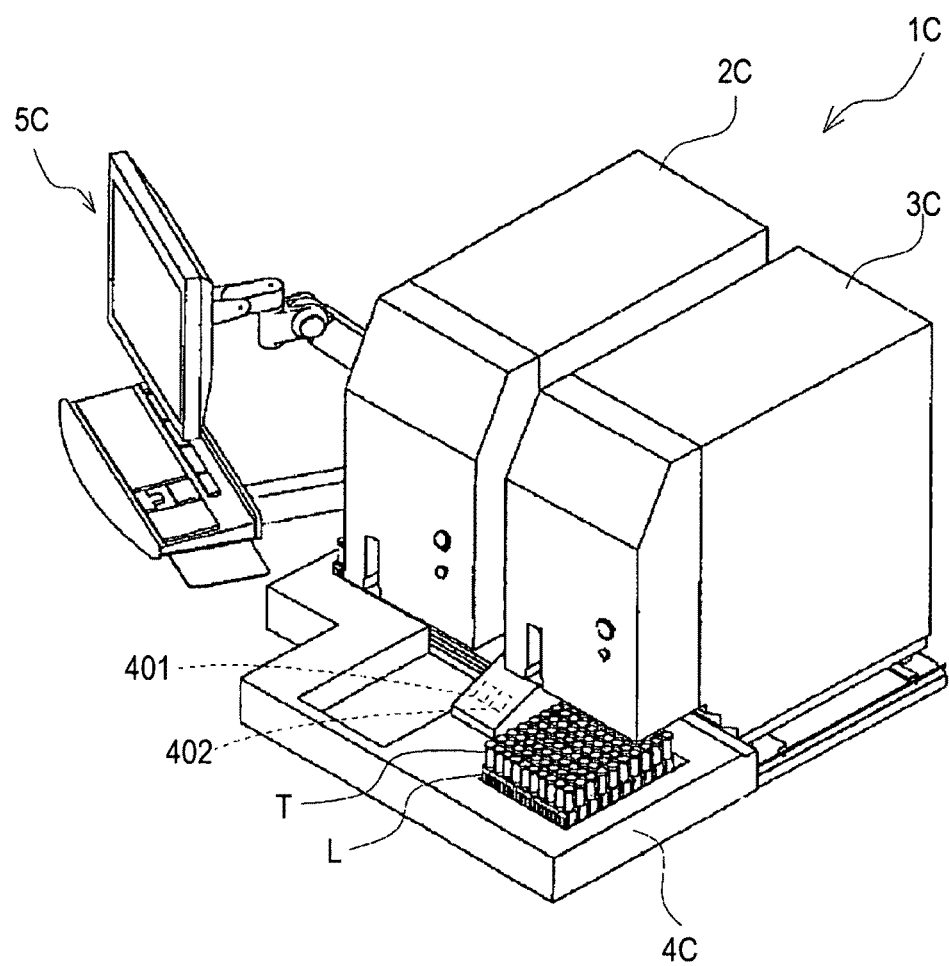
FIG. 41 is a perspective view showing an example of a specimen processing apparatus having another configuration.

FIG. 41 is a perspective view showing an example of a specimen processing apparatus having another configuration. The specimen processing apparatus of this example is a multiple blood cell analyzing apparatus detecting blood cells (white blood cells, red blood cells, platelets and the like) which are included in a blood specimen and counting the number of each kind of blood cell. As shown in FIG. 41, a specimen processing apparatus 1C includes a first measuring unit 2C, a second measuring unit 3C, a specimen transport unit 4C which is disposed in front of the first measuring unit 2C and the second measuring unit 3C, and an information processing unit 5C which can control the first measuring unit 2C, the second measuring unit 3C and the specimen transport unit 4C. The first measuring unit 2C and the second measuring unit 3C have the same configuration as that of the measuring unit 51 of the blood cell analyzing apparatus 5 according to the first to third embodiments. The specimen transport unit 4C transports a sample rack L so as to supply a specimen container T held in the sample rack L to the first measuring unit 2C and the second measuring unit 3C. Such a specimen transport unit 4C is provided with a white LED 401 as a light source and a camera 402 as an imaging section. The information processing unit 5C can control the driving of the white LED and the camera 402 so as to illuminate a cap section CP of the specimen container T held in the transported sample rack L by using the white LED and image the cap section CP by using the camera 402. The information processing unit 5C uses the image captured by the camera 402 to discriminate the type of the specimen container by the same process as in the above-described first to third embodiments. When aspirating a specimen by aspiration sections in the first measuring unit 2C and the second measuring unit 3C, the first measuring unit 2C and the second measuring unit 3C determines a descent amount of the aspiration section in accordance with the type of the specimen container discriminated as described above and aspirates the specimen. The aspirated specimen is measured by the first measuring unit 2C and the second measuring unit 3C as in the above-described first to third embodiments. In addition, in this configuration, a label section with a certain color or a certain size may be imaged so that by using the image of the imaged label section, as in the above-described second and third embodiments, an imaging error can be prevented from occurring due to individual differences between the devices and the type of the specimen container can be discriminated with higher accuracy.

In the above-described first to third embodiments, the configuration has been described in which the system control apparatus 8 determines the type of a specimen container and the blood cell analyzing apparatus 5 and the smear preparing apparatus 6 determine a descent amount of an aspiration tube in accordance with the type of the specimen container. However, the invention is not limited to this. A configuration in which the system control apparatuses 8, 8A and 8B determine descent amounts of the aspiration tubes of the blood cell analyzing apparatus 5 and the smear preparing apparatus 6 from an image of the cap of a specimen container and notify the determined descent amounts to the blood cell analyzing apparatus 5 and the smear preparing apparatus, or in which the blood cell analyzing apparatus 5 and the smear preparing apparatus (or one of the blood cell analyzing apparatus 5 and the smear preparing apparatus) obtain an image of the cap section of a specimen container and analyze the image to determine the descent amount of the aspiration tubes may be employed.

In the above-described first and second embodiments, the configuration in which shape (dimension) and color information of a cap section is extracted from an image of the cap section and the type of a specimen container is determined by using the shape and color information has been described. In addition, in the third embodiment, the configuration in which shape (dimension) information of a cap section is extracted from an image of the cap section and the type of a specimen container is determined by using the shape information has been described. However, the invention is not limited to these. A configuration in which color information of a cap section is extracted from an image of the cap section and the type of a specimen container is determined by using the color information may be employed. A configuration in which a reference image of a cap section is stored for each type of specimen container and an image of the imaged cap section is compared with the reference image by pattern matching to determine the type of the specimen container may also be employed.

In the above-described first to third embodiments, the configuration in which a specimen container T accommodated in a sample rack L is imaged to determine the type of the specimen container by using the image has been described. However, the invention is not limited to this. A configuration in which a mechanism for pulling a specimen container T out of a sample rack L is provided so as to image the specimen container pulled out of the sample rack L and thereby determine the type of the specimen container by using the image may be employed.

In the above-described first to third embodiments, the configuration in which the measuring unit 51 including the aspiration tube 511a which can be vertically moved determines the descent amount of the aspiration tube 511a corresponding to the type of the specimen container on the basis of an image obtained by imaging a cap section CP of a specimen container T and the aspiration tube 511a is lowered by this descent amount has been described. However, the invention is not limited to this. A configuration in which the measuring unit includes a mechanism for grasping a specimen container and tilting the specimen container so that a cap section is positioned lower than the bottom of the specimen container, and an aspiration section for passing the aspiration tube through the cap section of the tilted specimen container by moving the aspiration tube diagonally in a forward direction to determine a movement distance of the aspiration tube on the basis of an image of the cap section of the specimen container and pass the aspiration tube through the cap section of the specimen container by moving the aspiration tube diagonally in a forward direction by the movement distance to thereby aspirate a specimen may be employed. In this case, the movement distance is determined not by the position (depth) of the bottom of the specimen container but to be suitable for the shape of the cap section such as the thickness and the length of the cap section, and the movement distance (insertion amount of the aspiration tube from the upper end of the cap section) of the aspiration tube into the specimen container is thus controlled.

In the above-described first to third embodiments, the configuration in which the aspiration tube 511*a* is lowered by a descent amount determined on the basis of an image of a cap section and the aspiration tube 511*a* is thus passed through the cap section of a specimen container to thereby aspirate a specimen has been described. However, the invention is not limited to this. An aspiration section may be configured so as to detect that the tip end of the aspiration tube is brought into contact with a cap section, and a descent amount (insertion amount) of the aspiration tube 511*a* from the cap section may be determined on the basis of an image of the cap section to thereby control the movement distance of the aspiration tube into a specimen container. In this case, a configuration in which when aspirating a specimen, the specimen is aspirated after the aspiration tube is further lowered by the determined descent amount from when it has been detected that the aspiration tube is being lowered and the tip end of the aspiration tube has been brought into contact with the cap section may be employed.

In the above-described first to third embodiments, the configuration in which the specimen processing systems 1, 1A and 1B include the blood cell analyzing apparatus 5 for classifying blood cells included in a specimen and counting the number of blood cells for each blood cell type has been described. However, the invention is not limited to this. A configuration in which the specimen processing system includes a specimen analyzing apparatus other than the blood cell analyzing apparatus, such as an immunity analyzing apparatus, a blood coagulation measuring apparatus, a biochemical analyzing apparatus or a urine analyzing apparatus and transports a blood specimen or an urine specimen to a measuring unit of the specimen analyzing apparatus may be employed.

In the above-described first to third embodiments, the configuration in which the computer performs the specimen container type discriminating process of the computer programs 84*a*, 814*a* and 824*a* so as to determine the type of a specimen container by using the computer operating as the system control apparatuses 8, 8A and 8B has been described. However, the invention is not limited to this. A configuration in which the specimen container type discriminating process is performed by using a dedicated hardware such as FPGA, ASIC or the like, capable of executing the same process as the above computer programs may be employed.

In the above-described first to third embodiments, the configuration in which the single computers 8*a*, 810*a* and 820*a* execute all the processes of the computer programs 84*a*, 814*a* and 824*a* has been described. However, the invention is not limited to this. A distribution system for distributing the same process as the above-described computer programs 84*a*, 814*a* and 824*a* to plural devices (computers) and performing the process may be employed.

In the above-described first to third embodiments, when a specimen container type error is detected, specimen container type error information (information indicating that the type of a specimen container is not registered in the specimen container table TBL3 or TBL31) is displayed on the liquid crystal display section 227. However, not only may the specimen container type error information be displayed on the liquid crystal display section 227, but reference characteristic information of the type of the specimen container in which the specimen container type error has been detected may also be newly registered in the specimen container table TBL3 or TBL31 to display on the liquid crystal display section 227 a registration screen for newly registering a descent amount corresponding to the type of the specimen container in the descent amount table TBL1. In addition, the registration screen may be displayed on a display section other than the liquid crystal display section 227.

In the above-described first and second embodiments, when the type of a specimen container is determined, R, G and B values of pixels in a specified area in an image are obtained and an average value of each of the R, G and B values is calculated so as to use the average values of the R, G and B values as color information of a cap section. However, the invention is not limited to this. Relative average values of the R and B values when an average value of the G value is set to 100 may be used as color information of a cap section. Even when the specimen container is illuminated with the same color, there is a variation in each of the R, G and B values by the brightness of the illumination. By using the relative average values of the R and B values with respect to the G value, the influence exerted by the brightness of the illumination is suppressed and the type of the specimen container can thus be determined with high accuracy.

In the above-described first to third embodiments, the configuration in which the cap section CP of the specimen container T is imaged so as to determine a descent amount of the aspiration tube 511*a* corresponding to the type of the specimen container T on the basis of the image has been described. However, the invention is not limited to this. A configuration in which the entire specimen container T including the cap section CP is imaged and the type of the specimen container T is discriminated on the basis of the image of the cap section in the image to determine a descent amount of the aspiration tube 511*a* corresponding to the type of the specimen container T may be employed.

In the above-described second embodiment, the configuration in which the label section 242 is imaged together with the cap section CP of the specimen container T has been described. In addition, in the third embodiment, the configuration in which the white section 252 is imaged together with the cap section CP of the specimen container T has been described. However, the invention is not limited to these. A configuration in which the label section 242 or the white section 252 is singly imaged separately from the cap section CP of the specimen container T so as to correct characteristic information or determine a threshold for a binarization process on the basis of the image may be employed. For example, a configuration in which when the device is started, the label section 242 or the white section 252 is automatically imaged so as to correct characteristic information or determine a threshold for a binarization process on the basis of the image until the device is shut down may be employed.

In the above-described second embodiment, the configuration in which when an average luminance value of the partial image of the white area 242*a* is more than the upper limit value N or less than the lower limit value M which are used as references, it is judged that the state of the imaging by the camera 225*a* is not normal, and an imaging error is thus output in order to prompt a user or a service man to take necessary measures, such as adjustment of the sensitivity of the camera 225*a*, adjustment of the light intensity of the white LED 225*c* and replacement of the white LED 225*c* has been described. However, the invention is not limited to this. A configuration in which the system control apparatus can control light intensity by adjusting a voltage which is applied to the white LED 225*c* used as a light source, and the system control apparatus automatically adjusts the light intensity of the white LED 225*c* when it is judged that the state of the imaging by the camera 225*a* is not normal may be employed.

In addition, a configuration in which the system control apparatus can control light-receiving sensitivity of the camera used as the imaging section 225a, and the system control apparatus automatically adjusts the sensitivity of the camera 225a when it is judged that the state of the imaging by the camera 225a is not normal may also be employed. A configuration in which the system control apparatus adjusts both the light intensity of the white LED 225c and the sensitivity of the camera 225a may also be employed.

In the above-described second embodiment, the configuration in which characteristic information of the cap section CP is corrected on the basis of the shape (length), luminance and color information of the label section 242, which are obtained from the partial image of the label section 242 in an image, and thus the type of a specimen container is discriminated on the basis of the characteristic information after the correction has been described. In addition, in the third embodiment, the configuration in which a threshold for a binarization process is determined on the basis of luminance information obtained from the partial image of the white section 252 in an image and characteristic information is obtained from the binarized image obtained by binarizing a difference image with this threshold to discriminate the type of a specimen container on the basis of the characteristic information has been described. However, the invention is not limited to this. A configuration in which reference characteristic information which is an object for comparison with characteristic information is corrected on the basis of the shape (length), luminance and color information of the label section 242 or the luminance information of the partial image of the white section 252 and the characteristic information and the reference characteristic information after the correction are compared with each other to discriminate the type of a specimen container may be employed. A configuration in which a difference between characteristic information and reference characteristic information is obtained and corrected on the basis of the shape (length), luminance and color information of the label section 242 or the luminance information of the partial image of the white section 252, and when the difference after the correction is close to zero in an error range, a specimen container type corresponding to the reference characteristic information is judged as the type of an imaged specimen container may also be employed.

In the above-described second embodiment, the configuration in which the color bar 241 is disposed near the imaging position 224 has been described. In addition, in the third embodiment, the configuration in which the reference bar 251 is disposed near the imaging position 224 has been described. However, the invention is not limited to these. The color bar 241 and the reference bar 251 may be provided at any positions if they are in the imaging range of the camera 225a during the imaging of the cap section CP of the specimen container T. For example, the color bar 241 and the reference bar 251 may be provided in a sample rack L. Moreover, any object other than the color bar 241 and the reference bar 251 may be provided if it is a tangible entity having a certain color and a certain size. For example, when the camera 225a is configured to obtain monochrome images and characteristic information of a cap is obtained by analyzing a monochrome image obtained by the camera 225a, a gray-scale may be used as the label section. In this manner, the image analyzing process can be easily performed.

In the second embodiment, the configuration in which the color bar 241 with an opening at the center thereof is provided to image a specimen container has been described. However, a configuration in which information on a width of the opening of the color bar 241 is obtained from an image and length information of the cap is thus corrected may be employed.

What is claimed is:

1. A specimen processing system, comprising:
   an imaging device that captures an image of a cap of a sealed specimen container containing a specimen;
   a system controller connected with the imaging device via a first interface, the system controller including a first computer readable memory including a first database and a first computer program embedded thereon, the first database comprising a relationship of feature values and types of specimen container;
   a specimen processing device, comprising:
      a measurement device that prepares the specimen and detects a measurement component from the specimen for analysis, the measurement device comprising:
         an aspirating device including a pipette having a sharp edge, moving the pipette to pierce a cap of the sealed specimen container and aspirating the specimen in the sealed specimen container by the pipette whereby the cap of the sealed specimen container remains in the specimen container during aspiration; and
         an information processing unit coupled to the measurement device and operable to control an operation of the measurement device, the information processing unit connected with the system controller via a second interface, the information processing unit including a second computer readable memory including a second database and a second computer program embedded thereon, the second database comprising a relationship of the types of specimen container and movement distances of the pipette;
   wherein the first computer program comprises instructions to:
      execute the imaging device for capturing an image of the sealed specimen container and receiving the image via the first interface;
      extract a feature value from the captured image; and
      determine a type of the sealed specimen container corresponding to the feature value with reference to the first database;
   wherein the second computer program comprises instructions to:
      receive the determined type of the sealed specimen container from the system controller via the second interface;
      retrieve a movement distance corresponding to the determined type with reference to the second database; and
      control the aspirating device to move the pipette by the movement distance and control the specimen processing device to process the specimen aspirated by the pipette;
   wherein the movement distance corresponds to an insertion amount of the pipette into the sealed specimen container which enables the pipette to approach near an inner bottom of the sealed specimen container without bringing into contact with the inner bottom;
   wherein an inner depth of the sealed specimen container varies depending on a specimen container type, and the movement distance is set to be customized for each specimen container type.

2. The specimen processing system of claim 1, wherein the image includes color information for each pixel; and the feature value includes the color information of the image.

3. The specimen processing system of claim 1, wherein the feature value includes a value relevant to a shape of a cap.

4. The specimen processing system of claim 1, wherein the imaging device captures an image of a whole length of the sealed specimen container, and
the feature value includes a length of a specimen container.

5. The specimen processing system of claim 4, wherein the imaging device captures the image of the cap of the specimen container and an image of a specimen rack accommodating the specimen container; and
the system controller obtains a length of the specimen container based on a position of the specimen rack and a position of the cap of the sealed specimen container in the image.

6. The specimen processing system of claim 1,
wherein the first database further comprises instructions that store a reference object which provides a reference image with respect to the image of the cap, and
wherein the imaging device further captures an image of the cap of the sealed specimen container and the reference image of the reference object; and
the system controller extracts the feature value on the basis of the image of the reference object and the image of the cap.

7. The specimen processing system of claim 6, wherein the system controller performs further operations of:
determining, on the basis of the image of the reference object, a physical feature of the background of the image;
correcting the feature value based on the physical feature of the background of the image; and
determining a type of the sealed specimen container corresponding to the corrected feature value.

8. The specimen processing system of claim 7, wherein the first computer readable memory stores reference feature information corresponding to the physical feature of the reference object, and
the system controller corrects the feature value, on the basis of the reference feature information and a determined physical feature.

9. The specimen processing apparatus of claim 6, wherein the system controller performs further operations of:
determining, on the basis of the image of the reference object, the physical feature of the environment of imaging;
extracting the feature value on the basis of the determined physical feature and the image of the cap.

10. The specimen processing system of claim 9,
wherein the system controller performs further operations of:
determining, on the basis of the determined physical feature, a processing condition for processing the image of the cap;
processing the image of the cap according to the determined processing condition; and
extracting the feature value from the processed image of the cap.

11. The specimen processing system of claim 6, wherein the imaging device accepts a change of a setting relating to an imaging condition; and
the system controller performs operations of:
determining a physical feature of the reference object, and
changing a setting according to the determined physical feature.

12. The specimen processing system of claim 6, wherein the imaging device comprises a camera and an illumination device that irradiates an object to be imaged,
the system controller performs further operations of:
determining a luminance of the image of the reference object; and
outputting, when the determined luminance of the image is not within a predetermined range, a notification to notify that sensitivity of the camera or light intensity of the illumination device is not at a predetermined status.

13. The specimen processing system of claim 6, wherein the system controller performs further operations of:
processing the image of the cap by eliminating a background of an image therefrom, by use of the image of the reference object; and
extracting the feature value from the processed image.

14. The specimen processing system of claim 6, wherein the first computer program comprises instructions to:
determine a type of the sealed specimen container corresponding to one of the feature values if the extracted feature value is identical to one of the feature values in the first database, or is substantially identical to one of the feature values in a predetermined value range, and
the system controller outputs a notification of an error if the extracted feature value is not identical to, or not substantially identical to any of the feature values in the first database.

15. The specimen processing system of claim 1, further comprising:
a transporting device that transports a specimen container to the aspirating device via an imaging position where the imaging device captures an image of a cap of the transported specimen container.

16. The specimen processing system of claim 1, wherein the aspirating device moves the pipette into the sealed specimen container by lowering the pipette.

17. The specimen processing system of claim 1, further comprising:
a grasping member that grasps the sealed specimen container and oscillates the grasped specimen container to stir the specimen accommodated therein,
wherein the aspirating device is configured to aspirate the specimen from the oscillated specimen container.

* * * * *